US012263181B2

(12) United States Patent
Staszak-Jirkovsky et al.

(10) Patent No.: US 12,263,181 B2
(45) Date of Patent: Apr. 1, 2025

(54) PHOSPHOLIPID COMPOSITIONS

(71) Applicant: MACHAVERT PHARMACEUTICALS LLC, Aurora, CO (US)

(72) Inventors: Jakub D. Staszak-Jirkovsky, Denver, CO (US); Lukas Kobr, Denver, CO (US); Gregory Miknis, Broomfield, CO (US); Colleen Hudson, Denver, CO (US); Luca Monfregola, Denver, CO (US); Pavel Jirkovsky, Praha-Čimice (CZ); Zbončáková Milada, Lovosice (CZ); Jason Duex, Denver, CO (US); Pitchaimani Kandasamy, Denver, CO (US)

(73) Assignee: MACHAVERT PHARMACEUTICALS LLC, Aurora, CO (US)

( * ) Notice: Subject to any disclaimer, the term of this patent is extended or adjusted under 35 U.S.C. 154(b) by 61 days.

(21) Appl. No.: 17/892,782

(22) Filed: Aug. 22, 2022

(65) Prior Publication Data
US 2022/0409641 A1 Dec. 29, 2022

Related U.S. Application Data

(63) Continuation of application No. 16/653,591, filed on Oct. 15, 2019, now Pat. No. 11,433,085, which is a continuation of application No. 15/637,126, filed on Jun. 29, 2017, now Pat. No. 10,493,086.

(60) Provisional application No. 62/356,197, filed on Jun. 29, 2016, provisional application No. 62/356,189, filed on Jun. 29, 2016.

(51) Int. Cl.
*A61K 31/685* (2006.01)
*A61K 9/00* (2006.01)
*A61K 9/48* (2006.01)
*A61K 31/688* (2006.01)
*A61K 35/57* (2015.01)
*A61P 35/00* (2006.01)
*A61P 35/02* (2006.01)

(52) U.S. Cl.
CPC .......... *A61K 31/688* (2013.01); *A61K 9/0053* (2013.01); *A61K 9/48* (2013.01); *A61K 31/685* (2013.01); *A61K 35/57* (2013.01); *A61P 35/00* (2018.01); *A61P 35/02* (2018.01); *A61K 2236/00* (2013.01)

(58) Field of Classification Search
CPC ........ A61K 31/685; A61K 35/57; A61P 35/02
See application file for complete search history.

(56) References Cited

U.S. PATENT DOCUMENTS

| 5,429,823 A | 7/1995 | Tremblay et al. |
| 6,602,861 B1 | 8/2003 | Pidgeon et al. |
| 7,838,511 B2 | 11/2010 | Lichtenberger et al. |
| 2004/0241249 A1 | 12/2004 | Sampalis et al. |
| 2008/0153782 A1 | 6/2008 | DuPont |
| 2014/0050780 A1 | 2/2014 | Cerundolo et al. |

FOREIGN PATENT DOCUMENTS

| CZ | 280686 B6 | 1/1994 |
| CZ | 282139 B6 | 10/1996 |
| WO | 2004050097 A1 | 6/2004 |

OTHER PUBLICATIONS

Niezgoda et al.; "Synthesis of Phosphatidylcholine with Conjugated Linoleic Acid and Studies on Its Cytotoxic Activity"; 2013; Aust. J. Chem; 66: 354-361; http://dx.doi.org/10.1071/CH12404 (Year: 2013).*
Niezgoda et al. "Synthesis of Phosphatidylcholine with Conjugated Linoleic Acid and Studies on Its Cytotoxic Activity;" Aust. J. Chem 66 (2013): 354-361; http://dx.doi.org.10.1071/CH12404.
Berdel, Wolfgang E. et al., "Cytotoxicity of Alkyl-Lysophospholipid Derivatives and Low-Alkyl-Cleavage Enzyme Activities In Rat Brain Tumor Cells," Cancer Research 43 (1983):541-545.
Fukunaga, Kenji, et al., "Marine phosphatidyl choline suppresses 1,2-dimethylhydrazine-induced colon carcinogenesis in rats by inducing apoptosis," Nutrition Research 28 (2008): 635-640.
Gladkowski, Witold, et al., "Isoluation of Pure Phospholipid Fraction from Egg Yolk," J Am Oil Chem Soc 89 (2012): 179-182.
Hossain, Zakir, et al., "Effect of polyunsaturated fatty acid-enriched phosphatidylcholine and phosphatidylserine on butyrate-induced growth inhibition, differentiation and apoptosis in Caco-2 cells," Cell Biochem Funct 24 (2006): 159-165.
Kara, Jindrich, :A novel nontoxic alkyl-phospholipid with selective antitumor activity, plamanyl-(N-acyl)-ethanolamine (PNAE), isolated from degenerating chick embryonal tissues and from an anticancer biopreparation cACPL, Neoplasma 33 (1986): 187-205.
Kara, Jindrich, et al., "New tumoricidal semisynthetic ether phospholipid, plasmanyl-(N-acyl)ethanolamine (PNAE(s)) and enhancement of its tumoricidal activity by calcium ions," Neoplasma 40 (1993): 213-217.
Karafiat, V. "Egg Yolk Phospholipids Enriched with 1-O-Octoadecyl-2-Oleoyl-sn-Glycero-3-Phospho-(N-Palmitoyl) Ethanolamine Inhibit development of Experimentally Induced Tumors," Folio Biological (Praha) 60 (2014): 220-227.
Kullenberg, Daniela, et al., "Health effects of dietary phospholipids," Lipids in Health and Disease 11 (2012), 13 pages.
Modolell, Manuel, et al., "Disturbance of Phospholipid Metabolism during the Selective Destruction of Tumor Cells Induced by Alkyl-lysophospholipids," Cancer Research 39 (1979): 4681-4686.

(Continued)

Primary Examiner — Timothy P Thomas
(74) Attorney, Agent, or Firm — Greenberg Traurig, LLP; Jonathan D. Ball; Scott Goncher

(57) ABSTRACT

Compositions involving a modified egg yolk extract for use as an effective anti-cancer agent are described. The modified egg yolk extract involves specific fractions of phosphatidylcholines and sphingomyelins modified and produced from a chemical synthesis applied to the extract that produce a beneficial effect on the inhibition of cancerous cell growth. Methods of administering these compositions are also described.

1 Claim, 8 Drawing Sheets

(56) References Cited

OTHER PUBLICATIONS

Sakakima, Yoshikazu, et al., "Prevention of hepatocarcinogenesis with phosphatidylcholine and menaquinone-4: In vitro and in vivo experiments," Journal of Heptaology 47 (2007) 83-92.

Vicenova, Monica, et al., "Evaluation of in vitro and in vivo anti-inflammatory activity of biologically active phospholipids with anti-neoplastic potential in porcine model," BMC Complementary and Alternative Medicine 14 (2014): 339-349.

Weichert, Jamey, et al, "Alkylphosphocholine Analogs for Broad-Spectrum Cancer Imaging and Therapy," Science Translational Medicine 6 (2014), 10 pages.

OVOSAN product, https://elivera.co.uk/products/ovosan-x-90-caps-fight-against-cancer, 5 pages.

Ren, http://www.mcrc4.com/?p=159, 2 pages.

Immuno-Research LTD, http://www.heimat-ltd.com/information/combination-of-marine-lipids-and-lecithin-2.html, 6 pages.

Van Blitterswijk, WJ, et al., "Anticancer mechanisms and clinical application of alkylphospholipids," Biochim Biophys Acta 1831 (2013): 663-674.

Kuerschner, Lars, et al., "Exogenous Ether Lipids Predominantly Target Mitochondria," PLOS One 7 (2012): e31342, 12 pages.

Hossain, Zakir, et al., "Growth Inhibition and Induction of Apoptosis of Colon Cancer Cell Lines by Applying Marine Phospholipid," Nutrition and Cancer 61 (2009): 123-130.

Kara, Jindrich, "Ether-phospholipid PNAE against the tumor cells: Prevention and therapy of metastases" 2000, 33 pages.

\* cited by examiner

PHOSPHOLIPID COMPOSITIONS

This application is a continuation of and claims priority under 35 U.S.C. § 120 to U.S. application Ser. No. 16/653,591, filed Oct. 15, 2019, which is a continuation of and claims priority under 35 U.S.C. § 120 to U.S. application Ser. No. 15/637,126, filed Jun. 29, 2017 which claims priority under 35 U.S.C. § 119 (e) to U.S. Provisional Patent Application Ser. Nos. 62/356,189 and 62/356,197, each filed Jun. 29, 2016, the entire contents of which are hereby incorporated by reference herein.

FIELD OF INVENTION

Pharmaceutical compositions comprising bioactive lipids and methods of treating mammals with bioactive lipids are disclosed. The bioactive lipids generally include phosphatidylcholine (PC) and/or sphingomyelin (SPH) compounds and are believed to be useful in the treatment of proliferative diseases including cancer.

BACKGROUND

Some phospholipids from natural sources are known to produce beneficial effects on various conditions in mammals. For example, phospholipids derived from hen egg yolk have been studied as potentially having therapeutic benefits. Natural hen egg yolk extracts are rich in a variety of bioactive phospholipids (BAP). When enriched to 30% with the N-acyl ether-phosphatidylethanolamine (NAEPE) 1-O-octadecyl-2-oleoyl-sn-glycero-3-phospho-(N-palmitoyl)ethanolamine, hen egg yolk extracts have been reported to have anti-cancer properties, including significantly interfering with tumor progression in in vivo chick models. See, Karafiat V., et al., *Folia Biologica* (Praha) 60, 220-227 (2014). This is consistent with earlier reports that 1-O-octadecyl/hexadecyl-2-oleoyl-sn-glycero-3-phospho-(N-palmitoyl)ethanolamine isolated from ischemic chicken embryos and/or made semisynthetically restricts growth of subcutaneous transplanted sarcomas in mice. See, Kara, J. et al., *Neoplasma* 33, 187-205 (1986) and Kara J. et al., *Neoplasma* 40 213-217 (1993).

It is generally believed that the alkyl-ether moiety in NAEPE is necessary for cytotoxic activity because ether-linked lipids are not catabolized in tumors and can accumulate and interfere with vital pathways of the cell. See, Kara, J. et al, *Neoplasma* 33, 187-205 (1986), Berdel, W. et al., *Cancer Res.* 43, 541 (1983), and Modolell, M., et al., *Cancer Res.*, 39 4681 (1979).

Unlike classical DNA-targeted cytotoxic agents, alkylphospholipids or BAP may target cellular and intracellular membranes. See Kuerschner, D., et al., *PLOS One* 7, e31342 (2012). When administered in therapeutic doses, alkylphospholipids may inhibit phosphatidylcholine biosynthesis, interfere with lipid transduction pathways, block the endoplasmic reticular transport, and interfere with the membrane lipid raft function. See, e.g., Blitterswijk. W., et al., *Biochim. Biophys. Acta.* 1831, 663-674 (2013). Lipid rafts are specialized plasma membrane microdomains having concentrations of cholesterol and sphingomyelins which spatially organize signaling pathways and regulate cell proliferation and apoptosis. See, e.g., van der Luit, A., et al., *Mol. Cancer Ther.* 6, 2337-2345 (2007). Lipid rafts are more abundant in cancer cells relative to normal cells and have been proposed to serve as entry points for cytotoxic agents into the cells. See, e.g., Li, Y., et al., *Am. J. Pathol.* 168, 1107-1118 (2006).

In addition to potential anti-neoplastic properties, it has also been reported that ischemic chick embryonic tissue extract enriched to 30% 1-O-octadecyl-2-oleoyl-sn-glycero-3-phospho-(N-palmitoyl)ethanolamine shows significant anti-inflammatory and immunomodulatory effects. See, Vicenova, M. et al., *Complementary and Alternative Medicine* 14 339 (2014). In in vivo studies of bacterially induced acute pneumonia it was demonstrated that BAP mixtures enriched with NAEPE had a positive effect on disease progression by lowering levels of IL-1β, IL-8 in sera and lowering white blood count, as well as reducing lung parenchyma. In vitro studies on the transcriptional activity of proinflammatory cytokine genes related to the activation of intracellular signaling pathways associated with inflammation showed the ability of certain BAP mixtures to influence the immune response of macrophages. Id. Moreover, the NAEPE enriched egg yolk extracts have activities which inhibit the phosphorylation of protein kinase C epsilon. Id.

It is an object of the present invention to identify biologically active lipids, including phosphatidylcholine (PC) and/or sphingomyelin (SPH) and/or lysophosphatidylcholine (LPC) compounds, and mixtures thereof, possessing therapeutic properties, including antiproliferative or antineoplastic properties. Moreover, it is an object of the invention to provide compositions and methods of using these compositions to treat proliferative diseases, including cancer.

SUMMARY OF INVENTION

Bioactive phospholipids (BAP) can be extracted from hen egg yolk (e.g., ischemic chick embryos) with alcohol and can be purified using acetone precipitation, as disclosed in Gladkowski, W, et al., *J. Am. Oil Chem.* 89 179-182 (2012), hereby incorporated by reference in its entirety. Such an egg yolk extract (designated herein as "BAP(−)") contains a wide range of phospholipids but, as demonstrated herein, does not show significant effects in in vitro and in vivo studies of cancer. It is known to treat BAP(−) mixtures with palmitoyl chloride to produce a material known as BAP(+). It has heretofore been believed that palmitoylization of the BAP(−) extract (producing BAP(+)) is required to yield therapeutic activity of the BAP mixture due to the creation of NAEPE's (or "PNAE") from the corresponding endogenous ethanolamines. As discussed previously, NAEPE's were thought to be the active constituent in BAP(+). See, e.g., Karafint V., et al., *Folia Biologica* (Praha) 60, 220-227 (2014) and Kara, J. et. al, *Neoplasma* 33, 187-205 (1986).

However, it has surprisingly been discovered that certain lipid components of chemically treated hen egg yolk provide anti-cancer effects, even in the absence or substantial absence (e.g., less than 5% (w/w), less than 1% (w/w), less than 0.1% (w/w), less than 0.01% (w/w), etc.) of the known active NAEPE's. Accordingly, the invention provides novel mixtures of lipids and pharmaceutical compositions thereof which are contemplated to be useful in the treatment of various diseases and conditions. In some aspects, the invention provides compositions comprising egg yolk extracts (e.g., hen egg yolk extracts, typically from *Gallus gallus domesticus*) enriched with one or more lipid components, such as phosphatidylcholine (PC) and/or sphingomyelin (SPH) and/or lysophosphatidylcholine (LPC) compounds. The invention is not limited to hen egg yolk extracts, but embraces extracts from any animal source or synthetic mixtures of lipids, having the same or substantially similar constituents. By "substantially similar" constituents is meant that at least the most abundant PC and/or SPH components are within 25% (w/w), preferably 15% and ideally 10% of the abundance in the hen egg yolk extracts defined herein. In some implementations, one or more lipids according to the invention are inhibitors of kinases, including protein kinases, notably tyrosine kinases, such as TTK. These compositions may be used to treat, for example, inflammation or proliferative diseases such as cancer.

Methods of treating proliferative diseases are also provided. In one aspect, a method for the treatment of a mammal (e.g., a human) suffering from cancer are provided comprising administering therapeutically effective amounts of any of the lipid mixtures described herein, or pharmaceutical compositions thereof. In particular, the lipid mixtures are derived from egg yolk extracts (e.g., hen egg yolk extracts, etc.) enriched in phosphatidylcholine and/or sphingomyelin compounds and/or lysophosphatidylcholine compounds or synthetically derived mixtures that are substantially similar thereto. In various implementations, the compositions are administered (e.g., orally) for the treatment of a cancer, including, without limitation, bladder, blood (e.g. lymphoma, Jurkat cancer cell line, etc.) brain (e.g. T98G cancer cell line, etc.), breast (e.g. 231 cancer cell line, etc.), cervical (e.g. HeLa cancer cell line, etc.), colorectal (e.g. HCT116 cancer cell line, etc.), esophageal, kidney, liver (e.g. HepG2 cancer cell line, etc.), lung (e.g. H358 cancer cell line, A549 cancer cell line, etc.), ovarian (e.g. SK-OV-3 cancer cell line, etc.), pancreatic (e.g. Panc1 cancer cell line, Capan-2 cancer cell line, etc.), skin (e.g. M14 cancer cell line, etc.), prostate (e.g. DU-145 cancer cell line, etc.), thyroid, or uterine cancers.

DETAILED DESCRIPTION OF THE INVENTION

Figure 1:
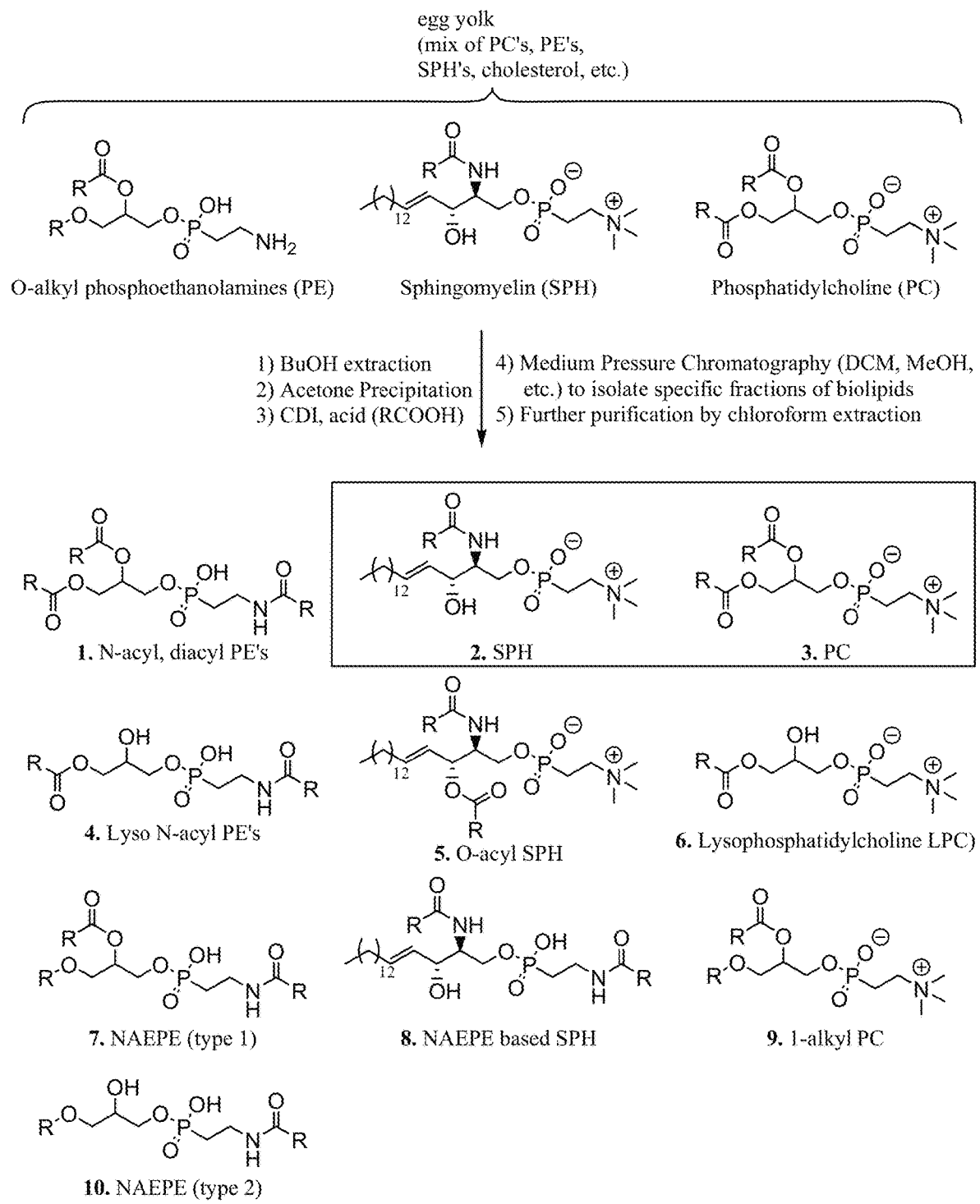
FIG. 1 illustrates an isolation of specific set of phospholipids derived from an egg extract. The initial egg yolk mixture comprises O-alkyl PE's, SPH's, PC's and other constituents. It will be understood that "R" groups on any compound class in FIG. 1 may be any aliphatic radical, and more typically, the monovalent hydrocarbon radical of a naturally occurring fatty acid. In the derivation illustrated, phospholipids are extracted from egg yolk using butanol (step 1) and further purified by adding the butanol extract to chilled acetone and collecting the lipids which precipitate from the mixture (step 2). These precipitated lipids are then reacted with CDI and an acid (for example, using an ethyl acetate:triethanolamine solvent comprising an amount of about triethanolamine for complete solvation of the precipitated lipids). Such reaction may produce the ten lipid classes shown. Medium pressure chromatography (step 4) is then used to further isolate only specific lipid classes (e.g. SPH, PC, LPC) and the final product may then be further purified using water/chloroform extraction to remove residual degradation products produced during chromatographic separation (step 4).

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive.

All terms used herein are intended to have their ordinary meaning unless otherwise provided. As used herein, the term "consisting essentially of" is intended to limit the invention to the specified materials or steps and those that do not materially affect the basic and novel characteristics of the claimed invention, as understood from a reading of this specification.

Whenever a term is identified by reference to a range, the range will be understood to explicitly disclose the endpoints and every element or value within the range thereof. The exact values of all half integral numeric values will also be understood to be specifically disclosed in any range and subsets of the original range. For example, a range of from about 0.1% to about 3% specifically discloses a percentage of 0.1%, 0.5%, 1%, 1.5%, 2%, 2.5%, and 3%, and any subranges formed by those intermediate values.

Where two or more substituents are referred to as being "independently selected from" a listing of alternatives, it is meant that each substituent can be any element of that group, independent of the identity of other substituents.

Unless otherwise stated, the phrase "substantially free" refers to an amount of a component that is sufficiently low such that the component contributes no significant properties (e.g., bioactivity, etc.) to the bulk, and, in any event will be less than about 5.0% by weight or less than about 4.0% or less than about 3.0% by weight or less than about 2.0% by weight or less than about 1.0% by weight or less than about 0.5% by weight or less than about 0.25% by weight or less than about 0.1% by weight, based on the total weight of the composition or based on the weight of a given component depending on the context.

As used herein, "% by weight" or "% wt." or "w/w" refers to the weight percent of a component in relation to the total weight of the composition unless otherwise stated. Every reference to percentage or % herein is given on a % by weight basis, unless stated otherwise. It will be understood that the sum of all weight % of individual components within a composition or within indicated component will not exceed 100%.

As used herein, the term "about" modifying a quantity refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like, as understood by persons of ordinary skill in the art. Whether or not modified by the term "about," the claims include equivalents to the quantities.

A "patient in need thereof," as used herein, refers to a human individual, male or female, who would benefit from administration of therapeutically effective doses of the lipid compositions. As described herein, in some embodiments, an individual in need thereof is suffering from a proliferative disorder such as cancer. In some embodiments, an individual in need thereof has been diagnosed by a medical doctor with a proliferative disorder requiring treatment. A patient in need or an individual in need are used interchangeably herein.

As used herein, the phrase "pharmaceutically acceptable" generally safe for ingestion or contact with biologic tissues at the levels employed. Pharmaceutically acceptable is used interchangeably with physiologically compatible. It will be understood that the pharmaceutical compositions of the invention include nutraceutical compositions (e.g., dietary supplements) unless otherwise specified.

The phrase "therapeutically effective amount," as used herein, means an amount necessary to provide the indicated therapeutic benefit. For example, a therapeutically effective amount may be from about 1 mg to about 10 g administered once (q.d.) or twice (b.i.d.) daily.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valences, etc., and to give compounds which are not inherently unstable. For example, any carbon atom will be bonded to two, three, or four other atoms, consistent with the four valence electrons of carbon.

Any of the compounds of the present disclosure may be in the form of pharmaceutically acceptable salts. "Pharmaceutically acceptable salts," as used herein, denotes salts that are physiologically compatible, as defined herein, and that possess the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate, and sodium hydroxide.

As used herein, an "enriched" extract is meant that the relative abundance of a given phospholipid in relation to any other phospholipids in the composition is increased in the extract compared to the relative abundance of the same phospholipid to the same other phospholipids in the parent composition from which the extract is derived.

As used herein, "hen egg yolk extract" refers to the yolk extract of any avian species. In some embodiments, the hen egg is from a species from the genus *Gallus*. In some embodiments, the hen egg is from the species Genus *Gallus*. In other embodiments, the hen egg is from the species *Gallus gallus domesticus*.

A large portion of the lipids found in hen egg yolk are phospholipids comprising a choline head group which include alkylphospholipids and phosphatidylcholine (PC) compounds. These choline comprising phospholipids generally have the structure of formula I(a):

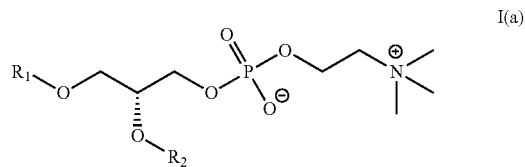

where $R_1$ and $R_2$ can be independently any monovalent $C_1$-$C_{30}$ radical, but are typically independently groups R or R—C(O)— where R is an aliphatic hydrocarbon chain, and more typically corresponding to naturally occurring fatty acids (or the acyl portion thereof). The acyl groups may correspond to the acyl portion of naturally occurring fatty acids such as ω-3 and ω-6 fatty acids. As used herein, a reference to a lipid that comprises a fatty acid will be understood to refer to the acyl group of the indicated fatty acid (i.e., where the lipid is esterified with the fatty acid), unless otherwise specified. For example, a phosphatidylcholine of formula I(a) comprising a docosahexaenoic fatty acid (e.g., (C22:6, all cis-4,7,10,13,16,19), etc.) has a docosahexaenoyl acyl group at position $R_1$ and/or $R_2$.

Some naturally occurring fatty acids can provide beneficial effects to cells, but are not naturally occurring in many mammalian bodies. Fatty acids (of the form R—COOH) typically have a long aliphatic chain (R), which is normally saturated, unsaturated, or poly-unsaturated, connected to a carboxylic acid (—COOH) head group. The corresponding acyl group will therefore have the form R—(CO)—. Most naturally occurring fatty acids have an unbranched hydrocarbon chain of an even number of carbon atoms (typically from 4 to 28). A fatty acid (or acyl radical thereof) may be denoted by its lipid number which indicates both the length of hydrocarbon chain of a fatty acid and the number of double bonds in that chain. In some embodiments, any double bond may be in the cis or trans (or E or Z) configuration. In some embodiments, all double bonds within a given fatty acid (or acyl fragment thereof) will be in the cis configuration. For example, a (C22:5) fatty acid has an unbranched hydrocarbon chain with a length of 22 carbon atoms and 5 double bonds and the corresponding C22 acyl radical has the structure RC(O)—, where R is a hydrocarbon chain with a length of 21 carbons and having 5 double bonds. ω-n numbers on fatty acids indicate the carbon distance (n) from the terminal methyl carbon (ω) on the fatty acid where the first double bond is located. An unsaturated fatty acid may be designated by the location of each double bond and the isomeric configuration of that bond (e.g., cis or trans). The location of the double bond may also be designated, for example, through the carbon number from which the double bond is located and extending toward the terminal methyl carbon. Unless otherwise specified, the carbon number is used to designated the double bond position. For example, a (C22:5, all cis-7,10,13,16,19) fatty acid acyl group has the structure:

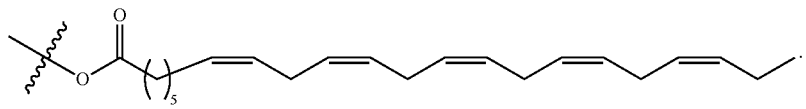

Unless otherwise indicated, successive double bonds are assumed to be separated by a single methylene (—CH$_2$—) unit. Table 1 shows a common name, systematic name, and structure of some fatty acids (and corresponding acyl portions thereof) that may be suitable R$_1$ and/or R$_2$ substituents.

TABLE 1

| Common Name (Lipid Number) | Systematic Name | Structure |
|---|---|---|
| Crotonic acid (C4:1) | (E)-2-Butenoic acid | 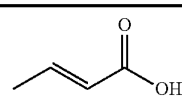 |
| Myristic acid (C14:0) | Tetradecanoic acid | 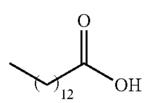 |
| Myristoleic acid (C14:1) | (Z)-9-Tetradecenoic acid | 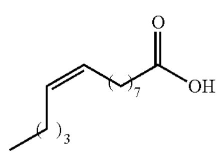 |
| Palmitic acid (C16:0) | Hexadecanoic acid | 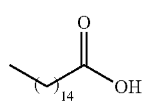 |
| Palmitoleic acid (C16:1) | (Z)-9-Hexadecenoic acid | 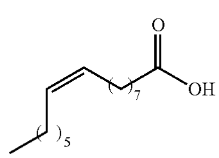 |
| Sapienic acid (C16:1) | (Z)-6-Hexadecenoic acid | 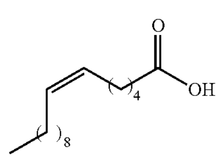 |
| Margaric Acid (C17:0) | Heptadecanoic acid | 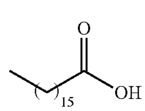 |
| Stearic acid (C18:0) | Octadecanoic acid | 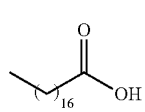 |

TABLE 1-continued

| Common Name (Lipid Number) | Systematic Name | Structure |
|---|---|---|
| Elaidic acid (C18:1) | (E)-9-Octadecenoic acid | 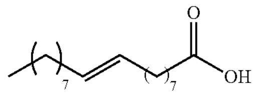 |
| Oleic Acid (C18:1) | (Z)-9-Octadecenoic acid | 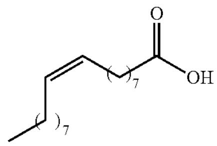 |
| cis-Vaccenic acid (C18:1) | (Z)-11-Octadecenoic acid | 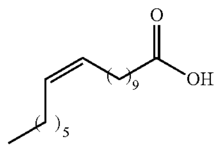 |
| Vaccenic acid (C18:1) | (E)-11-Octadecenoic acid | 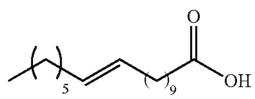 |
| Linoleic acid (C18:2) | (9Z,12Z)-9,12-Octadecadienoic acid | 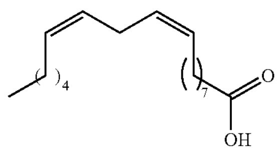 |
| α-Linolenic acid (C18:3) | (9Z,12Z,15Z)-9,12,15-Octadecatrienoic acid | 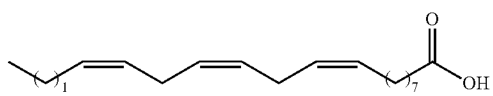 |
| Γ-Linolenic acid (C18:3) | (6Z,9Z,12Z)-6,9,12-Octadecatrienoic acid | 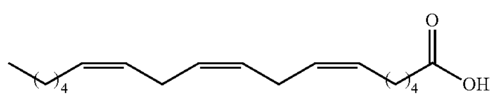 |
| Pinolenic acid (C18:3) | (5Z,9Z,12Z)-5,9,12-Octadecatrienoic acid | 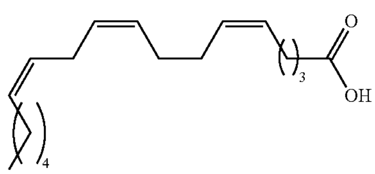 |
| α-Eleostearic acid (C18:3) | (9Z,11E,13E)-9,11,13-Octadecatrienoic acid | 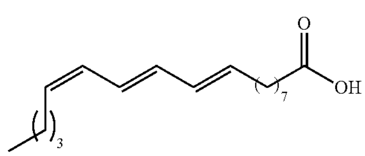 |
| β-Eleostearic acid (C18:3) | (9E,11E,13E)-9,11,13-Octadecatrienoic acid | 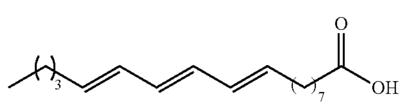 |
| Stearidonic acid (C18:4) | (6Z,9Z,12Z,15Z)-6,9,12,15-Octadecatetraenoic acid | 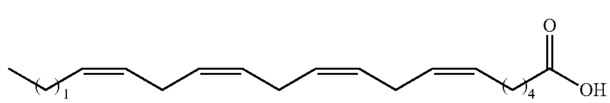 |
| Bosseopentaenonic acid (C18:5) | (5Z,8Z,10Z,12Z,14Z)-5,8,10,12,14-Eicosapentaenoic acid | |

TABLE 1-continued

| Common Name (Lipid Number) | Systematic Name | Structure |
| --- | --- | --- |
| Nonadecylic acid (C19:0) | Nonadecanoic acid | 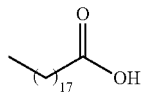 |
| Arachidic acid (C20:0) | Eicosanoic acid | 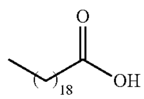 |
| Gadoleic acid (C20:1) | (9Z)-9-Eicosenoic acid | |
| Gondoic acid (C20:1) | (Z)-11-Eicosenoic acid | |
| Eicosadienoic acid (C20:2) | (11Z,14Z)-11,14-Eicosadienoic acid | 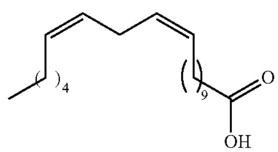 |
| Mead acid (C20:3) | (5Z,8Z,11Z)-5,8,11-Eicosatrienoic acid | 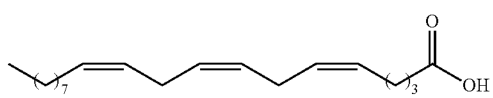 |
| Dihomo-γ-linolenic acid (C20:3) | (8Z,11Z,14Z)-8,11,14-Eicosatrienoic acid | |
| ω-3-Eicosatrienoic acid (C20:3) | (11Z,14Z,17Z)-11,14,17-Eicosatrienoic acid | 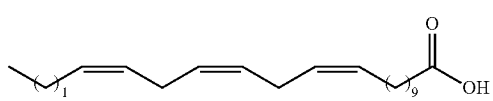 |
| Arachidonic acid (C20:4) | (5Z,8Z,11Z,14Z)-5,8,11,14-Eicosatetraenoic acid | 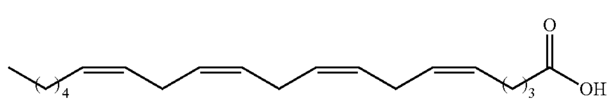 |
| Juniperonic acid (C20:4) | (8Z,11Z,14Z,17Z)-8,11,14,17-Eicosatetraenoic acid | 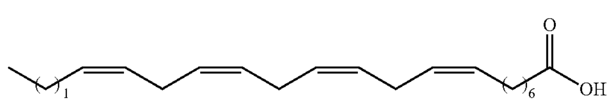 |
| Eicosapentaenoic acid (C20:5) | (5Z,8Z,11Z,14Z,17Z)-5,8,11,14,17-Eicosapentaenoic acid | |
| Heneicosylic acid (C21:0) | Heneicosanoic acid | 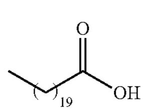 |

TABLE 1-continued

| Common Name (Lipid Number) | Systematic Name | Structure |
|---|---|---|
| Behenic acid (C22:0) | Docosanoic acid | 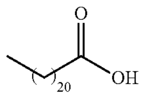 |
| Brassidic acid (C22:1) | (E)-13-Docosenoic acid | 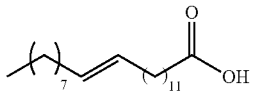 |
| Erucic acid (C22:1) | (Z)-13-Docosenoic acid | 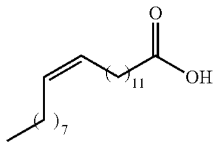 |
| Docosadienoic acid (C22:2) | (13Z,16Z)-13,16-Docosadienoic acid | 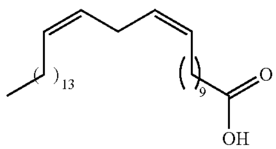 |
| Adrenic acid (C22:4) | 7Z,10Z,13Z,16Z-Docosatetraenoic acid | 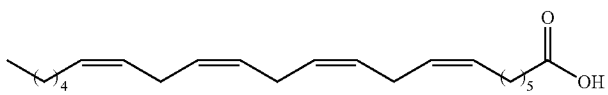 |
| Osbond acid (C22:5) | (4Z,7Z,10Z,13Z,16Z)-4,7,10,13,16-Docosapentaenoic acid | 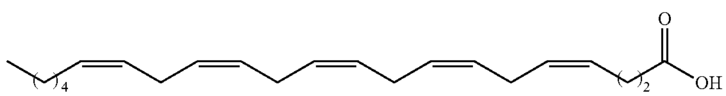 |
| Clupanodonic acid (C22:5) | (7Z,10Z,13Z,16Z,19Z)-7,10,13,16,19-Docosapentaenoic acid | 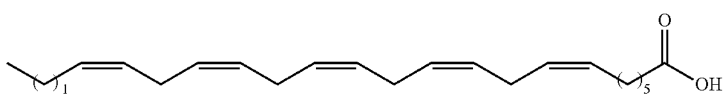 |
| Docosahexaenoic acid (C22:6) | (4Z,7Z,10Z,13Z,16Z,19Z)-4,7,10,13,16,19-Docosahexaenoic acid | 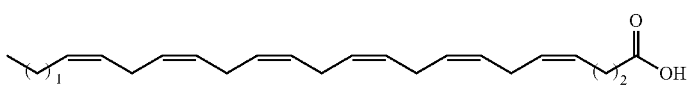 |
| Herring acid (C24:6) | (6Z,9Z,12Z,15Z,18Z,21Z)-6,9,12,15,18,21-Tetracosahexaenoic acid | 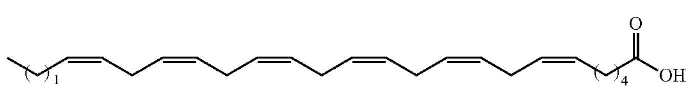 |
| Heneicosylic acid (C23:0) | Heneicosanoic acid | 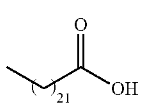 |
| Lignoceric acid (C24:0) | Tetracosanoic acid | 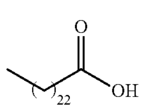 |
| Nervonic acid (C24:1) | (Z)-15-Tetracosenoic acid | 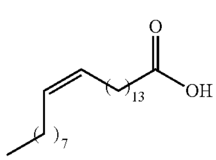 |
| Tetracosanolpentaenoic acid (C24:5) | (9Z,12Z,15Z,18Z,21Z)-9,12,15,18,21-Tetracosapentaenoic acid | |

TABLE 1-continued

| Common Name (Lipid Number) | Systematic Name | Structure |
|---|---|---|
| Cerotic acid (C26:0) | Hexacosanoic acid | ![structure: CH3-(CH2)24-COOH] |

It will be understood that in the event of any inconsistency between the common name, the systematic name, and the chemical structure in Table 1, all such compounds will be considered as embraced by the invention. For example, in the event of a discrepancy in the systematic name and the structure provided, both the compound corresponding to the systematic name number and the compound corresponding to the structure will be considered within the scope of the invention.

In some embodiments, the compounds of formula I(a) and/or II(a) will include a group $R_1$, $R_2$, and $R_6$ independently selected from the lipids of Table 1.

Pharmaceutical compositions comprising lipid mixtures which may be extracted from hen egg yolk are described herein. In some embodiments, the pharmaceutical compositions are derived (e.g. extracted, chemically reacted, isolated, separated, and/or combinations thereof) from hen egg yolk. However, it should be understood that, unless otherwise stated, the invention is not limited to any method of preparation. Accordingly, in some embodiments, the lipid mixture may be obtained "synthetically," for example, by preparing blends of the constituent lipids, derived from any source or made synthetically. Without limitation, BAP(+) and BAP(-) preparations from which the lipid extracts of the invention may be derived are available from AREKO Ltd. (Prague, CZ). BAP(+) may be synthesized from BAP(-) by the methods disclosed in CZ Pat No 282,139 to Kira et al., CZ Pat No 275,396 to Kira et al., CZ Pat No 276,477 to Kira et al., each hereby incorporated by reference in their entirety and specifically in relation to synthetic preparation of biologically active phospholipids. In some embodiments, the method of preparation will define the components of the BAP mixture. In some embodiments, the lipid mixture may be obtained synthetically or derived from an animal, plant, or microbial (e.g., bacterial) source, be substantially identical to the compositions prepared from hen egg yolk (e.g., the composition will have about 80% or about 90% or about 95% or about 99% or 100% of the same components) and/or the abundance of the chief components (i.e., those constituting >5% by weight of the extract) will be within about 50%, or about 25%, or about 15%, or about 10% by weight of the abundance of the same constituents in the hen egg yolk extracts described herein.

The BAP(-) extract may be isolated and purified as disclosed in Gladkowski, W, et al., *J. Am. Oil Chem.*, 89 179-182, (2012), hereby incorporated by reference in its entirety. In some embodiments, hen egg yolk extracts are derived from hen egg yolk (e.g., available from Sigma Aldrich, MO) by organic solvent (e.g., methanol, ethanol, propanol, isopropanol, butanol, dichloromethane, acetone, hexane, or combinations thereof) extraction. The solvent may be polar, polar-protic, and/or nonpolar. Preferably, the extract is obtained by extraction of hen egg yolk with ethanol and/or butanol. In some embodiments, hen egg yolk extracts are purified by de-oiling (precipitating) with acetone. In some embodiments, egg yolk extracts are precipitated with chilled (e.g., less than 10° C. or less than 5° C.) acetone. In various embodiments of the invention, hen egg yolk extracts are reacted with an activated carboxylic acid species (e.g. acid anhydrides, acid chlorides, etc.). The activated acid species is an activated derivative (e.g., acyl hydride, acyl halide, etc.) of palmitic acid. The carboxylic acid may be, for example, a $C_2$-$C_{30}$ acid having an aliphatic chain, such as a $C_{1-29}$ saturated alkyl chain. In some embodiments, the extracts are reacted with 1,1'Carbonyldiimidazole (CDI) and an acid, such as a $C_4$-$C_{26}$ fatty acid (e.g., palmitic acid, stearic acid, eicosanoic acid, tetradecanoic acid, hexanoic acid, etc.). In some embodiments, the reacted extracts may then be separated by chromatography to isolate specific mixtures of phospholipids. Isolation of specific phospholipids may be performed using, for example, chromatographic separation (e.g., column chromatography, flash chromatography, liquid crystal chromatography, thin layer chromatography, medium pressure chromatography, liquid column chromatography, semi-preparative chromatography, silica gel chromatography, reverse phase chromatography, etc.). In some embodiments, the isolation may involve the combination of two or more chromatographic separations to isolate specific fractions of biophospholipds. A schematic illustration of such a process is shown in FIG. 1. Also provided herein are methods for extraction of biologically active phospholipids from a mixture of phospholipids (e.g. hen egg yolk, chemically treated egg yolk, etc.) comprising isolating various fractions of said mixture by medium pressure silica gel chromatography. Typically, medium pressure gel chromatography utilizes tighter packed separation columns, higher flow rates, and more precise gradient control than other chromatographic techniques. Medium pressure chromatographic techniques may allow for the phospholipid mixture to minimize contact time with silica which, in turn, minimizes the amount of degradation of the phospholipid mixture (e.g., by converting PCs in to LPCs).

Typically, the flow rate in a chromatographic experiment may be set by determining the minimum variance per unit of column length (e.g., by determining the minimum variance per unit length of a separation column to the linear mobile phase velocity by considering the physical kinetic, and thermodynamic properties of the separation). Typically this maximizes the efficiency of the chromatographic experiment. However, it has surprisingly been found that using a flow rate below the optimal value will result in improvements in the isolation of fractions with less degradation of biophospholipids. In some embodiments, the chromatography is performed with a silica column and a flow rate that is suboptimal for said column size. The flow rate for may be less than about 80% (e.g., less than about 50%) of the optimal flow rate. In some embodiments, the chromatography is performed with one or more eluents comprising chloroform. In some embodiments the chromatography is performed with at least two different eluents. One of these two eluents may be basic and the other of said at least two eluents may alcoholic (i.e. the eluent may comprise alcohol).

The eluent may comprise water, ammonium hydroxide, triethylamine, methanol, ethanol, propanol, dichloromethane, isopropanol, chloroform, hexanes, butanol, or combinations thereof. In some embodiments, the fractions of isolated biophospholipids may be further purified by removal of any degradation products produced during the isolation. For example, such purification may be achieved by extraction with a solvent comprising chloroform. In some embodiments, the mixture of biologically active phospholipids may be produced by the medium pressure chromatographic separation and purification as described in Example 2.

In some embodiments, the extracts will comprise one or more phosphatidylcholines (PC). PCs may produce beneficial effects with other PCs with different sets of acyl functional groups at positions $R_1$ and $R_2$. The acyl functional group may comprise a monovalent hydrocarbon radical that is saturated or unsaturated. By unsaturated, it is meant that the hydrocarbon contains one or more double bonds (e.g. two, three, four, five, six, etc.). The hydrocarbon may be branched or unbranched. The hydrocarbon may be a $C_4$-$C_{35}$ (e.g $C_{10}$-$C_{30}$, $C_{12}$-$C_{28}$, $C_{14}$-$C_{24}$, etc.) alkyl, alkenyl, alkynyl, aryl, or aralkyl monovalent radical. Each double bond in the hydrocarbon may independently be in the cis or trans configurations. The hydrocarbon may have all double bonds in the cis configuration. Some embodiments of the invention involve pharmaceutical compositions comprising one or more phosphatidylcholines having the structure of formula I(a):

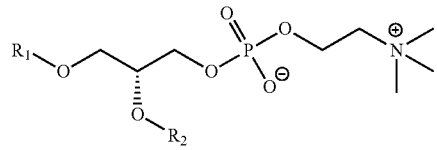

I(a)

where $R_1$ and $R_2$ are independently hydrogen or an acyl group comprising a hydrocarbon chain. In some embodiments, the hydrocarbon chain is the corresponding acyl group of a naturally occurring fatty acid. In some embodiments, the phosphatidylcholine is a lysophosphatidylcholine (e.g., $R_2$ is hydrogen). In some embodiments, $R_1$ is hydrogen. In some embodiments, at least one of $R_1$ or $R_2$ is hydrogen. In some embodiments, neither $R_1$ nor $R_2$ is hydrogen. The hydrocarbon chain may be saturated or unsaturated. In some embodiments, one of $R_1$ and $R_2$ may be saturated and the other of $R_1$ and $R_2$ may be unsaturated. In other embodiments, both $R_1$ and $R_2$ are both saturated. In other embodiments, $R_1$ and $R_2$ are unsaturated. In some embodiments, each of $R_1$ and $R_2$ is independently chosen from a fatty acid (or acyl portion thereof) listed in Table 1. The acyl group may be derived from a fatty acid with any co number (i.e., ω-3, ω-4, ω-5, ω-6, ω-8, etc.).

Table 2 provides a non-limiting list of phosphatidylcholines that may be used beneficially, alone or in combination with one another, for providing a patient benefit, for example, cancer treatment.

TABLE 2

| Compound | Name | $R_1$ | $R_2$ |
| --- | --- | --- | --- |
| PC1 | 1-palmitoleoyl-2-linoleoyl-sn-glycero-3-phosphocholine | (C16:1) | (C18:2) |
| PC2 | 1-palmitoyl-2-α-linolenoyl-sn-glycero-3-phosphocholine | (C16:0) | (C18:3) |
| PC3 | 1-palmitoyl-2-arachidonoyl-sn-glycero-3-phosphocholine | (C16:0) | (C20:0) |
| PC4 | 1,2-dilinoleoyl-sn-glycero-3-phosphocholine | (C18:2) | (C18:2) |
| PC5 | 1-palmitoyl-2-docosahexaenoyl-sn-glycero-3-phosphocholine | (C16:0) | (C20:6) |
| PC6 | 1-α-linolenoyl-2-docosahexaenoyl-sn-glycero-3-phosphocholine | (C18:3) | (C20:6) |
| PC7 | 1-palmitoleoyl-2-oleoyl-sn-glycero-3-phosphocholine | (C16:1) | (C18:1) |
| PC8 | 1-palmitoyl-2-linoleoyl-sn-glycero-3-phosphocholine | (C16:0) | (C18:2) |
| PC9 | 1-palmitoleoyl-2-docosahexaenoyl-sn-glycero-3-phosphocholine | (C16:1) | (C20:6) |
| PC10 | 1-palmitoyl-2-osbondoyl-sn-glycero-3-phosphocholine | (C16:0) | (C22:5) |
| PC11 | 1-oleoyl-2-arachidonoyl-sn-glycero-3-phosphocholine | (C18:1) | (C20:0) |
| PC12 | 1-oleoyl-2-linoleoyl-sn-glycero-3-phosphocholine | (C18:1) | (C18:2) |
| PC13 | 1-stearoyl-2-arachidonoyl-sn-glycero-3-phosphocholine | (C18:0) | (C20:0) |
| PC14 | 1-palmitoyl-2-oleoyl-sn-glycero-3-phosphocholine | (C16:0) | (C18:1) |
| PC15 | 1-oleoyl-2-docosahexaenoyl-sn-glycero-3-phosphocholine | (C18:1) | (C20:6) |
| PC16 | 1,2-dioleoyl-sn-glycero-3-phosphocholine | (C18:1) | (C18:1) |
| PC17 | 1-stearoyl-2-linoleoyl-sn-glycero-3-phosphocholine | (C18:0) | (C18:2) |
| PC18 | 1-stearoyl-2-oleoyl-sn-glycero-3-phosphocholine | (C18:0) | (C18:1) |
| PC19 | 1,2-dipalmitoleoyl-sn-glycero-3-phosphocholine | (C16:1) | (C16:1) |
| PC20 | 1-palmitoleoyl-2-palmitoyl-sn-glycero-3-phosphocholine | (C16:1) | (C16:0) |
| PC21 | 1-palmitoleoyl-2-α-linolenoyl-sn-glycero-3-phosphocholine | (C16:1) | (C18:3) |
| PC22 | 1-palmitoleoyl-2-stearoyl-sn-glycero-3-phosphocholine | (C16:1) | (C18:0) |

TABLE 2-continued

| Compound | Name | R₁ | R₂ |
|---|---|---|---|
| PC23 | 1-palmitoleoyl-2-arachidonoyl-sn-glycero-3-phosphocholine | (C16:1) | (C20:0) |
| PC24 | 1-palmitoleoyl-2-osbondoyl-sn-glycero-3-phosphocholine | (C16:1) | (C22:5) |
| PC25 | 1-palmitoyl-2-palmitoleoyl-sn-glycero-3-phosphocholine | (C16:0) | (C16:1) |
| PC26 | 1,2-dipalmitoyl-sn-glycero-3-phosphocholine | (C16:0) | (C16:0) |
| PC27 | 1-palmitoyl-2-stearoyl-sn-glycero-3-phosphocholine | (C16:0) | (C18:0) |
| PC28 | 1-linoleoyl-2-palmitoleoyl-sn-glycero-3-phosphocholine | (C18:2) | (C16:1) |
| PC29 | 1-linoleoyl-2-palmitoyl-sn-glycero-3-phosphocholine | (C18:2) | (C16:0) |
| PC30 | 1-linoleoyl-2-α-linolenoyl-sn-glycero-3-phosphocholine | (C18:2) | (C18:3) |
| PC31 | 1-linoleoyl-2-oleoyl-sn-glycero-3-phosphocholine | (C18:2) | (C18:1) |
| PC32 | 1-linoleoyl-2-stearoyl-sn-glycero-3-phosphocholine | (C18:2) | (C18:0) |
| PC33 | 1-linoleoyl-2-arachidonoyl-sn-glycero-3-phosphocholine | (C18:2) | (C20:0) |
| PC34 | 1-linoleoyl-2-docosahexaenoyl-sn-glycero-3-phosphocholine | (C18:2) | (C20:6) |
| PC35 | 1-linoleoyl-2-osbondoyl-sn-glycero-3-phosphocholine | (C18:2) | (C22:5) |
| PC36 | 1-α-linolenoyl-2-palmitoleoyl-sn-glycero-3-phosphocholine | (C18:3) | (C16:1) |
| PC37 | 1-α-linolenoyl-2-palmitoyl-sn-glycero-3-phosphocholine | (C18:3) | (C16:0) |
| PC38 | 1-α-linolenoyl-2-linoleoyl-sn-glycero-3-phosphocholine | (C18:3) | (C18:2) |
| PC39 | 1,2-di-α-linolenoyl-sn-glycero-3-phosphocholine | (C18:3) | (C18:3) |
| PC40 | 1-α-linolenoyl-2-oleoyl-sn-glycero-3-phosphocholine | (C18:3) | (C18:1) |
| PC41 | 1-α-linolenoyl-2-stearoyl-sn-glycero-3-phosphocholine | (C18:3) | (C18:0) |
| PC42 | 1-α-linolenoyl-2-arachidonoyl-sn-glycero-3-phosphocholine | (C18:3) | (C20:0) |
| PC43 | 1-α-linolenoyl-2-osbondoyl-sn-glycero-3-phosphocholine | (C18:3) | (C22:5) |
| PC44 | 1-oleoyl-2-palmitoleoyl-sn-glycero-3-phosphocholine | (C18:1) | (C16:1) |
| PC45 | 1-oleoyl-2-palmitoyl-sn-glycero-3-phosphocholine | (C18:1) | (C16:0) |
| PC46 | 1-oleoyl-2-α-linolenoyl-sn-glycero-3-phosphocholine | (C18:1) | (C18:3) |
| PC47 | 1-oleoyl-2-stearoyl-sn-glycero-3-phosphocholine | (C18:1) | (C18:0) |
| PC48 | 1-oleoyl-2-osbondoyl-sn-glycero-3-phosphocholine | (C18:1) | (C22:5) |
| PC49 | 1-stearoyl-2-palmitoleoyl-sn-glycero-3-phosphocholine | (C18:0) | (C16:1) |
| PC50 | 1-stearoyl-2-palmitoyl-sn-glycero-3-phosphocholine | (C18:0) | (C16:0) |
| PC51 | 1-stearoyl-2-α-linolenoyl-sn-glycero-3-phosphocholine | (C18:0) | (C18:3) |
| PC52 | 1,2-distearoyl-sn-glycero-3-phosphocholine | (C18:0) | (C18:0) |
| PC53 | 1-stearoyl-2-docosahexaenoyl-sn-glycero-3-phosphocholine | (C18:0) | (C20:6) |
| PC54 | 1-stearoyl-2-osbondoyl-sn-glycero-3-phosphocholine | (C18:0) | (C22:5) |
| PC55 | 1-arachidonoyl-2-palmitoleoyl-sn-glycero-3-phosphocholine | (C20:0) | (C16:1) |
| PC56 | 1-arachidonoyl-2-palmitoyl-sn-glycero-3-phosphocholine | (C20:0) | (C16:0) |
| PC57 | 1-arachidonoyl-2-linoleoyl-sn-glycero-3-phosphocholine | (C20:0) | (C18:2) |
| PC58 | 1-arachidonoyl-2-α-linolenoyl-sn-glycero-3-phosphocholine | (C20:0) | (C18:3) |
| PC59 | 1-arachidonoyl-2-oleoyl-sn-glycero-3-phosphocholine | (C20:0) | (C18:1) |
| PC60 | 1-arachidonoyl-2-stearoyl-sn-glycero-3-phosphocholine | (C20:0) | (C18:0) |
| PC61 | 1,2-diarachidonoyl-sn-glycero-3-phosphocholine | (C20:0) | (C20:0) |
| PC62 | 1-arachidonoyl-2-docosahexaenoyl-sn-glycero-3-phosphocholine | (C20:0) | (C20:6) |

TABLE 2-continued

| Compound | Name | R₁ | R₂ |
|---|---|---|---|
| PC63 | 1-arachidonoyl-2-osbondoyl-sn-glycero-3-phosphocholine | (C20:0) | (C22:5) |
| PC64 | 1-docosahexaenoyl-2-palmitoleoyl-sn-glycero-3-phosphocholine | (C20:6) | (C16:1) |
| PC65 | 1-docosahexaenoyl-2-palmitoyl-sn-glycero-3-phosphocholine | (C20:6) | (C16:0) |
| PC66 | 1-docosahexaenoyl-2-linoleoyl-sn-glycero-3-phosphocholine | (C20:6) | (C18:2) |
| PC67 | 1-docosahexaenoyl-2-α-linolenoyl-sn-glycero-3-phosphocholine | (C20:6) | (C18:3) |
| PC68 | 1-docosahexaenoyl-2-oleoyl-sn-glycero-3-phosphocholine | (C20:6) | (C18:1) |
| PC69 | 1-docosahexaenoyl-2-stearoyl-sn-glycero-3-phosphocholine | (C20:6) | (C18:0) |
| PC70 | 1-docosahexaenoyl-2-arachidonoyl-sn-glycero-3-phosphocholine | (C20:6) | (C20:0) |
| PC71 | 1,2-didocosahexaenoyl-sn-glycero-3-phosphocholine | (C20:6) | (C20:6) |
| PC72 | 1-docosahexaenoyl-2-docosahexaenoyl-sn-glycero-3-phosphocholine | (C20:6) | (C20:6) |
| PC73 | 1-docosahexaenoyl-2-osbondoyl-sn-glycero-3-phosphocholine | (C20:6) | (C22:5) |
| PC74 | 1-osbondoyl-2-palmitoleoyl-sn-glycero-3-phosphocholine | (C22:5) | (C16:1) |
| PC75 | 1-osbondoyl-2-palmitoyl-sn-glycero-3-phosphocholine | (C22:5) | (C16:0) |
| PC76 | 1-osbondoyl-2-linoleoyl-sn-glycero-3-phosphocholine | (C22:5) | (C18:2) |
| PC77 | 1-osbondoyl-2-α-linolenoyl-sn-glycero-3-phosphocholine | (C22:5) | (C18:3) |
| PC78 | 1-osbondoyl-2-oleoyl-sn-glycero-3-phosphocholine | (C22:5) | (C18:1) |
| PC79 | 1-osbondoyl-2-stearoyl-sn-glycero-3-phosphocholine | (C22:5) | (C18:0) |
| PC80 | 1-osbondoyl-2-arachidonoyl-sn-glycero-3-phosphocholine | (C22:5) | (C20:0) |
| PC81 | 1-osbondoyl-2-docosahexaenoyl-sn-glycero-3-phosphocholine | (C22:5) | (C20:6) |
| PC82 | 1,2-diosbondoyl-sn-glycero-3-phosphocholine | (C22:5) | (C22:5) |
| PC83 | 1-eicosapentaenoyl-2-palmitoleoyl-sn-glycero-3-phosphocholine | (C20:5) | (C16:1) |
| PC84 | 1-eicosapentaenoyl-2-palmitoyl-sn-glycero-3-phosphocholine | (C20:5) | (C16:0) |
| PC85 | 1-eicosapentaenoyl-2-linoleoyl-sn-glycero-3-phosphocholine | (C20:5) | (C18:2) |
| PC86 | 1-eicosapentaenoyl-2-α-linolenoyl-sn-glycero-3-phosphocholine | (C20:5) | (C18:3) |
| PC87 | 1-eicosapentaenoyl-2-oleoyl-sn-glycero-3-phosphocholine | (C20:5) | (C18:1) |
| PC88 | 1-eicosapentaenoyl-2-stearoyl-sn-glycero-3-phosphocholine | (C20:5) | (C18:0) |
| PC89 | 1-eicosapentaenoyl-2-arachidonoyl-sn-glycero-3-phosphocholine | (C20:5) | (C20:0) |
| PC90 | 1-eicosapentaenoyl-2-docosahexaenoyl-sn-glycero-3-phosphocholine | (C20:5) | (C20:6) |
| PC91 | 1,2-dieicosapentaenoyl-sn-glycero-3-phosphocholine | (C20:5) | (C20:5) |
| PC92 | 1-eicosapentaenoyl-2-osbondoyl-sn-glycero-3-phosphocholine | (C20:5) | (C22:5) |
| PC93 | 1-eicosapentaenoyl-2-clupanodonoyl-sn-glycero-3-phosphocholine | (C20:5) | (C22:5) |
| PC94 | 1-palmitoyl-2-eicosapentaenoyl-sn-glycero-3-phosphocholine | (C16:0) | (C20:5) |
| PC95 | 1-palmitoyl-2-clupanodonoyl-sn-glycero-3-phosphocholine | (C16:0) | (C22:5) |
| PC96 | 1-linoleoyl-2-eicosapentaenoyl-sn-glycero-3-phosphocholine | (C18:2) | (C20:5) |
| PC97 | 1-linoleoyl-2-clupanodonoyl-sn-glycero-3-phosphocholine | (C18:2) | (C22:5) |
| PC98 | 1-α-linolenoyl-2-eicosapentaenoyl-sn-glycero-3-phosphocholine | (C18:3) | (C20:5) |
| PC99 | 1-α-linolenoyl-2-clupanodonoyl-sn-glycero-3-phosphocholine | (C18:3) | (C22:5) |
| PC100 | 1-oleoyl-2-eicosapentaenoyl-sn-glycero-3-phosphocholine | (C18:1) | (C20:5) |

TABLE 2-continued

| Compound | Name | R₁ | R₂ |
|---|---|---|---|
| PC101 | 1-oleoyl-2-clupanodonoyl-sn-glycero-3-phosphocholine | (C18:1) | (C22:5) |
| PC102 | 1-stearoyl-2-eicosapentaenoyl-sn-glycero-3-phosphocholine | (C18:0) | (C20:5) |
| PC103 | 1-stearoyl-2-clupanodonoyl-sn-glycero-3-phosphocholine | (C18:0) | (C22:5) |
| PC104 | 1-arachidonoyl-2-eicosapentaenoyl-sn-glycero-3-phosphocholine | (C20:0) | (C20:5) |
| PC105 | 1-arachidonoyl-2-clupanodonoyl-sn-glycero-3-phosphocholine | (C20:0) | (C22:5) |
| PC106 | 1-docosahexaenoyl-2-eicosapentaenoyl-sn-glycero-3-phosphocholine | (C20:6) | (C20:5) |
| PC107 | 1,2-diclupanodonoyl-sn-glycero-3-phosphocholine | (C22:5) | (C22:5) |
| PC108 | 1-palmitoleoyl-2-eicosapentaenoyl-sn-glycero-3-phosphocholine | (C16:1) | (C20:5) |
| PC109 | 1-palmitoleoyl-2-clupanodonoyl-sn-glycero-3-phosphocholine | (C16:1) | (C22:5) |
| PC110 | 1-docosahexaenoyl-2-clupanodonoyl-sn-glycero-3-phosphocholine | (C20:6) | (C22:5) |
| PC111 | 1-osbondoyl-2-eicosapentaenoyl-sn-glycero-3-phosphocholine | (C22:5) | (C20:5) |
| PC112 | 1-osbondoyl-2-clupanodonoyl-sn-glycero-3-phosphocholine | (C22:5) | (C22:5) |
| PC113 | 1-clupanodonoyl-2-eicosapentaenoyl-sn-glycero-3-phosphocholine | (C22:5) | (C20:5) |
| PC114 | 1-palmitoleoyl-2-linoleoyl-sn-glycero-3-phosphocholine | (C16:1) | (C18:2) |
| PC115 | 1-palmitoyl-2-α-linolenoyl-sn-glycero-3-phosphocholine | (C16:0) | (C18:3) |
| PC116 | 1-palmitoyl-2-arachidonoyl-sn-glycero-3-phosphocholine | (C16:0) | (C20:0) |
| PC117 | 1,2-dilinoleoyl-sn-glycero-3-phosphocholine | (C18:2) | (C18:2) |
| PC118 | 1-palmitoyl-2-docosahexaenoyl-sn-glycero-3-phosphocholine | (C16:0) | (C20:6) |
| PC119 | 1-α-linolenoyl-2-docosahexaenoyl-sn-glycero-3-phosphocholine | (C18:3) | (C20:6) |
| PC120 | 1-palmitoleoyl-2-oleoyl-sn-glycero-3-phosphocholine | (C16:1) | (C18:1) |
| PC121 | 1-palmitoyl-2-linoleoyl-sn-glycero-3-phosphocholine | (C16:0) | (C18:2) |
| PC122 | 1-palmitoleoyl-2-docosahexaenoyl-sn-glycero-3-phosphocholine | (C16:1) | (C20:6) |
| PC123 | 1-palmitoyl-2-osbondoyl-sn-glycero-3-phosphocholine | (C16:0) | (C22:5) |
| PC124 | 1-oleoyl-2-arachidonoyl-sn-glycero-3-phosphocholine | (C18:1) | (C20:0) |
| PC125 | 1-oleoyl-2-linoleoyl-sn-glycero-3-phosphocholine | (C18:1) | (C18:2) |
| PC126 | 1-stearoyl-2-arachidonoyl-sn-glycero-3-phosphocholine | (C18:0) | (C20:0) |
| PC127 | 1-palmitoyl-2-oleoyl-sn-glycero-3-phosphocholine | (C16:0) | (C18:1) |
| PC128 | 1-oleoyl-2-docosahexaenoyl-sn-glycero-3-phosphocholine | (C18:1) | (C20:6) |
| PC129 | 1,2-dioleoyl-sn-glycero-3-phosphocholine | (C18:1) | (C18:1) |
| PC130 | 1-stearoyl-2-linoleoyl-sn-glycero-3-phosphocholine | (C18:0) | (C18:2) |
| PC131 | 1-stearoyl-2-oleoyl-sn-glycero-3-phosphocholine | (C18:0) | (C18:1) |
| PC132 | 1-tetradecanoyl-2-palmitoleoyl-sn-glycero-3-phosphocholine | (C14:0) | (C16:1) |
| PC133 | 1-tetradecanoyl-2-palmitoyl-sn-glycero-3-phosphocholine | (C14:0) | (C16:0) |
| PC134 | 1-tetradecanoyl-2-linoleoyl-sn-glycero-3-phosphocholine | (C14:0) | (C18:2) |
| PC135 | 1-tetradecanoyl-2-α-linolenoyl-sn-glycero-3-phosphocholine | (C14:0) | (C18:3) |
| PC136 | 1-tetradecanoyl-2-oleoyl-sn-glycero-3-phosphocholine | (C14:0) | (C18:1) |
| PC137 | 1-tetradecanoyl-2-stearoyl-sn-glycero-3-phosphocholine | (C14:0) | (C18:0) |
| PC138 | 1-tetradecanoyl-2-arachidonoyl-sn-glycero-3-phosphocholine | (C14:0) | (C20:0) |
| PC139 | 1-tetradecanoyl-2-docosahexaenoyl-sn-glycero-3-phosphocholine | (C14:0) | (C20:6) |

TABLE 2-continued

| Compound | Name | R₁ | R₂ |
|---|---|---|---|
| PC140 | 1-tetradecanoyl-2-docosahexaenoyl-sn-glycero-3-phosphocholine | (C14:0) | (C20:6) |
| PC141 | 1-tetradecanoyl-2-eicosapentaenoyl-sn-glycero-3-phosphocholine | (C14:0) | (C20:5) |
| PC142 | 1-tetradecanoyl-2-arachidonoyl-sn-glycero-3-phosphocholine | (C14:0) | (C20:0) |
| PC143 | 1-tetradecanoyl-2-eicosapentaenoyl-sn-glycero-3-phosphocholine | (C14:0) | (C20:5) |
| PC144 | 1-tetradecanoyl-2-osbondoyl-sn-glycero-3-phosphocholine | (C14:0) | (C22:5) |
| PC145 | 1-tetradecanoyl-2-clupanodonoyl-sn-glycero-3-phosphocholine | (C14:0) | (C22:5) |
| PC146 | 1-tetradecanoyl-2-hydroxy-sn-glycero-3-phosphocholine | (C14:0) | H |
| PC147 | 1-palmitoleoyl-2-tetradecanoyl-sn-glycero-3-phosphocholine | (C16:1) | (C14:0) |
| PC148 | 1-palmitoyl-2-tetradecanoyl-sn-glycero-3-phosphocholine | (C16:0) | (C14:0) |
| PC149 | 1-linoleoyl-2-tetradecanoyl-sn-glycero-3-phosphocholine | (C18:2) | (C14:0) |
| PC150 | 1-α-linolenoyl-2-tetradecanoyl-sn-glycero-3-phosphocholine | (C18:3) | (C14:0) |
| PC151 | 1-oleoyl-2-tetradecanoyl-sn-glycero-3-phosphocholine | (C18:1) | (C14:0) |
| PC152 | 1-stearoyl-2-tetradecanoyl-sn-glycero-3-phosphocholine | (C18:0) | (C14:0) |
| PC153 | 1-arachidonoyl-2-tetradecanoyl-sn-glycero-3-phosphocholine | (C20:0) | (C14:0) |
| PC154 | 1-docosahexaenoyl-2-tetradecanoyl-sn-glycero-3-phosphocholine | (C20:6) | (C14:0) |
| PC155 | 1-eicosapentaenoyl-2-tetradecanoyl-sn-glycero-3-phosphocholine | (C20:5) | (C14:0) |
| PC156 | 1-arachidonoyl-2-tetradecanoyl-sn-glycero-3-phosphocholine | (C20:0) | (C14:0) |
| PC157 | 1-eicosapentaenoyl-2-tetradecanoyl-sn-glycero-3-phosphocholine | (C20:5) | (C14:0) |
| PC158 | 1-osbondoyl-2-tetradecanoyl-sn-glycero-3-phosphocholine | (C22:5) | (C14:0) |
| PC159 | 1-clupanodonoyl-2-tetradecanoyl-sn-glycero-3-phosphocholine | (C22:5) | (C14:0) |
| PC160 | 1-hydroxy-2-tetradecanoyl-sn-glycero-3-phosphocholine | H | (C14:0) |
| PC161 | 1-hydroxy-2-palmitoleoyl-sn-glycero-3-phosphocholine | H | (C16:1) |
| PC162 | 1-hydroxy-2-palmitoyl-sn-glycero-3-phosphocholine | H | (C16:0) |
| PC163 | 1-hydroxy-2-linoleoyl-sn-glycero-3-phosphocholine | H | (C18:2) |
| PC164 | 1-hydroxy-2-α-linolenoyl-sn-glycero-3-phosphocholine | H | (C18:3) |
| PC165 | 1-hydroxy-2-oleoyl-sn-glycero-3-phosphocholine | H | (C18:1) |
| PC166 | 1-hydroxy-2-stearoyl-sn-glycero-3-phosphocholine | H | (C18:0) |
| PC167 | 1-hydroxy-2-arachidonoyl-sn-glycero-3-phosphocholine | H | (C20:0) |
| PC168 | 1-hydroxy-2-docosahexaenoyl-sn-glycero-3-phosphocholine | H | (C20:6) |
| PC169 | 1-hydroxy-2-docosahexaenoyl-sn-glycero-3-phosphocholine | H | (C20:6) |
| PC170 | 1-hydroxy-2-eicosapentaenoyl-sn-glycero-3-phosphocholine | H | (C20:5) |
| PC171 | 1-hydroxy-2-arachidonoyl-sn-glycero-3-phosphocholine | H | (C20:0) |
| PC172 | 1-hydroxy-2-eicosapentaenoyl-sn-glycero-3-phosphocholine | H | (C20:5) |
| PC173 | 1-hydroxy-2-osbondoyl-sn-glycero-3-phosphocholine | H | (C22:5) |
| PC174 | 1-palmitoleoyl-2-hydroxy-sn-glycero-3-phosphocholine | (C16:1) | H |
| PC175 | 1-palmitoyl-2-hydroxy-sn-glycero-3-phosphocholine | (C16:0) | H |
| PC176 | 1-linoleoyl-2-hydroxy-sn-glycero-3-phosphocholine | (C18:2) | H |
| PC177 | 1-α-linolenoyl-2-hydroxy-sn-glycero-3-phosphocholine | (C18:3) | H |
| PC178 | 1-oleoyl-2-hydroxy-sn-glycero-3-phosphocholine | (C18:1) | H |
| PC179 | 1-stearoyl-2-hydroxy-sn-glycero-3-phosphocholine | (C18:0) | H |

TABLE 2-continued

| Compound | Name | $R_1$ | $R_2$ |
|---|---|---|---|
| PC180 | 1-arachidonoyl-2-hydroxy-sn-glycero-3-phosphocholine | (C20:0) | H |
| PC181 | 1-docosahexaenoyl-2-hydroxy-sn-glycero-3-phosphocholine | (C20:6) | H |
| PC182 | 1-docosahexaenoyl-2-hydroxy-sn-glycero-3-phosphocholine | (C20:6) | H |
| PC183 | 1-eicosapentaenoyl-2-hydroxy-sn-glycero-3-phosphocholine | (C20:5) | H |
| PC184 | 1-arachidonoyl-2-hydroxy-sn-glycero-3-phosphocholine | (C20:0) | H |
| PC185 | 1-eicosapentaenoyl-2-hydroxy-sn-glycero-3-phosphocholine | (C20:5) | H |
| PC186 | 1-osbondoyl-2-hydroxy-sn-glycero-3-phosphocholine | (C22:5) | H |

It will be understood that in the event of any inconsistency between the fatty acid and compound name both the compound and the sphingomyelin comprising the fatty acid are disclosed in Table 2.

In various embodiments, any of the phosphatidylcholines listed in Table 2 may comprise individually from about 1-100% (w/w) (e.g., 1-10% (w/w) or 10-20% (w/w) or 20-30% or 30-40% (w/w) or 40-50% (w/w) or 50-60% (w/w) or 60-70% (w/w) or 70-80% (w/w) or 80-90% (w/w) or 90-100% (w/w)) of the phospholipid component (or the phosphatidylcholine component) of the pharmaceutical compositions. In some embodiments, phosphotidylcholine component comprises between about 1-25% PC7 by weight of the phospholipid component and/or between about 1-25% PC8 by weight of the phospholipid component and/or between about 1-25% PC14 by weight of the phospholipid component and/or between about 1-25% PC16 by weight of the phospholipid component and/or between about 1-25%. In some embodiments, the phospholipid component (or the phosphotidylcholine component) of the pharmaceutical compositions of the invention may be free of any of the phosphotidylcholine compounds (PC1-PC186) listed in Table 2, or may be substantially free of such compounds, by which is meant that a given phosphatidylcholine is present in such small amounts as to not have a benefit in the treatment of cancer at the given level and in any event will be less than 2.5% (w/w) or less than 1% (w/w) or less than 0.5% (w/w) or less than 0.1% (w/w) based on the total weight of the phospholipid component (or of the phosphatidylcholine component).

The mixtures of compounds suitable for present invention may comprise highly unsaturated fatty acid components in the PCs. In some embodiments, PC molecules comprising at least five or at least six unsaturated bonds will constitute from about 10-100% (w/w) of the lipid components.

In some embodiments of the invention, the pharmaceutical composition may comprise a hen egg yolk extract, comprising a phosphatidylcholine component; wherein at least 50% (w/w) of said phosphatidylcholine component is a compound having the structure of formula I(a):

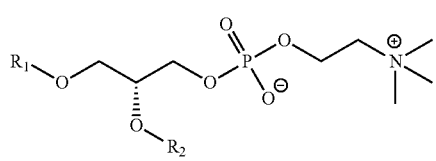

I(a)

wherein $R_1$ is selected from the group consisting of palmitoyl (C16:0), (C18:2) (e.g., linoleoyl), (C18:3) (e.g., α-linolenoyl), (C16:1) (e.g., palmitoleoyl), (C18:1) (e.g., oleoyl), and stearoyl (C18:0) radicals; and $R_2$ is selected from an acyl group corresponding to a naturally occurring fatty acid. In other embodiments, $R_1$ is selected from an acyl group corresponding to a naturally occurring fatty acid and $R_2$ is selected from (C18:2) (e.g., linoleoyl), (C18:3) (e.g., α-linolenoyl), (C20:4) (e.g., arachidonoyl), (C18:2) (e.g., linoleoyl), (C22:6) (e.g., docosahexaenoyl), (C18:1) (e.g., oleoyl), (C22:5) (e.g., docosapentaenoyl), (C22:5) (e.g. clupanodonoyl), or (C18:5) (e.g., eicosapentaenoyl) radicals.

In other embodiments of the invention the pharmaceutical composition may comprise a hen egg yolk extract comprising a phosphatidylcholine component; wherein at least 50% of said phosphatidylcholine component is selected from the group consisting of:
1-palmitoyl-2-linoleoyl-sn-glycero-3-phosphocholine,
1-palmitoyl-2-α-linolenoyl-sn-glycero-3-phosphocholine,
1-palmitoyl-2-arachidonoyl-sn-glycero-3-phosphocholine,
1-linoleoyl-2-linoleoyl-sn-glycero-3-phosphocholine,
1-palmitoyl-2-docosahexaenoyl-sn-glycero-3-phosphocholine,
1-palmitoleoyl-2-oleoyl-sn-glycero-3-phosphocholine,
1-palmitoleoyl-2-linoleoyl-sn-glycero-3-phosphocholine,
1-oleoyl-2-linoleoyl-sn-glycero-3-phosphocholine,
1-palmitoyl-2-eicosatrienoyl-sn-glycero-3-phosphocholine,
1-palmitoyl-2-clupanodonoyl-sn-glycero-3-phosphocholine,
1-stearoyl-2-docosahexaenoyl-sn-glycero-3-phosphocholine,
1-stearoyl-2-linoleoyl-sn-glycero-3-phosphocholine,
1-oleoyl-2-oleoyl-sn-glycero-3-phosphocholine,
1-stearoyl-2-oleoyl-sn-glycero-3-phosphocholine,
1-palmitoyl-2-osbondoyl-sn-glycero-3-phosphocholine,
1-oleoyl-2-arachidonoyl-sn-glycero-3-phosphocholine,
1-oleoyl-2-linoleoyl-sn-glycero-3-phosphocholine,
1-stearoyl-2-arachidonoyl-sn-glycero-3-phosphocholine,
1-palmitoyl-2-oleoyl-sn-glycero-3-phosphocholine,
and pharmaceutically acceptable salts thereof. In some embodiments, the pharmaceutical composition may comprise a hen egg yolk extract comprising a phosphatidylcholine component; wherein at least 50% of said phosphatidylcholine component is selected from the group consisting of:
1-palmitoyl-2-linoleoyl-sn-glycero-3-phosphocholine,
1-palmitoleoyl-2-oleoyl-sn-glycero-3-phosphocholine,
1-palmitoyl-2-oleoyl-sn-glycero-3-phosphocholine,
1-stearoyl-2-linoleoyl-sn-glycero-3-phosphocholine, 1,2- dioleoyl-sn-glycero-phosphocholine, 1-hydroxy-2-oleoyl-sn-glycero-3-phosphocholine, and pharmaceutically acceptable salts thereof.

In some embodiments of the invention, the mixture comprises sphingomyelin (SPH) compounds. Sphingomyelins of the invention may have the structure of formula II(a)

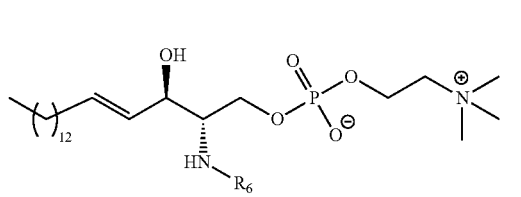

II(a)

where $R_6$ can be any monovalent radical, but is typically an acyl group comprising an aliphatic hydrocarbon chains, and more typically is the acyl portion groups of the corresponding naturally occurring fatty acids. The acyl groups generally have the form —(C=O)—R, where R is a $C_2$-$C_{30}$ aliphatic alkyl or alkenyl chain. These acyl groups correspond to the acyl portion of naturally occurring fatty acids such as ω-3 and ω-6 fatty acids and given in Table 1. In some embodiments of the invention, the mixture of bioactive lipids comprises one or more PC compounds and/or one or more SPH compounds. In some embodiments, the hen egg yolk extract is enriched with one or more PC compounds and/or one or more SPH compounds. In other embodiments, the hen egg yolk extract is enriched with one or more SPH compounds. In other embodiments, the hen egg yolk extract is enriched with one or more PC compounds and one or more SPH compounds.

In various embodiments, the pharmaceutical composition may comprise an egg yolk extract, wherein the egg yolk extract is enriched in one or more PCs selected from the group of compounds having the structure of formula I(a):

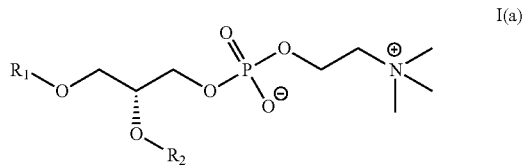

I(a)

where $R_1$ is selected from the group consisting of hydrogen, palmitoyl (C16:0), linoleoyl (C18:2), α-linolenoyl (C18:3), palmitoleoyl (C16:1), oleoyl (C18:1), and stearoyl (C18:0) radicals; and $R_2$ is selected from the group consisting of hydrogen, linoleoyl (C18:2), α-linolenoyl (C18:3), arachidonoyl (C20:4), linoleoyl (C18:2), docosahexaenoyl (C22:6), oleoyl (C18:1), osbondoyl (C22:5), and eicosapentaenoyl (C18:5) radicals; and/or wherein the egg yolk extract may be enriched in one or more sphingomyelins selected from the group of compounds having the structure:

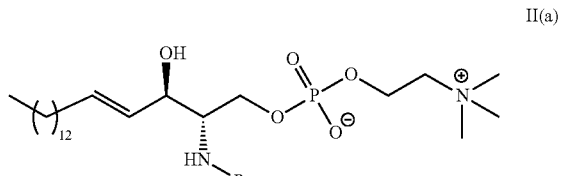

II(a)

where $R_6$ is palmitoyl, stearoyl, or oleoyl, or pharmaceutically acceptable salts thereof. In some embodiments, the pharmaceutical composition may comprise a hen egg yolk extract, wherein the hen egg yolk extract may comprise a phosphatidylcholine component and a sphingomyelin component; wherein at least 50% of said phosphatidylcholine component may be selected from the group consisting of:

1-palmitoyl-2-linoleoyl-sn-glycero-3-phosphocholine,
1-palmitoyl-2-α-linolenoyl-sn-glycero-3-phosphocholine,
1-palmitoyl-2-arachidonoyl-sn-glycero-3-phosphocholine,
1-linoleoyl-2-linoleoyl-sn-glycero-3-phosphocholine,
1-palmitoyl-2-docosahexaenoyl-sn-glycero-3-phosphocholine,
1-palmitoleoyl-2-oleoyl-sn-glycero-3-phosphocholine,
1-palmitoyl-2-osbondoyl-sn-glycero-3-phosphocholine,
1-oleoyl-2-arachidonoyl-sn-glycero-3-phosphocholine,
1-palmitoleoyl-2-linoleoyl-sn-glycero-3-phosphocholine,
1-palmitoyl-2-clupanodonoyl-sn-glycero-3-phosphocholine,
1-oleoyl-2-linolenoyl-sn-glycero-3-phosphocholine,
1-palmitoyl-2-eicosatrienoyl-sn-glycero-3-phosphocholine,
1-stearoyl-2-docosahexaenoyl-sn-glycero-3-phosphocholine,
1-stearoyl-2-linolenoyl-sn-glycero-3-phosphocholine,
1-oleoyl-2-oleoyl-sn-glycero-3-phosphocholine,
1-stearoyl-2-oleoyl-sn-glycero-3-phosphocholine,
1-oleoyl-2-linoleoyl-sn-glycero-3-phosphocholine,
1-stearoyl-2-arachidonoyl-sn-glycero-3-phosphocholine,
1-palmitoyl-2-oleoyl-sn-glycero-3-phosphocholine, and
pharmaceutically acceptable salts thereof.

In some embodiments, the sphingomyelin component is between about 0.01 and about 50% by weight of the phospholipid composition (e.g., about 0.1 to about 30% or about 1% to about 20% or about 1% to about 10%, etc.). In some embodiments, at least 50% (w/w) of the sphingomyelin component may comprise one or more sphingomyelins selected from the group of N-palmitoyl-D-erythro-sphingosylphosphorylcholine, N-stearoyl-D-erythro-sphingosylphosphorylcholine, and N-oleoyl-D-erythro-sphingosylphosphorylcholine. In some embodiments, the sphingomyelin at least 50% (w/w) of the sphingomyelein component comprises N-palmitoyl-D-erythro-sphingosylphosphorylcholine. In some embodiments, the sphingomyelin component consists or consists essentially of N-palmitoyl-D-erythro-sphingosylphosphorylcholine.

Table 3 provides the compound names for representatives of sphingomyelins (SPH) comprising a (C18:1) backbone and the fatty acid residue of each sphingomyelin which may be present in the egg yolk extract. In some embodiments, the SPH has a different fatty acid backbone (e.g., those fatty acids listed in Table 1). These SPH compounds may be present individually or in combination with one another, or in combination with one or more PC compounds, e.g., as described in Table 2.

TABLE 3

| Compound | Compound Name | Fatty Acid |
| --- | --- | --- |
| SPH1 | N-palmitoyl-D-erythro-sphingosylphosphorylcholine | (C16:0) |
| SPH2 | N-stearoyl-D-erythro-sphingosylphosphorylcholine | (C18:0) |
| SPH3 | N-oleoyl-D-erythro-sphingosylphosphorylcholine | (C18:1) |
| SPH4 | N-palmitoleoyl-D-erythro-sphingosylphosphorylcholine | (C16:1) |
| SPH5 | N-linoleoyl-D-erythro-sphingosylphosphorylcholine | (C18:2) |
| SPH6 | N-α-linolenoyl-D-erythro-sphingosylphosphorylcholine | (C18:3) |
| SPH7 | N-arachidonoyl-D-erythro-sphingosylphosphorylcholine | (C20:4) |
| SPH8 | N-docosahexaenoyl-D-erythro-sphingosylphosphorylcholine | (C22:6) |
| SPH9 | N-eicosapentaenoyl-D-erythro-sphingosylphosphorylcholine | (C20:5) |
| SPH10 | N-osbondoyl-D-erythro-sphingosylphosphorylcholine | (C22:5) |
| SPH11 | N-clupanodonoyl-D-erythro-sphingosylphosphorylcholine | (C22:5) |
| SPH12 | N-tetradecanoyl-D-erythro-sphingosylphosphorylcholine | (C14:0) |
| SPH13 | N-heptadecanoyl-D-erythro-sphingosylphosphorylcholine | (C17:0) |
| SPH14 | N-nonadecanoyl-D-erythro-sphingosylphosphorylcholine | (C19:0) |
| SPH15 | N-eicosanoyl-D-erythro-sphingosylphosphorylcholine | (C20:0) |
| SPH16 | N-docosanoyl-D-erythro-sphingosylphosphorylcholine | (C22:0) |
| SPH17 | N-docosenoyl-D-erythro-sphingosylphosphorylcholine | (C22:1) |
| SPH18 | N-heneicosanoyl-D-erythro-sphingosylphosphorylcholine | (C23:0) |
| SPH19 | N-tetracosadienoic-D-erythro-sphingosylphosphorylcholine | (C24:2) |
| SPH20 | N-tetracosenoyl-D-erythro-sphingosylphosphorylcholine | (C24:1) |
| SPH21 | N-tetracosanoyl-D-erythro-sphingosylphosphorylcholine | (C24:0) |

It will be understood that in the event of any inconsistency between the fatty acid and compound name both the compound and the sphingomyelin comprising the fatty acid are disclosed in Table 3. In some embodiments, any combination of sphingomyelins selected from SPH1, SPH2, and SPH12-SPH21 may be present in the egg yolk extract as disclosed in Hsu, F. et al., *J. Am. Soc. Mass. Spectrom.* 11 2000 (437-449) herein incorporated by reference in its entirety, particularly in reference to disclosure of egg yolk components.

In various embodiments, any of the sphingomyelins listed in Table 3 may comprise individually from about 1-100% (w/w) (e.g., 1-10% (w/w) or 10-20% (w/w) or 20-30% or 30-40% (w/w) or 40-50% (w/w) or 50-60% (w/w) or 60-70% (w/w) or 70-80% (w/w) or 80-90% (w/w) or 90-100% (w/w)) of the phospholipid component (or the sphingomyelin component) of the pharmaceutical compositions. In some embodiments, the sphingomyelin component comprises from about 0.01% to about 50% or about 0.1% to about 10% by weight of the phospholipid component (e.g., 0.1 to about 30, about 1% to about 5% by weight of the phospholipid component). In some embodiments, the phospholipid component (or the sphingomyelin component) of the pharmaceutical compositions of the invention may be free of any of sphingomyelin compounds (e.g. SPH1-SPH21 listed in Table 3), or may be substantially free of such compounds by which is meant that a given sphingomyelin is present in such small amounts as to not have a benefit in the treatment of cancer at the given level and in any event will be less than 2.5% (w/w) or less than 1% (w/w) or less than 0.5% (w/w) or less than 0.1% (w/w) based on the total weight of the phospholipid component (or of the sphingomyelin component).

In various embodiments, the pharmaceutical compositions may include one or more (e.g., two or more, three or more, four or more, etc.) phosphatidylcholines selected from the group consisting of PC1-PC186 (e.g., the group consisting of PC1-PC131) and/or one or more sphingomyelins (e.g., two or more, three or more, four or more, etc.) selected from the group consisting of SPH1-SPH11. In other embodiments, the pharmaceutical compositions may include one or more phosphatidylcholines selected from the group consisting of PC1-PC18 and/or one or more sphingomyelins selected from the group consisting of SPH1-SPH3. In other embodiments, the pharmaceutical compositions may include two or more (e.g, three or more, four or more, five or more, etc.) phosphatidylcholines independently selected from the group consisting of PC1-PC18. In other embodiments, the pharmaceutical compositions may include one or more phosphatidylcholines (e.g., two or more, three or more, four or more, etc.) and one or more sphingomyelins (e.g., two or more, three or more, four or more, etc.), where the one or more phosphatidylcholines are selected from group consisting of PC1-PC18 and the one or more sphingomyelins are selected from the group consisting of SPH1-SPH3. In some embodiments, the phosphatidylcholine component comprises PC7 and/or PC8 and/or PC14 and/or PC16 and/or PC17. In some embodiments, the sphingomyelin component comprises SPH1. IN some embodiments, the sphingomyelin component consists or consists essentially of SPH1.

In some embodiments, the pharmaceutical composition may include PC1 and one or more phosphatidylcholines selected from the group consisting of PC2-PC18. In some embodiments, the pharmaceutical composition may include PC2 and one or more phosphatidylcholines selected from the group consisting of PC1, and PC3-PC18. In some embodiments, the pharmaceutical composition may include PC3 and one or more phosphatidylcholines selected from the group consisting of PC1-PC2, and PC4-PC18. In some embodiments, the pharmaceutical composition may include PC4 and one or more phosphatidylcholines selected from the group consisting of PC1-PC3, and PC5-PC18. In some embodiments, the pharmaceutical composition may include PC5 and one or more phosphatidylcholines selected from the group consisting of PC1-PC4, and PC6-PC18. In some embodiments, the pharmaceutical composition may include PC6 and one or more phosphatidylcholines selected from the group consisting of PC1-PC5, and PC7-PC18. In some embodiments, the pharmaceutical composition may include PC7 and one or more phosphatidylcholines selected from the group consisting of PC1-PC6, and PC8-PC18. In some embodiments, the pharmaceutical composition may include PC8 and one or more phosphatidylcholines selected from the group consisting of PC1-PC7, and PC9-PC18. In some embodiments, the pharmaceutical composition may include PC9 and one or more phosphatidylcholines selected from the group consisting of PC1-PC8, and PC10-PC18. In some embodiments, the pharmaceutical composition may include PC10 and one or more phosphatidylcholines selected from the group consisting of PC1-PC9, and PC11-PC18. In some embodiments, the pharmaceutical composition may include PC11 and one or more phosphatidylcholines selected from the group consisting of PC1-PC10, and PC12-PC18. In some embodiments, the pharmaceutical composition may include PC12 and one or more phosphatidylcholines selected from the group consisting of PC1-PC11, and PC13-PC18. In some embodiments, the pharmaceutical composition may include PC13 and one or more phosphatidylcholines selected from the group consisting of PC1-PC12, and PC14-PC18. In some embodiments, the pharmaceutical composition may include PC14 and one or more phosphatidylcholines selected from the group consisting of PC1-PC13, and PC15-PC18. In some embodiments, the pharmaceutical composition may include PC15 and one or more phosphatidylcholines selected from the group consisting of PC1-PC14, and PC16-PC18. In some embodiments, the pharmaceutical composition may include PC16 and one or more phosphatidylcholines selected from the group consisting of PC1-PC15, and PC17-PC18. In some embodiments, the pharmaceutical composition may include PC17 and one or more phosphatidylcholines selected from the group consisting of PC1-PC16, and PC18. In some embodiments, the pharmaceutical composition may include PC18 and one or more phosphatidylcholines selected from the group consisting of PC1-PC17.

In some embodiments, the pharmaceutical composition may include SPH1 and one or more phosphatidylcholines selected from the group consisting of PC1-PC18. In some embodiments, the pharmaceutical composition may include SPH2 and one or more phosphatidylcholines selected from the group consisting of PC1-PC18. In some embodiments, the pharmaceutical composition may include SPH3 and one or more phosphatidylcholines selected from the group consisting of PC1-PC18.

In some implementations of the invention, the phospholipid mixtures are enriched in one or more phospholipids (e.g., phosphatidylcholines, sphingomyelins, lysophosphatidylcholines, etc.). By "enriched" is meant that the relative abundance of a given phospholipid in relation to any other phospholipids in the composition is increased compared to the relative abundance of the same phospholipid to the same other phospholipids in hen egg yolk (or in BAP(−) or in BAP(+) or any fraction thereof).

In various embodiments, the hen egg yolk may be enriched in one or more phosphatidylcholines selected from the group consisting of PC1-PC186 (e.g., the group consisting of PC1-PC131) and/or one or more sphingomyelins selected from the group consisting of SPH1-SPH11. In other embodiments, the hen egg yolk is enriched in one or more phosphatidylcholines selected from the group consisting of PC1-PC18 and/or one or more sphingomyelins selected from the group consisting of SPH1-SPH3. In other embodiments, the hen egg yolk is enriched in two or more phosphatidylcholines independently selected from the group consisting of PC1-PC18. In other embodiments, the hen egg yolk is enriched in one or more phosphatidylcholines and with one or more sphingomyelins, where the one or more phosphatidylcholines are selected from group consisting of PC1-PC18 and the one or more sphingomyelins are selected from the group consisting of SPH1-SPH3.

In some embodiments, the hen egg yolk extract is enriched in PC1 and one or more phosphatidylcholines selected from the group consisting of PC2-PC18. In some embodiments, the hen egg yolk extract is enriched in PC2 and one or more phosphatidylcholines selected from the group consisting of PC1, and PC3-PC18. In some embodiments, the hen egg yolk extract is enriched in PC3 and one or more phosphatidylcholines selected from the group consisting of PC1-PC2, and PC4-PC18. In some embodiments, the hen egg yolk extract is enriched in PC4 and one or more phosphatidylcholines selected from the group consisting of PC1-PC3, and PC5-PC18. In some embodiments, the hen egg yolk extract is enriched in PC5 and one or more phosphatidylcholines selected from the group consisting of PC1-PC4, and PC6-PC18. In some embodiments, the hen egg yolk extract is enriched in PC6 and one or more phosphatidylcholines selected from the group consisting of PC1-PC5, and PC7-PC18. In some embodiments, the hen egg yolk extract is enriched in PC7 and one or more phosphatidylcholines selected from the group consisting of PC1-PC6, and PC8-PC18. In some embodiments, the hen egg yolk extract is enriched in PC8 and one or more phosphatidylcholines selected from the group consisting of PC1-PC7, and PC9-PC18. In some embodiments, the hen egg yolk extract is enriched in PC9 and one or more phosphatidylcholines selected from the group consisting of PC1-PC8, and PC10-PC18. In some embodiments, the hen egg yolk extract is enriched in PC10 and one or more phosphatidylcholines selected from the group consisting of PC1-PC9, and PC11-PC18. In some embodiments, the hen egg yolk extract is enriched in PC11 and one or more phosphatidylcholines selected from the group consisting of PC1-PC10, and PC12-PC18. In some embodiments, the hen egg yolk extract is enriched in PC12 and one or more phosphatidylcholines selected from the group consisting of PC1-PC11, and PC13-PC18. In some embodiments, the hen egg yolk extract is enriched in PC13 and one or more phosphatidylcholines selected from the group consisting of PC1-PC12, and PC14-PC18. In some embodiments, the hen egg yolk extract is enriched in PC14 and one or more phosphatidylcholines selected from the group consisting of PC1-PC13, and PC15-PC18. In some embodiments, the hen egg yolk extract is enriched in PC15 and one or more phosphatidylcholines selected from the group consisting of PC1-PC14, and PC16-PC18. In some embodiments, the hen egg yolk extract is enriched in PC16 and one or more phosphatidylcholines selected from the group consisting of PC1-PC15, and PC17-PC18. In some embodiments, the hen egg yolk extract is enriched in PC17 and one or more phosphatidylcholines selected from the group consisting of PC1-PC16, and PC18. In some embodiments, the hen egg yolk extract is enriched in PC18 and one or more phosphatidylcholines selected from the group consisting of PC1-PC17.

In some embodiments, the hen egg yolk extract is enriched in SPH1 and one or more phosphatidylcholines selected from the group consisting of PC1-PC18. In some embodiments, the hen egg yolk extract is enriched in SPH2 and one or more phosphatidylcholines selected from the group consisting of PC1-PC18. In some embodiments, the hen egg yolk extract is enriched in SPH3 and one or more phosphatidylcholines selected from the group consisting of PC1-PC18.

Specific phospholipids according to the invention are illustrated below.

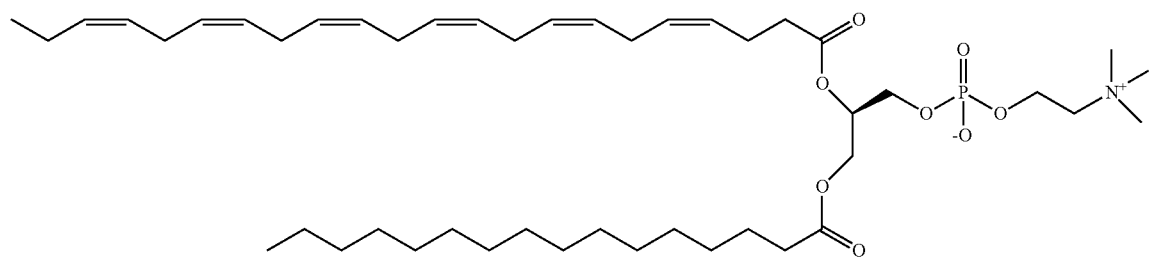
(R)-2-(((4Z,7Z,10Z,13Z,16Z,19Z)-docosa-4,7,10,13,
16,19-hexaenoyl)oxy)-3-(palmitoyloxy)propyl (2-
(trimethylammonio)ethyl) phosphate ("MPC1")
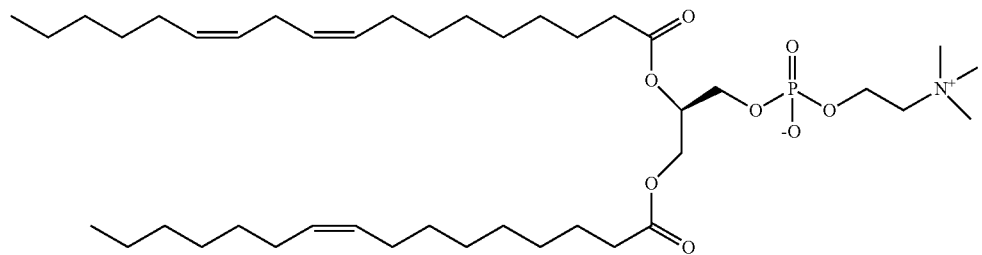
(R)-2-(((9Z,12Z)-octadeca-9,12-dienoyl)oxy)-3-((Z)-
hexadec-9-enoyl)oxy)propyl (2-(trimethylammonio)
ethyl) phosphate ("MPC2")
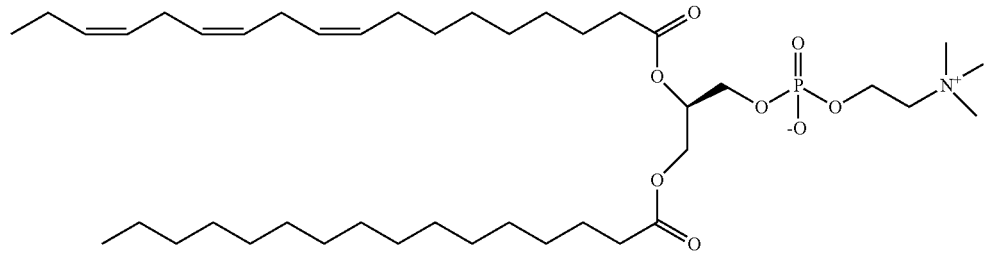
(R)-2((9Z,12Z,15Z)-octadeca-9,12,15-trienoyl)oxy)-
3-((Z)-hexadec-9-enoyl)oxy)propyl (2-(trimethylam-
monio)ethyl) phosphate ("MPC3")
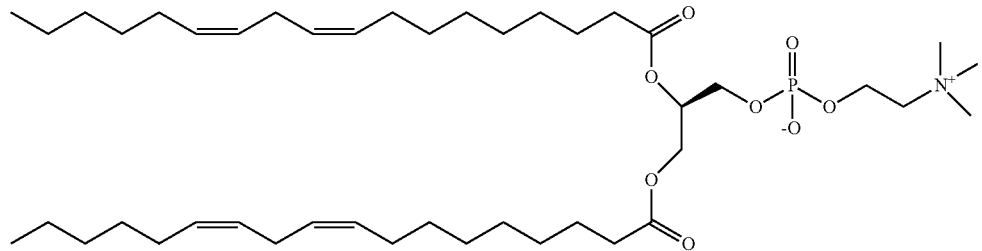

(R)-2,3-bis(((9Z,12Z)-octadeca-9,12-dienoyl)oxy)
propyl (2-(trimethylammonio)ethyl) phosphate
("MPC4")
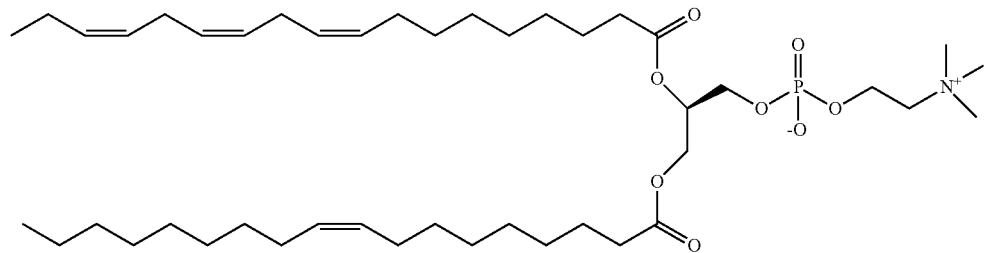
(R)-2-(((9Z,12Z,15Z)-octadeca-9,12,15-trienoyl)
oxy)-3-(oleoyloxy)propyl (2-(trimethylammonio)
ethyl) phosphate ("MPC5")
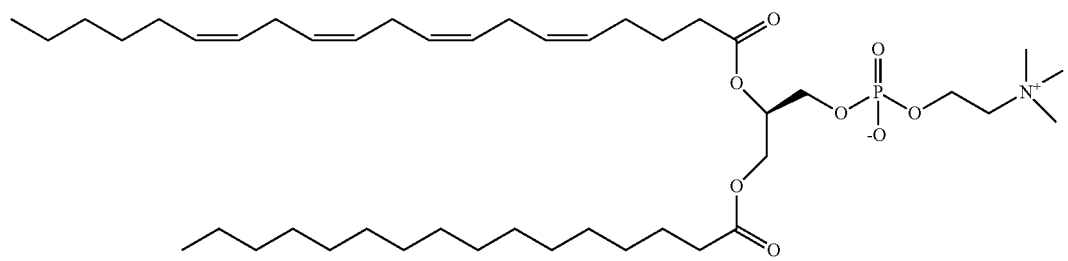
(R)-2((5Z,8Z,11Z,14Z)-icosa-5,8,11,14-tetraenoyl)
oxy)-3-(palmitoyloxy)propyl (2-(trimethylammonio)
ethyl) phosphate ("MPC6")
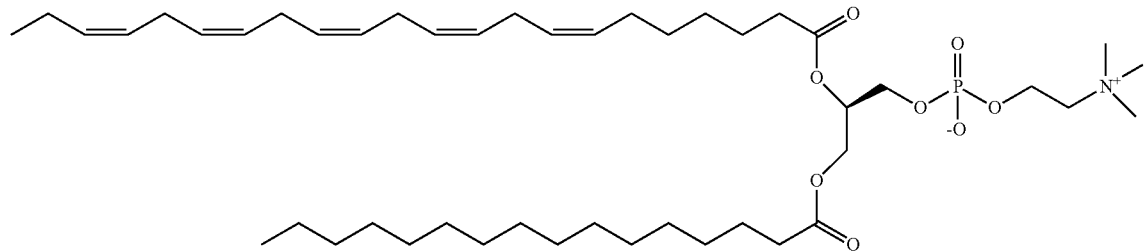
(R)-2((7Z,10Z,13Z,16Z,19Z)-docosa-7,10,13,16,19-
pentaenoyl)oxy)-3-(palmitoyloxy)propyl (2-(trim-
ethylammonio)ethyl) phosphate ("MPC7")
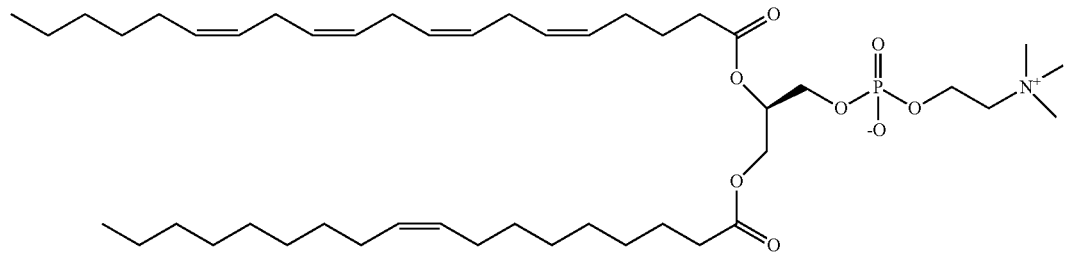

(R)-2((5Z,8Z,11z, 14Z)-icosa-5,8,11,14-tetraenoyl)
oxy)oxy)-3-(oleoyloxy)propyl (2-(trimethylam-
monio)ethyl) phosphate ("MPC8")
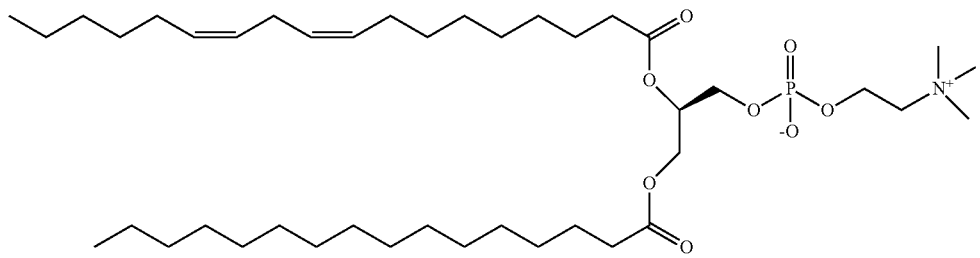
(R)-2-(((9Z,12Z)-octadeca-9,12-dienoyl)oxy)-3-
(palmitoyloxy)propyl (2-(trimethylammonio)ethyl)
phosphate ("MPC9")
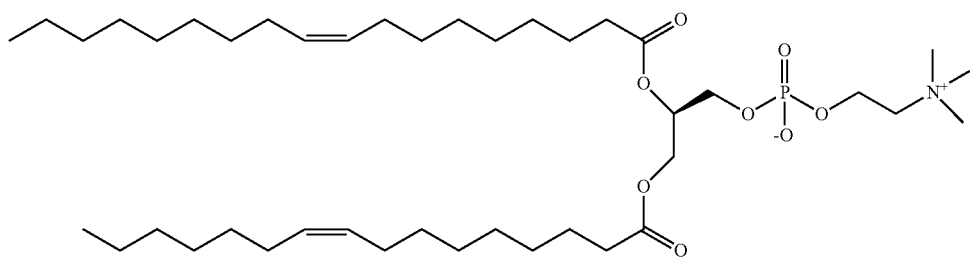
(R)-2-((Z)-octadeca-9-enoyl)oxy)-3-((Z)-hexadec-9-
enoyl)oxy)propyl (2-(trimethylammonio)ethyl)
phosphate ("MPC10")
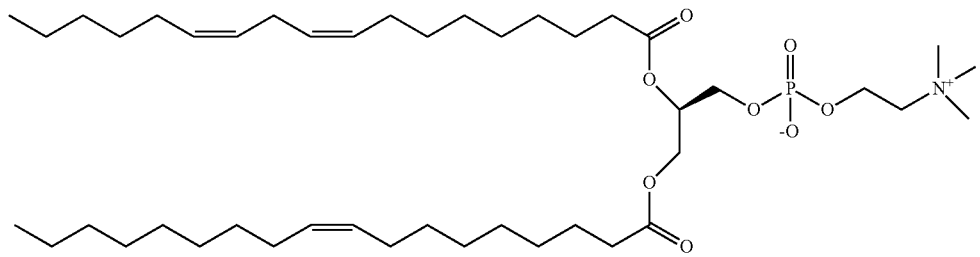
(R)-2-(((9Z,12Z)-octadeca-9,12-dienoyl)oxy)-3-
(oleoyloxy)propyl (2-(trimethylammonio)ethyl)
phosphate ("MPC11")
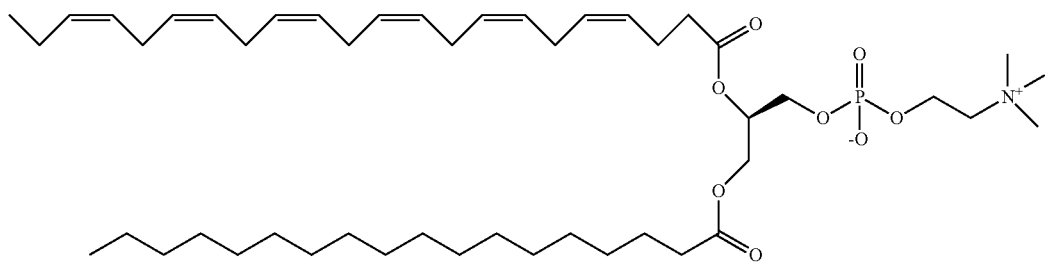

(R)-2-(((4Z,7Z,10Z,13Z,16Z,19Z)-docosa-4,7,10,13,
16,19-hexaenoyl)oxy)-3-(stearoyloxy)propyl (2-
(trimethylammonio)ethyl) phosphate ("MPC12")
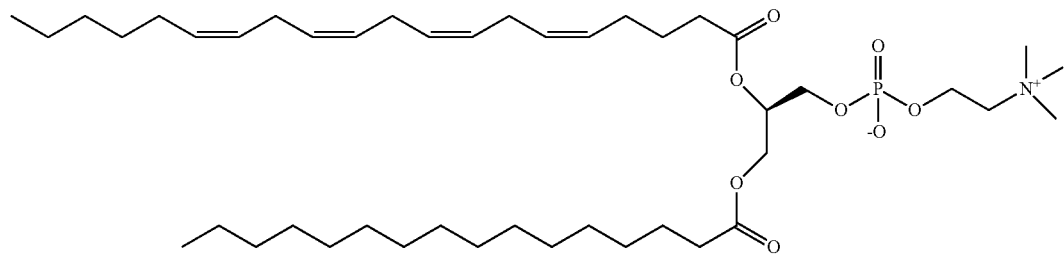
(R)-2-(((5Z,8Z,11Z,14Z)-icosa-5,8,11,14-tetraenoyl)
oxy)-3-(stearoyloxy)propyl (2-(trimethylammonio)
ethyl) phosphate ("MPC13")
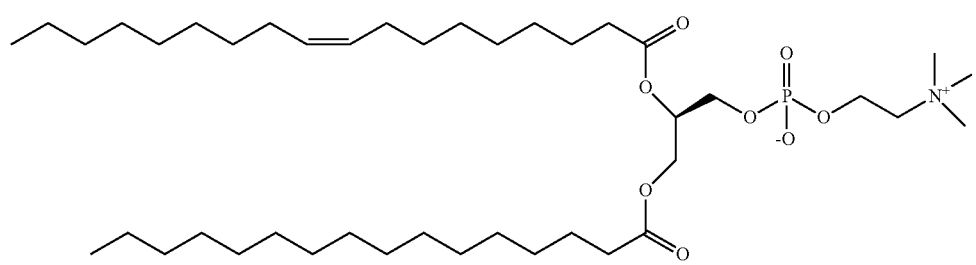
(R)-2-(oleoyloxy)-3-(palmitoyloxy)propyl (2-(trim-
ethylammonio)ethyl) phosphate ("MPC14")
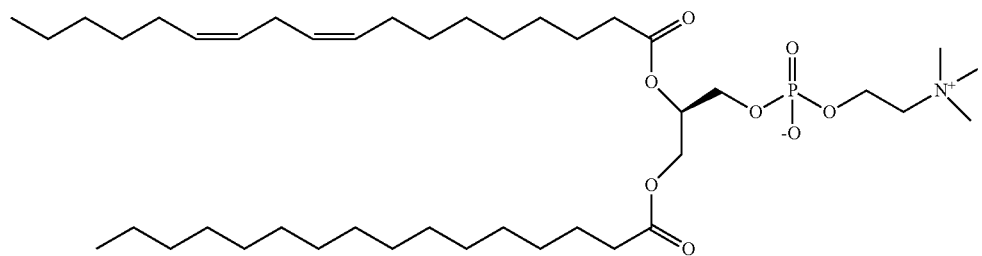
(R)-2-(((9Z,12Z)-octadeca-9,12-dienoyl)oxy)-3-
(stearoyloxy)propyl (2-(trimethylammonio)ethyl)
phosphate ("MPC15")
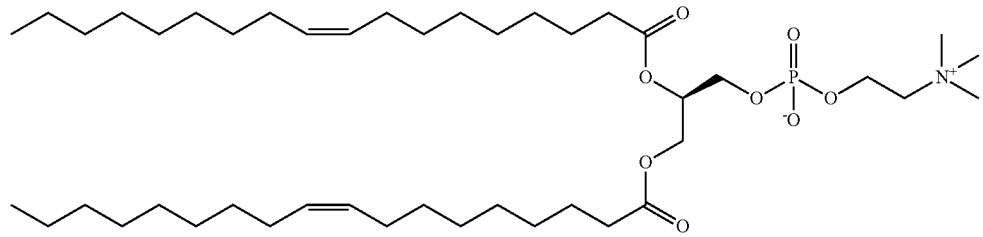

(R)-2,3-bis(oleoyloxy)propyl (2-(trimethylammonio)
ethyl) phosphate ("MPC16")

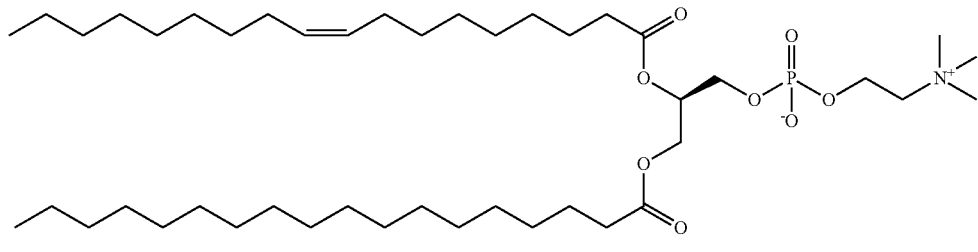

(R)-2-(oleoyloxy)-3-(stearoyloxy)propyl (2-(trimethylammonio)ethyl) phosphate ("MPC17")

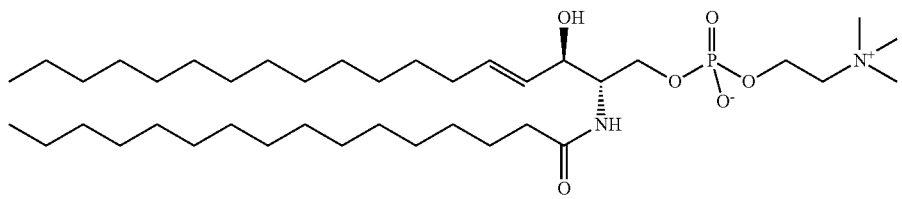 [SMILES: CCCCCCCCCCCCC/C=C/[C@@H](O)[C@H](COP(=O)([O-])OCC[N+](C)(C)C)NC(=O)CCCCCCCCCCCCCCC]

(2S,3R,E)-2-palmitamido-3-hydroxyoctadec-4-en-1-yl (2-(trimethylammonio)ethyl) phosphate ("SPH1")

In one embodiment, a pharmaceutical composition is provided comprising a phosphatidylcholine comprising, consisting essentially of, or consisting of an effective amount of MPC1 and a sphingomyelin comprising, consisting essentially of, or consisting of an effective amount of SPH1, together with a pharmaceutically acceptable carrier and/or excipient. In one embodiment, the MPC1 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC2 and a sphingomyelin comprising, consisting essentially of, or consisting of an effective amount of SPH1, together with a pharmaceutically acceptable carrier and/or excipient. In one embodiment, the MPC2 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC3 and a sphingomyelin comprising, consisting essentially of, or consisting of an effective amount of SPH1, together with a pharmaceutically acceptable carrier and/or excipient. In one embodiment, the MPC3 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC4 and a sphingomyelin comprising, consisting essentially of, or consisting of an effective amount of SPH1, together with a pharmaceutically acceptable carrier and/or excipient. In one embodiment, the MPC4 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC5 and a sphingomyelin comprising, consisting essentially of, or consisting of an effective amount of SPH1, together with a pharmaceutically acceptable carrier and/or excipient. In one embodiment, the MPC5 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC6 and a sphingomyelin comprising, consisting essentially of, or consisting of an effective amount of SPH1, together with a pharmaceutically acceptable carrier and/or excipient. In one embodiment, the MPC6 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC7 and a sphingomyelin comprising, consisting essentially of, or consisting of an effective amount of SPH1, together with a pharmaceutically acceptable carrier and/or excipient. In one embodiment, the MPC7 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC8 and a sphingomyelin comprising, consisting essentially of, or consisting of an effective amount of SPH1, together with a pharmaceutically acceptable carrier and/or excipient. In one embodiment, the MPC8 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC9 and a sphingomyelin comprising, consisting essentially of, or consisting of an effective amount of SPH1, together with a pharmaceutically acceptable carrier and/or excipient. In one embodiment, the MPC9 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC10 and a sphingomyelin comprising, consisting essentially of, or consisting of an effective amount of SPH1, together with a pharmaceutically acceptable carrier and/or excipient. In one embodiment, the MPC10 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC11 and a sphingomyelin comprising, consisting essentially of, or consisting of an effective amount of SPH1, together with a pharmaceutically acceptable carrier and/or excipient. In one embodiment, the MPC11 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC12 and a sphingomyelin comprising, consisting essentially of, or consisting of an effective amount of SPH1, together with a pharmaceutically acceptable carrier and/or excipient. In one embodiment, the MPC12 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC13 and a sphingomyelin comprising, consisting essentially of, or consisting of an effective amount of SPH1, together with a pharmaceutically acceptable carrier and/or excipient. In one embodiment, the MPC13 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC14 and a sphingomyelin comprising, consisting essentially of, or consisting of an effective amount of SPH1, together with a pharmaceutically acceptable carrier and/or excipient. In one embodiment, the MPC14 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC15 and a sphingomyelin comprising, consisting essentially of, or consisting of an effective amount of SPH1, together with a pharmaceutically acceptable carrier and/or excipient. In one embodiment, the MPC15 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC16 and a sphingomyelin comprising, consisting essentially of, or consisting of an effective amount of SPH1, together with a pharmaceutically acceptable carrier and/or excipient. In one embodiment, the MPC16 and SPH1 exhibit enhanced activity in combinations composed to their individual activities. In one embodiment, the pharmaceutical composition is in the form of an oral dosage form (e.g., a capsule), as a fixed-dose combination.

In one embodiment, a pharmaceutical composition is provided comprising a phosphatidylcholine comprising, consisting essentially of, or consisting of an effective amount of MPC17 and a sphingomyelin comprising, consisting essentially of, or consisting of an effective amount of SPH1, together with a pharmaceutically acceptable carrier and/or excipient. In one embodiment, the MPC17 and SPH1 exhibit enhanced activity in combinations composed to their individual activities. In one embodiment, the pharmaceutical composition is in the form of an oral dosage form (e.g., a capsule), as a fixed-dose combination.

Natural hen egg yolk extracts like BAP(−) may also contain lysophosphatidylcholines (LPC) which are a class of phosphatidylcholines having the structure of formula III(a):

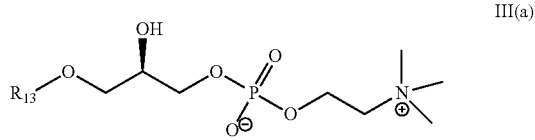

where $R_{13}$ can be any monovalent radical, but is more typically an aliphatic hydrocarbon chain, and are even more typically the acyl functional groups of naturally occurring fatty acids. Pharmaceutical compositions are also provided that are substantially free of these compounds. In some embodiments, the pharmaceutical composition may be substantially free of some or each lysophosphatidylcholine (LPC) having the structure of formula III(a). However, in other embodiments, the pharmaceutical composition may comprise compounds having formula III(a). In some embodiments, the pharmaceutical composition comprises one or more egg yolk extracts enriched with one or more LPCs (e.g., LPC's having the structure of formula III(a)). In some embodiments, $R_{13}$ is hydrogen or alkyl. In some embodiments, $R_{13}$ is an acyl group bonded to a hydrocarbon radical. In other embodiments, the pharmaceutical compositions may be substantially free of compounds and combinations of compounds having the structure of formula III where $R_{13}$ is hydrogen or an acyl group selected from palmitoyl, stearoyl, oleoyl, linoyl, or arachidonoyl. In other embodiments, the pharmaceutical compositions further comprise compounds and combinations of compounds having the structure of formula III(a) where $R_{13}$ is hydrogen or an acyl group selected from palmitoyl, stearoyl, oleoyl, linoyl, or arachidonoyl. In other embodiments, the composition is substantially free of glycerophosphocholine.

Natural hen egg yolk extracts like BAP(−) may also contain lysophosphatidylcholines (LPC) which are a class of phosphatidylcholines having the structure of formula III(b):

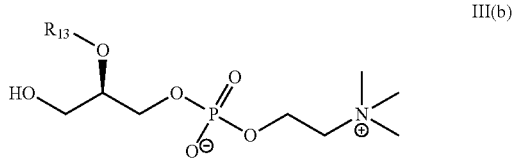

III(b)

where $R_{13}$ can be any monovalent radical, but is more typically an aliphatic hydrocarbon chain, and are even more typically the acyl functional groups of naturally occurring fatty acids. Pharmaceutical compositions are also provided that are substantially free of these compounds. In some embodiments, the pharmaceutical composition may be substantially free of some or each lysophosphatidylcholine (LPC) having the structure of formula III(a). However, in other embodiments, the pharmaceutical composition may comprise compounds having formula III(a). In some embodiments, the pharmaceutical composition comprises one or more egg yolk extracts enriched with one or more LPCs (e.g., LPC's having the structure of formula III(a)). In some embodiments, $R_{13}$ is hydrogen or alkyl. In some embodiments, $R_{13}$ is an acyl group bonded to a hydrocarbon radical. In other embodiments, the pharmaceutical compositions may be substantially free of compounds and combinations of compounds having the structure of formula III where $R_{13}$ is hydrogen or an acyl group selected from palmitoyl, stearoyl, oleoyl, linoyl, or arachidonoyl. In other embodiments, the pharmaceutical compositions further comprise compounds and combinations of compounds having the structure of formula III(b) where $R_{13}$ is hydrogen or an acyl group selected from palmitoyl, stearoyl, oleoyl, linoyl, or arachidonoyl. In other embodiments, the composition is substantially free of glycerophosphocholine.

Table 4 provides the compound names of certain lysophosphatidylcholines (LPC) which may be present in the hen egg yolk extract in some embodiments, and which may be excluded from the compositions in other embodiments (or excluded in substantial amounts). These LPC compounds (e.g., those disclosed in Table 4) may be present individually or in combination with one another and/or in combination with one or more PC compounds, e.g., as described in Table 2 and/or in combination with one or move SPH compound, e.g., as described in Table 3. In some embodiments, the extract may be enriched by one or more LPC disclosed in Table 4 (e.g., LPC1, LPC2, LPC3, LPC4, LPC5, LPC6, LPC7, LPC8, LPC9, LPC 10, LPC11, LPC12, or combinations thereof). It will be understood that because LPCs are a class of PCs, an LPC may be referred to by either LPC number or the PC number.

TABLE 4

| Compound | Compound Name |
|---|---|
| LPC1 | glycerophosphocholine |
| LPC2 | 2-palmitoyl-sn-glycero-3-phosphocholine |
| LPC3 | 2-stearoyl-sn-glycero-3-phosphocholine |
| LPC4 | 2-oleoyl-sn-glycero-3-phosphocholine |
| LPC5 | 2-linoleoyl-sn-glycero-3-phosphocholine |
| LPC6 | 2-arachidonoyl-sn-glycero-3-phosphocholine |
| LPC7 | 2-α-linolenoyl-sn-glycero-3-phosphocholine |
| LPC8 | 2-palmitoleoyl-sn-glycero-3-phosphocholine |
| LPC9 | 2-docosahexaenoyl-sn-glycero-3-phosphocholine |
| LPC10 | 2-eicosapentaenoyl-sn-glycero-3-phosphocholine |
| LPC11 | 2-osbondoyl-sn-glycero-3-phosphocholine |
| LPC12 | 2-clupanodoyl-sn-glycero-3-phosphocholine |

In various embodiments, any of the LPC's listed in Table 4 may comprise individually from about 1-100% (w/w) (e.g., 1-10% (w/w) or 10-20% (w/w) or 20-30% or 30-40% (w/w) or 40-50% (w/w) or 50-60% (w/w) or 60-70% (w/w) or 70-80% (w/w) or 80-90% (w/w) or 90-100% (w/w)) of the phospholipid component (or the lysophosphatidylcholine component) of the pharmaceutical compositions. In some embodiments, the phospholipid component (or the lysophosphatidylcholine component) of the pharmaceutical compositions of the invention may be free of any of the lysophosphatidylcholine compounds (LPC1-LPC12) listed in Table 4, or may be substantially free of such compounds by which is meant that a given LPC is present in such small amounts as to not have a benefit in the treatment of cancer at the given level and in any event will be less than 2.5% (w/w) or less than 1% (w/w) or less than 0.5% (w/w) or less than 0.1% (w/w) based on the total weight of the phospholipid component (or of the LPC component).

In one embodiment, the bioactive lipid composition comprises less than 5% by weight and/or molar mass of LPC's. In other embodiments, the bioactive lipid compositions comprise less than 4%, less than 3%, less than 2%, less than 1%, less than 0.5%, less than 0.25%, or less than 0.1% by weight and/or molar mass of LPC's.

BAP(+) may be produced through the acylation of the nitrogen of various phosphatidylethanolamines (PE) found in the hen egg yolk extract. These PE compounds have the structure of formula I:

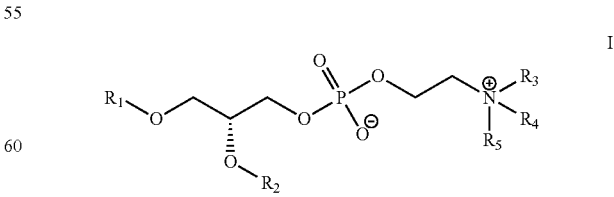

I where $R_1$ and $R_2$ are defined as above, and $R_3$-$R_5$ may be hydrogen or any monovalent hydrocarbon radical. In some embodiments, $R_3$ is selected from hydrogen, methyl or a $C_2$-$C_{18}$ acyl group, and $R_4$ and $R_5$ are independently selected from the group consisting of hydrogen or alkyl (e.g., methyl, ethyl, propyl, etc.), and when $R_3$ is acyl $R_4$ or $R_5$ is absent and the nitrogen bonded to the $R_3$ group is uncharged. For example, $R_3$ may be saturated or $R_3$ may be the acyl group of a fatty acid. In some embodiments, the optionally N-acylated PC lipid may have an $R_3$ group selected from myristoyl, palmitoyl, stearoyl, eicosenoyl, behenoyl, or lignoceroyl. In some embodiments, $R_3$ may be palmitoyl. In some embodiments, $R_3$, $R_4$ and $R_5$ are methyl.

In other embodiments, the pharmaceutical composition comprises optionally N-acylated lysophosphocholines. Optionally N-acylated lysophosphoethanolamine are compounds having the structure of formula III:

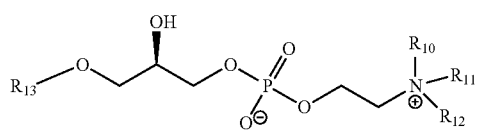

where $R_{13}$ is defined as above, and $R_{10}$-$R_{12}$ may be hydrogen or any monovalent hydrocarbon radical. In some embodiments, $R_{10}$ is selected from hydrogen, methyl or a $C_2$-$C_{18}$ acyl group, and $R_{11}$ and $R_{12}$ are independently selected from the group consisting of hydrogen or methyl and in the case where $R_{10}$ is acyl, $R_{11}$ or $R_{12}$ is absent and the nitrogen bonded to $R_{10}$ is uncharged. For example, $R_{10}$ may be saturated or $R_{10}$ may be the acyl group of a fatty acid. In some embodiments, $R_{10}$ is palmitoyl. In some embodiments of the invention, a beneficial result occurs through enrichment of optionally N-acylated lysophosphocholine in egg yolk extract. In some embodiments, the pharmaceutical composition may further comprise an optionally N-acylated lysophosphocholine. In some embodiments, the optionally N-acylated lysophosphocholine may have an $R_{10}$ group selected from myristoyl, palmitoyl, stearoyl, eicosenoyl, behenoyl, or lignoceroyl. In some embodiments, $R_{10}$ may be palmitoyl. In some embodiments, $R_{10}$, $R_{11}$ and $R_{12}$ are methyl.

The pharmaceutical composition can be administered in any of a number of ways, including oral, parenteral, intravenous, systemic, local, intratumoral, intramuscular, subcutaneous, intraperitoneal, inhalation, or any such method of delivery. The pharmaceutical compositions may be administered intravenously by injection. In one embodiment, a patient is given an intravenous infusion of a solution containing the PCs and/or SPHs through a running intravenous line over, for example, about 30 minutes, about 60 minutes, about 90 minutes or longer. Suitable formulations carriers, diluents, and excipients can be found in Remington's Pharmaceutical Sciences, Mack Publishing Company, Philadelphia, PA, hereby incorporated by reference. Moreover, the pharmaceutical composition may be combined with another treatment for cancer in order to produce a beneficial effect between the two treatment regimens.

The pharmaceutical composition may be formulated for oral administration. In some embodiments, the pharmaceutical compositions may be administered orally or parenterally in a suitable dosage form. When administered orally, the pharmaceutical compositions described herein may be administered in the form of a tablet, gel capsule, liquid capsule, emulsion or liquid. The formulations may conveniently be presented in unit dosage form and may be prepared by conventional pharmaceutical techniques. Such techniques may include the step of mixing the active ingredients and the pharmaceutical carrier(s), excipient(s), and/or diluent(s). In general, the formulations may be prepared by uniformly mixing the active ingredients with liquid carriers or finely divided solid carriers or both, and then, if necessary, shaping the product into, for example, a tablet form or capsule form. In addition, the pharmaceutical compositions may be incorporated into biodegradable polymers allowing for sustained release of the compound, the polymers being implanted in the vicinity of where drug delivery is desired, for example, at the site of a tumor or implanted so that the pharmaceutical compositions is released systematically.

In some embodiments, the compositions described herein may be formulated as a liquid for oral administration. Liquid compositions include solutions, suspensions and emulsions. Examples of liquid pharmaceutical preparations include propylene glycol solutions and solutions containing sweeteners for oral solutions, suspensions and emulsions.

In some embodiments, the unit dosage form is a capsule, such as a gel capsule. In other embodiments, the compositions described herein can be formulated as a fill material for a capsule (e.g., a soft gelatin capsule). A capsule may be prepared, for example, by placing the compositions described above inside a capsule shell. In some embodiments of the invention, the compositions described herein may be filled into soft capsules. A capsule shell may be made of methylcellulose, hydroxypropylmethylcellulose, polyvinyl alcohols, or denatured gelatins or starch or other materials. In some embodiments, the compositions may be filled in hard shell capsules. Hard shell capsules are typically made of blends of relatively high gel strength bone and pork skin gelatins. Other suitable capsule shell materials include polyethylene, polypropylene, poly(methylmethacrylate), polyvinylchloride, polystyrene, polyurethanes, polytetrafluoroethylene, nylons, polyformaldehydes, polyesters, cellulose acetate, and nitrocellulose. The capsule shell itself may contain small amounts of dyes, opaquing agents, plasticizers, and preservatives.

The unit dosage form may also contain binders such as gum tragacanth, acacia, corn starch or gelatin; excipients such as dicalcium phosphate; a disintegrating agent such as corn starch, potato starch, or alginic acid; and/or lubricants such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the phospholipids of the invention may be incorporated into sustained-release preparations and devices.

In various embodiments, the phospholipids of the invention can be administered intravenously or intraperitoneally by infusion or injection. Dispersions of the phospholipids can be prepared in water, optionally mixed with a nontoxic surfactant. Solutions can be prepared in glycerol, liquid polyethylene glycols, triacetin, or mixtures thereof, or in a pharmaceutically acceptable oil. Under ordinary conditions of storage and use, preparations may contain one or more antioxidants or preservatives, for example, to prevent the growth of microorganisms.

In some embodiments of the invention, an effective (stabilizing) amount of one or more pharmaceutically acceptable anti-oxidants is added to the formulation. The term "anti-oxidant" is used herein to describe any compound or combination of compounds that prevents or retards oxidation. Any of the known anti-oxidants may be used, including but not limited to butylated hydroxyanisole (BHA), butylated hydroxytoluene (BHT), propyl gallate, lecithin, Vitamin E tocopherol, sesamin, sesamol, sesamolin, α-tocopherol, ascorbic acid, acorbyl palmitate, fumaric acid, malic acid, sodium ascorbate and sodium metabisulphite, as well as chelating agents such as disodium EDTA, may also be used to stabilize the formulations of the present invention.

The amount of active compounds administered per dose is selected to be above the minimal therapeutic dose but below a toxic dose. The choice amount of dose will depend on a number of factors, such as the medical history of the patient, the patient's age, the patient's weight, the use of other therapies, and the nature of the disease. The preferred dose and dosage regimen can be, for example, about 1 to about 20,000 mg or about 10 to about 10,000 mg per kg body weight of the subject. In certain embodiments, an initially low dose will be given, which can be increased based on the response and/or tolerance of the patient to the initial dose. Oral administration, for example, can occur at equal intervals, i.e., from about 1-10,000 mg/kg or from about 10 to about 10,000 mg/kg every 24 hours (e.g., about 2.5 to about 250 mg/kg every 6 hours) or every 12 hours or every 6 hours, etc. Dosing frequency may be once daily, twice daily, or more frequent. Preferred unit dosage formulations are those containing a daily dose or unit, daily sub-dose, or an appropriate fraction thereof, of the administered ingredients. It should be understood that in addition to the ingredients particularly mentioned above, the formulations of the present invention may include other agents conventional in the art having regard to the type of formulation in question.

In one embodiment, the pharmaceutical compositions of the invention are used to inhibit proliferative activity of neoplastic and in particular to treat neoplasms (e.g., cancers, pre-cancers, tumors, etc.). The pharmaceutical compositions of the invention may be used to treat sarcoma and/or melanoma and/or carcinoma and/or lymphoma and/or leukemia.

The pharmaceutical compositions may be used for the treatment of cancer. In some embodiments, a method of treating bladder cancer in a mammal (e.g., a human) may comprise administration of a pharmaceutical composition comprising an effective amount of a plurality of bioactive phospholipids according to the invention together with one or more pharmaceutically acceptable carriers and/or excipients. In some embodiments, a method of treating blood cancer may comprise administration of a pharmaceutical composition comprising an effective amount of a plurality of bioactive phospholipids according to the invention together with one or more pharmaceutically acceptable carriers and/or excipients. In some embodiments, a method of treating brain (e.g., glioblastoma) cancer may comprise administration of a pharmaceutical composition comprising an effective amount of a plurality of bioactive phospholipids according to the invention together with one or more pharmaceutically acceptable carriers and/or excipients. In some embodiments, a method of treating breast cancer may comprise administration of a pharmaceutical composition comprising an effective amount of a plurality of bioactive phospholipids according to the invention together with one or more pharmaceutically acceptable carriers and/or excipients. In some embodiments, a method of treating cervical cancer may comprise administration of a pharmaceutical composition comprising an effective amount of a plurality of bioactive phospholipids according to the invention together with one or more pharmaceutically acceptable carriers and/or excipients. In some embodiments, a method of treating colorectal cancer may comprise administration of a pharmaceutical composition comprising an effective amount of a plurality of bioactive phospholipids according to the invention together with one or more pharmaceutically acceptable carriers and/or excipients. In some embodiments, a method of treating esophageal cancer may comprise administration of a pharmaceutical composition comprising an effective amount of a plurality of bioactive phospholipids according to the invention together with one or more pharmaceutically acceptable carriers and/or excipients. In some embodiments, a method of treating kidney cancer may comprise administration of a pharmaceutical composition comprising an effective amount of a plurality of bioactive phospholipids according to the invention together with one or more pharmaceutically acceptable carriers and/or excipients. In some embodiments, a method of treating lung cancer may comprise administration of a pharmaceutical composition comprising an effective amount of a plurality of bioactive phospholipids according to the invention together with one or more pharmaceutically acceptable carriers and/or excipients. In some embodiments, a method of treating ovarian cancer may comprise administration of a pharmaceutical composition comprising an effective amount of a plurality of bioactive phospholipids according to the invention together with one or more pharmaceutically acceptable carriers and/or excipients. In some embodiments, a method of treating pancreatic cancer may comprise administration of a pharmaceutical composition comprising an effective amount of a plurality of bioactive phospholipids according to the invention together with one or more pharmaceutically acceptable carriers and/or excipients. In some embodiments, a method of treating skin cancer (e.g., melanoma or carcinoma) may comprise administration of a pharmaceutical composition comprising an effective amount of a plurality of bioactive phospholipids according to the invention together with one or more pharmaceutically acceptable carriers and/or excipients. In some embodiments, a method of prostate blood cancer may comprise administration of a pharmaceutical composition comprising an effective amount of a plurality of bioactive phospholipids according to the invention together with one or more pharmaceutically acceptable carriers and/or excipients. In some embodiments, a method of treating thyroid cancer may comprise administration of a pharmaceutical composition comprising an effective amount of a plurality of bioactive phospholipids according to the invention together with one or more pharmaceutically acceptable carriers and/or excipients. In some embodiments, a method of treating uterine cancer may comprise administration of a pharmaceutical composition comprising an effective amount of a plurality of bioactive phospholipids according to the invention together with one or more pharmaceutically acceptable carriers and/or excipients. In each of the foregoing methods of treatment, the administration may be oral, including by administration of a capsule containing said effective components of the bioactive phospholipid compositions (e.g., MP1000) of the invention. In each of the foregoing methods of treatment, the treatment is carried out for a time sufficient to shrink a tumor, slow progression of a cancer, affect remission of a cancer, and/or inhibit proliferative activity of neoplasmatic cells.

EXAMPLES

Example 1: Fractionation and Characterization of BAP(+) Mixture

A mixture of biologically active phospholipids (BAP(+)), extracted from ischemic chick embryonic tissue (hen egg yolk) with butanol, purified by acetone precipitation, and treated with palmitic acid/CDI was obtained from AREKO Ltd., (Prague, Czech Republic). The BAP(+) mixture was obtained as a 15% suspension in distilled water and maintained under $N_2$ prior to use.

Figure 2A:
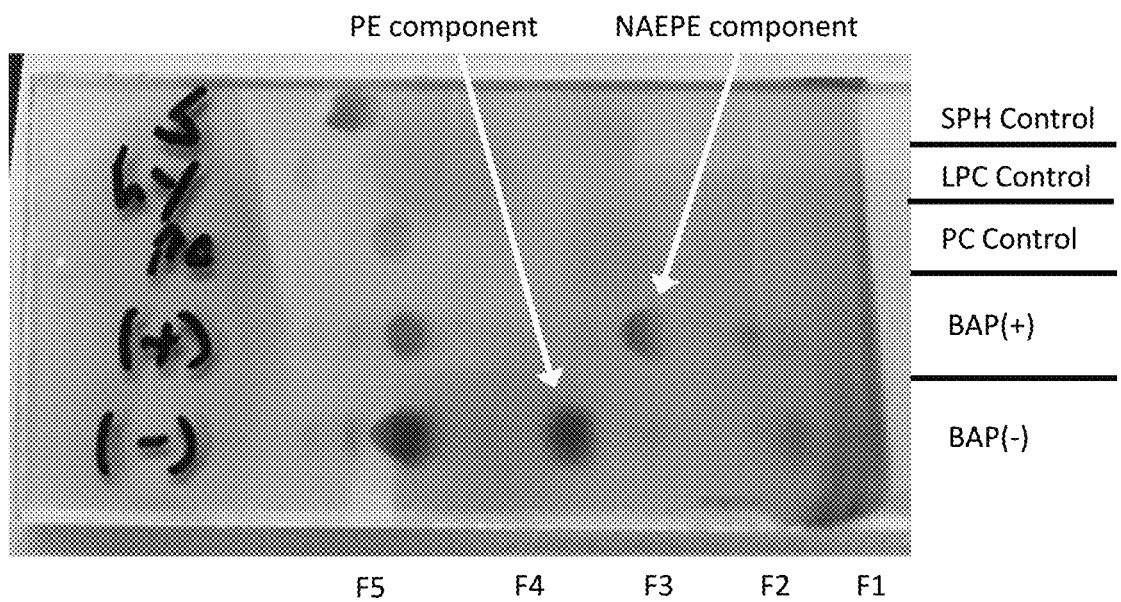
FIG. 2A shows TLC plates for a thin layer chromatographic separation of BAP(+), BAP(−) into various fractions from the left side of the plate to the solvent front on the right. Stains from fractions F1-F5 of BAP (+) and the corresponding fraction F5 of BAP(−) ("F5(−)") may be seen. As can be seen, the acylation BAP(−) to produce BAP(+) converts the PE component of BAP(−) into an NAEPE component present in BAP(+). Also shown are SPH, LPC and PC controls illustrating where those phospholipid classes elute. As can be seen, fraction F5 comprises a sphingomyelin component and a phosphatidylcholine component.

To begin separation of the complex BAP(+) mixture, the solvent was removed from BAP(+) by heating at 40° C. under reduced pressure. Following solvent removal, 3.0 g of the dried BAP(+) mixture was separated by flash chromatography using degassed solvents consisting of dichloromethane, methanol, and water (8:2:0.1) eluent on a column packed with, high-purity grade silica gel (60 Å pore size and 40-63 m particle size) from Sorbent Technologies (GA). The separation of BAP(+) through the column was monitored by thin layer chromatography (TLC) with a phosphomolybdic acid stain. FIG. 2A shows a representative separation of each of the fractions (F1-F5) which was obtained using a chloroform:methanol:water (65:35:7 by volume) eluent and Meck KGA silica gel 60 $F_{254}$ plates as visualized by PMA stain. The first four fractions (F1-F4) eluted had retention factors ($R_f$) of 0.97, 0.90, 0.52, and 0.28, respectively, as determined by TLC. Following complete elution of fraction F4, the eluent was changed to a 6:4:0.6 dichloromethane, methanol and water mixture and the remainder of the BAP(+) material was eluted from column. This fraction is identified as fraction F5. Table 5 illustrates the isolated amounts of each fraction and the approximate (%) abundance of each fraction in the BAP(+) mixture using the above described flash chromatographic fractionation technique. Spectroscopic analysis of the fractions indicated that fraction F3 comprised NAEPEs. That PE's of BAP(−) are converted into NAEPE's can also be seen in FIG. 2A. However, cytotoxicity studies of the fractions suggested that fraction F5 provided the most cytotoxic activity to tumors (see, e.g., Examples 6 and 7 below).

TABLE 5

| Fraction | Weight (mg) | % Abundance in BAP(+) |
|---|---|---|
| F1 | 402.9 | 13 |
| F2 | 234.6 | 8 |
| F3 | 505.0 | 17 |
| F4 | 89.1 | 3 |
| F5 | 1732.1 | 58 |

Example 2: Medium Pressure Chromatography of BAP Mixtures

Other fractionation techniques of BAP(+) were also employed in order to remove NAEPE's while minimizing the potential for decomposition of the PCs. It was determined that contact various BAP mixtures with silica may result in LPC formation and consequently an increase in LPC abundance over time (e.g., presumably via degradation of PCs). The separation of NAEPE containing fractions (e.g., fraction F3) from the other biologically active phospholipid fractions (e.g., F1, F2, F4 and F5) could be more effectively accomplished using medium pressure silica gel chromatography. Medium pressure silica gel chromatography was performed on a Combiflash® RF Lumen (available from Teledyne Isco, NE). The separation was performed using a step gradient method of two eluents where the BAP(+) mixture is separated with a first eluent for a first period of time followed immediately a second eluent for a second period of time. For illustration purposes, separation of 10 g of BAP(+) mixture was achieved using a 120 g Redisep Silica cartridge (cat #69-2203-320) with a flow of 43 ml/min. The mixture was first separated using a linear gradient that changed the ratio of one solvent ("Solvent A" or 0% B) to another solvent ("Solvent B" or 100% B) over 25 minutes. After 25 minutes, a 20-minute isocratic elution of 100% B was performed. Solvent A was a chloroform:methanol:ammonium hydroxide mixture (8:2:0.05 vol:vol:vol ratio) and solvent B was a chloroform:methanol:water:ammonium hydroxide mixture (6:3.4:0.5:0.05 vol:vol:vol ratio). Due to increased purity and better separation of the fractions produced using this chromatographic method, the isolated amounts of each fraction was slightly different than for the flash chromatographic separation. Table 6 illustrates the isolated amounts of each fraction and the approximate (%) abundance of each fraction in the BAP(+) mixture using the medium pressure silica gel chromatographic fractionation technique.

TABLE 6

| Fraction | Weight (g) | % Abundance in BAP(+) |
|---|---|---|
| F1 + F2 | 1.65 | 18.4 |
| F3 | 1.83 | 20.4 |
| F4 | 0.385 | 5.43 |
| F5 | 5.01 | 55.0 |
| MP1000[†] | 4.85 | 54.0 |

[†]LPCs removed from F5 with final chloroform extraction

Without wishing to be bound by theory, such a separation process allows for decreased elution time for the fraction thereby minimizing any degradation products (e.g., LPCs) which may be produced while the fraction is in proximity with the column. For example, using medium pressure chromatography, Fraction F5 may be isolated in about one hour, while flash chromatography conditions described in Example 1 may take approximately eight hours for separation. Successful isolation of the fractions was achieved by using a flow rate approximately 50% of the optimum flow rate of the column used (e.g. the optimum flow rate at which there will be the minimum variance per unit of column length). For example, a 220 g cartridge has an optimal flow rate of about 150 mL/min. However, successful isolations occurred with flow rates of about 75 mL/min. Such a trend was also found at 120 g and 80 g cartridges (which have an optimal flow rate of about 85 and 60 mL/min, respectively) but a more successful isolation of fraction F5 occurs (e.g., less degradation) with a flow rate on these columns of about 43 and 30 mL/min respectively.

Figure 2B:
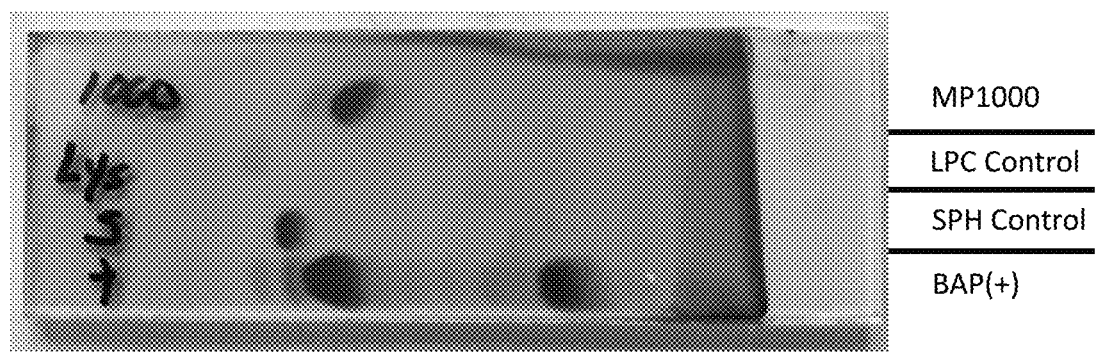
FIG. 2B shows a similar chromatographic separation of MP1000 (top trace) with LPC, SPH and BAP(+) controls. As can be seen, MP1000 is composed of the F5 fraction but an LPC component is substantially absent.
Figure 2C:
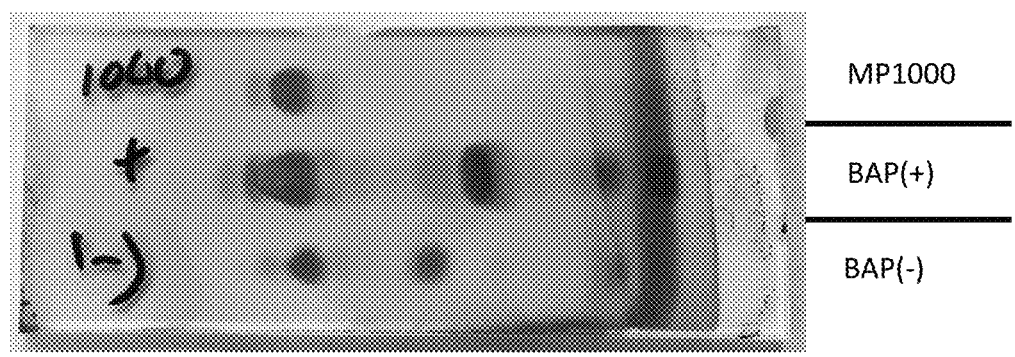
FIG. 2C shows the chromatographic comparison of MP1000, to BAP(+), and BAP(−) controls.

Further purification of Fraction F5 was achieved by extracting with chloroform:methanol:water (1:1:0.8 weight ratio) to remove residual glycerophosphocholine and other degradation products which may be present in the fraction. The resulting chloroform layer containing F5 with LPC removed ("MP1000") was collected and dried. Generally, between about 12 and about 15 g of MP1000 may be separated from 30 g BAP(+) using this procedure. A chromatographic comparison of MP1000, BAP(+), SPH and LPC is illustrated in FIGS. 2B and 2C. The NAEPE component separated from BAP(+) is notably absent in fraction F5. Also, it can be seen that MP1000 is composed of fraction F5, but comprises a significantly LPC component. Accordingly, MP1000 is a more than 90% purified fraction F5.

Example 3: Fractionation and Characterization of Fraction F5 and MP1000

Fraction F5 (and MP1000) were further fractionated into smaller groups of lipids using preparative reverse phase chromatography on a ThermoFisher UltiMate 3000 semi-preparative HPLC system equipped with a flow splitter and a Corona Veo Charged Aerosol Detector (available from DIONEX, CA) for sample detection. Preparative separation of lipid mixtures occurred on a HYPERSIL GOLD silica column (21×150 mm) with a flow rate of 5.0 mL/min with 30:70 eluent ratio (eluent A:eluent B by volume) Eluent A was an acetonitrile:isopropanol solution (3:1 v/v ratio) and eluent B was methanol:triethyl amine (0.9:0.1 v/v ratio). Fractions were collected, pooled and evaporated under reduced pressure. The resulting materials were dried under vacuum to constant weight for use in spectroscopic, in vitro and/or in vivo experiments. Additional semi-preparative HPLC analysis was performed on Fraction F5 to in order further isolate the fraction.

Figure 3A:
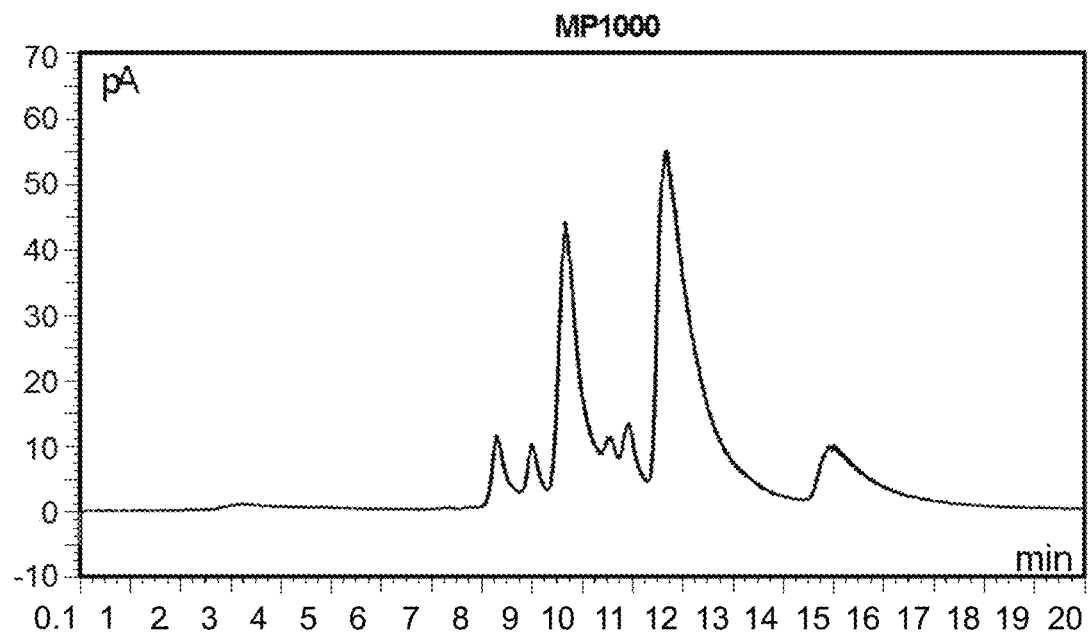
FIG. 3A shows an HPLC chromatogram of fraction MP1000 and demonstrates the isolation and separation of further sub-fractions P1, P2, P3, P4, P5, P6, and P7. Additionally, retention times and area under curve for each sub-fraction are shown.
Figure 3B:
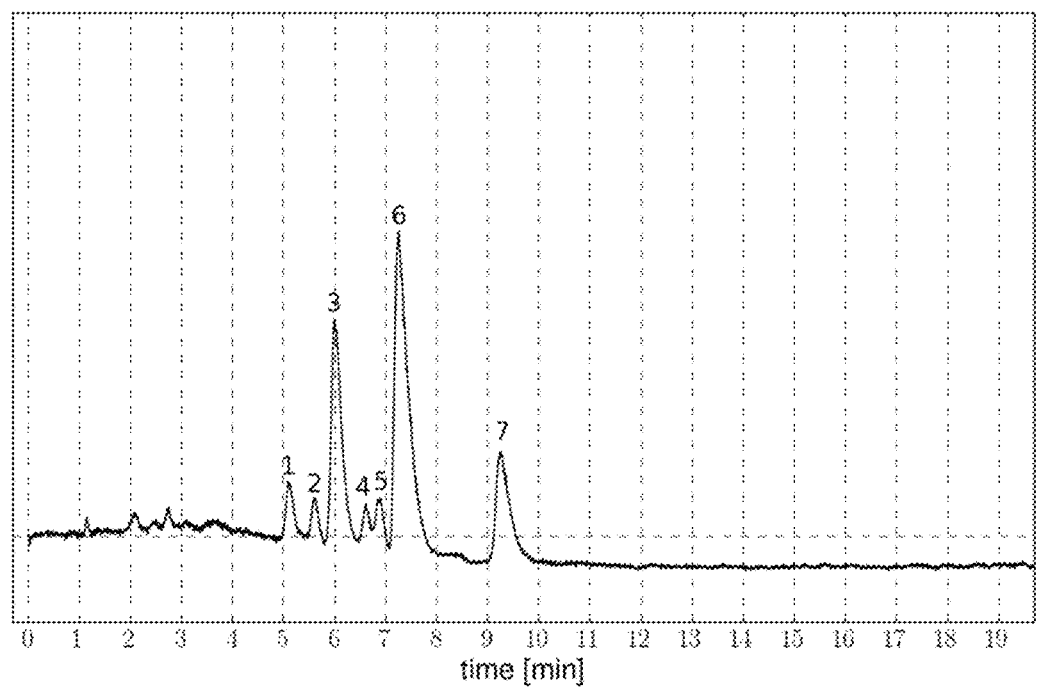
FIG. 3B shows the HPLC chromatogram for Fraction F5 with sub Fractions P1-P7 identified.

An HPLC chromatogram was taken of Fraction F5 (and MP1000) using a C18 HYPERSIL GOLD silica column (250×10 mm, 4.5 mL/min) and isocratic conditions comprised of 30:70 A:B, where solvent A is acetonitrile+0.1% triethyl amine and solvent B is methanol+0.1% triethylamine. The HPLC chromatogram of MP1000 is shown in FIG. 3A. The fraction F5 produced according to Example 1 without application of additional pressure (i.e., not using medium pressure chromatography) may also be separated into peaks P1-P7. The HPLC chromatogram for fraction F5 isolated using the protocol of Example 1 is illustrated in FIG. 3B. Table 7 gives the relative abundances of P1-P7 as measured in the chromatogram from FIG. 3A.

TABLE 7

| Sub-Fraction | Approximate Relative Abundance |
|---|---|
| P1 | 4.0% |
| P2 | 3.2% |
| P3 | 21.7% |
| P4 | 3.5% |
| P5 | 5.0% |
| P6 | 49.3% |
| P7 | 13.4% |

Additional characterization of the constituents of sub-fractions P1 to P7 was performed using mass spectrometry and nuclear magnetic resonance (NMR) techniques. For mass spectrometry, samples of each fraction were dissolved in 5 mM ammonium acetate in methanol solution to a concentration of 0.1 mg/mL. The components of each solution were ionized using an electrospray ionization (ESI) source and filtered by mass using a quadrupole mass spectrometer (AB SCIEX 5000, available from AB SCIEX, MA) to detect the mass of each parent molecule in the fraction and the relative abundance of each parent molecule in the samples. The fatty acid residues were elucidated by neutral loss due to cationic ESI (ESI$^+$). The parent molecule fragments to create the neutral corresponding ketene of the fatty acid in ESI$^+$. Conversely, anionic ESI (ESI$^-$) results in anionic fatty acid loss from the corresponding core. Cross correlation of ESI$^+$ and ESI$^-$ mass spectroscopic results was used to determine the position of the fatty acids in each core based on the fragmentation patterns of the parent molecules following ESI$^+$ and ESI$^-$ as described in Holčapeka, et. al., J. Chromatography A 1218 (2011) 5146-5156, hereby incorporated by reference in its entirety.

Additionally, the sub-fractions were analyzed by the MS-MS techniques (University of Colorado Denver, Mass Spectrometry Lipidomics Core Facility) disclosed in Jangle, R. D. et al. Ind. J. of Pharm. Sci. 75 339-345 (2013), and Zacek, P. et al. J Lipid Res. 2016 December; 57(12):2225-2234, each hereby incorporated by reference in their entirety. Briefly, each sub-fraction was dissolved in methanol:acetonitrile:water (60:20:20 vol:vol:vol ratio) with 1 mM ammonium acetate and further mass spectroscopic analysis was applied thereto. The molecular species were determined via infusion of each sub-fraction solution into an AB Sciex triple quadrupole linear ion trap mass spectrometer at a flow rate of 10 µL/min. In positive ion mode, the orifice was set to +65V with a collision energy of 30V in order to measure a characteristic signal of phosphocholine phospholipids (phosphocholine ion with m/z=184). Collisional activation of each molecular species in negative ion mode allows for the determination of fatty acids esterified to glycerol backbones. These collision induced experiments were performed with an electrospray voltage of −4800 V and a de-clustering potential of −120 V allowing for detection of the [M−15]$^-$ ions (parent loss of methyl anions). When compounds of the same mass are present in a mass spectrum, this protocol allows for the mass spectroscopic detection of the predominant lipid contributing to m z signal at the same detected m z peak.

Further characterization of the constituents within each fraction was performed using $^1$H NMR spectroscopic, two dimensional correlation spectroscopic ([$^1$H-$^1$H]-2D-gCOSY) and heteronuclear single-quantum correlation spectroscopic ([$^1$H-$^{13}$C]-gHSQC) techniques. Spectra were recorded on a Varian Inova 500 instrument. The signal was analyzed relative to the residual solvent peak for CDCl$_3$ ($\delta_H$=7.26, and $\delta_C$=77.4). The structures, as elucidated by mass spectrometry and NMR spectroscopy, of the molecular species of fractions P1 to P7 fraction are given in Table 8.

Fraction F5 comprises phosphatidylcholines (PC), sphingomyelin (SPH) and low quantities of lysophosphatidylcholines (LPC). The LPC component of F5 may comprise degradation products produced during the extraction and isolation of F5. A single fraction (P4) was identified to comprise sphingomyelins. Table 8 summarizes the major PC and LPC molecular species present in each other fraction of F5. Additionally, Table 8 indicates the relative abundance of the molecular species (reported as mole percent) in each sub-fraction. Species comprising less than 5% (mole) are not shown. As shown in Table 8, the $R_1$, and $R_2$ functional groups of the PC species present in Fraction F5 correspond to acyl groups of the form —C(O)R where R is a saturated or unsaturated hydrocarbon chain (e.g., palmitoyl is (C16: 0)) or hydrogen. PC compounds have the structure shown below in formula I(a):

I(a)

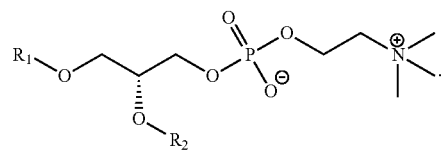

TABLE 8

| Lipid No. | m/z | $R_1/R_2$ (lipid number) | Mol. % in fraction | Lipid Designation |
|---|---|---|---|---|
| Fraction P1 | | | | |
| 1 | 806.6 | (C16:0)/(C22:6) | 61.6 | MPC1 |
| 2* | 756.6 | (C16:1)/(C18:2)- predominant and (C:16:0)/(C18:3) | 15.1 | MPC2 and MPC3 |
| 3* | 782.7 | (C18:2)/(C18:2)- predominant and (C18:1)/(C18:3) | 11.3 | MPC4 and MPC5 |
| Fraction P2 | | | | |
| 4 | 782.6 | (C16:0)/(C20:4) | 61.2 | MPC6 |
| 5* | 808.6 | (C16:0)/(C22:5) and (C18:1)/(C20:4)- predominant | 18.2 | MPC7 and MPC8 |
| Fraction P3 | | | | |
| 6* | 758.7 | (C16:0)/(C18:2)- predominant and (C16:1)/(C18:1) | 67.2 | MPC9 and MPC10 |
| 7* | 784.7 | (C16:0)/(C20:3) and (C18:1)/(C18:2)- predominant | 12.8 | MPC11 |
| 8 | 834.6 | (C18:0)/(C22:6) | 5.8 | MPC12 |
| Fraction P4 (SPH component; SPH1) | | | | |
| Fraction P5 | | | | |
| 9 | 810.6 | (C18:0)/(C20:4) | 67.3 | MPC13 |
| Fraction P6 | | | | |
| 10 | 760.7 | (C16:0)/C(18:1) | 54.4 | MPC14 |
| 11* | 786.7 | (C18:0)/(C18:2)- predominant and (C18:1)/(C18:1) | 23.4 | MPC15 and MPC16 |
| Fraction P7 | | | | |
| 12 | 886.6 | (C18:0)/(C18:1) | >90 | MPC17 |

*The PC producing the indicated lipid number peaks may be either of the PCs indicated or a combination thereof. Generally, the lipid labeled "predominant" is present in mol percent of each indicated lipid number by more than 50% by mol.

Fraction P4 may not comprise PC compounds. However, Fraction P4 comprises one or more SPH compounds having the structure of formula II(a):

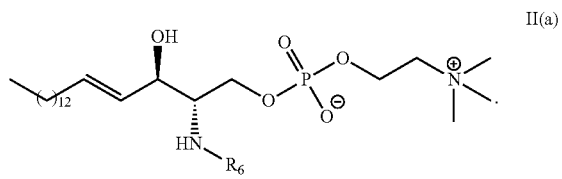

II(a)

The sphingomyelin compound of Fraction P4 in Table 8 had a m/z of 703.8 and was determined to have a palmitoyl acyl group (C16:0) at the $R_6$ position (designated herein as "SPH1").

Figure 4:
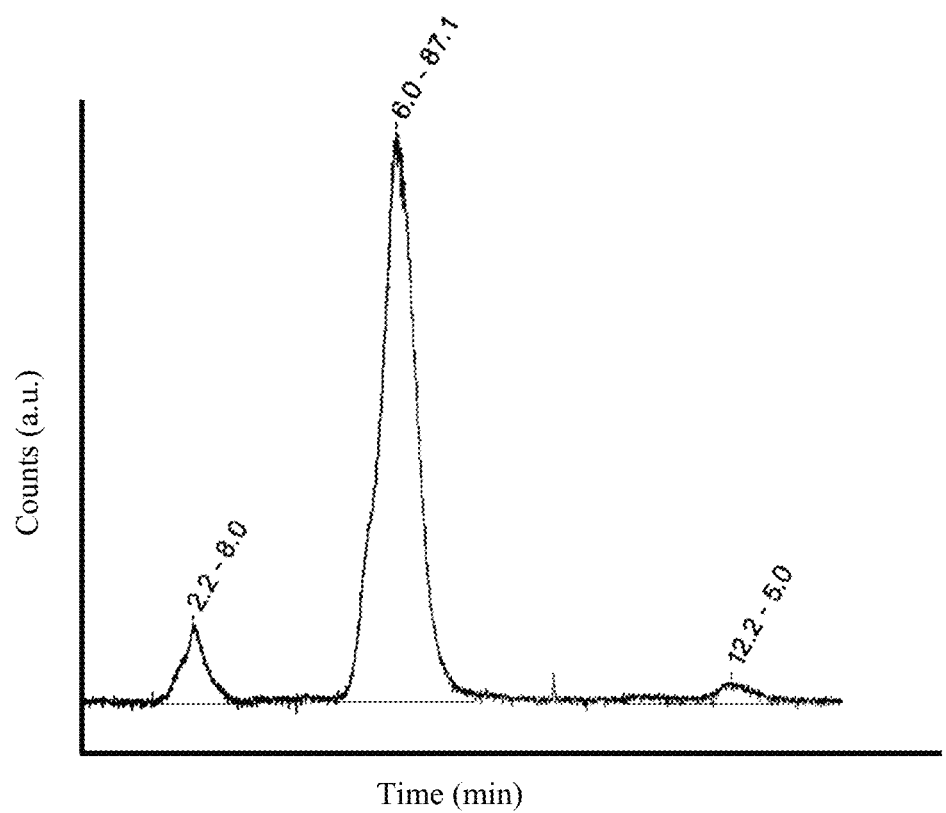
FIG. 4 illustrates a chromatogram of MP1000 separation using normal phase HPLC protocol which separates the lipid species. The peak eluting at 6.0 minutes corresponds to the phosphatidylcholine component and the peak eluting at 12.2 minutes corresponds to the sphingomyelin component. The peak eluting at 2.2 minutes corresponds to the solvent front in this chromatographic extraction and does not correspond to any part of MP1000.

Example 4: Separation of MP1000 into Lipid Classes Using Silica Gel Chromatography MP1000 was separated into each lipid class (e.g., sphingomyelin component, phosphatidylcholine component, etc.) using normal phase HPLC using a ThermoFisher Ultimate 3000 UPLC system equipped with a Corona Veo RS Charged aerosol detector and a Hypersil GOLD Silica 150×4.6 mm column, flow rate 1 ml/min, using isocratic conditions consisting of 30:70 ratio of Eluent A=CHCl$_3$:MeOH:32% NH$_3$/H$_2$O solution (80:19.5:0.5 by volume) and Eluent B=CHCl$_3$:MeOH:TEA:H$_2$O (69.53:25.58:0.49:4.40 by volume). A representative chromatogram is shown in shown in FIG. 4. As can be seen, MP1000 predominantly comprises phosphatidylcholines and sphingomyelins (with a mol/mol ratio of 17.4:1).

Example 5: Fatty Acid Methyl Ester (FAME) Analysis of MP1000

The fatty acid groups of the phospholipids of MP1000 and a fraction from (BAP(-)) which was isolated using a method identical to that used for the MP1000 isolation ("MP1000 (-)") were converted to methyl esters to identify the fatty acid content in each fraction. Identification of the fatty acid content of the mixture of methyl esters was performed by gas chromatographic techniques to elucidate (FAME analysis by Matreya, LLC of State College, PA).

1 mL of 2% sulfuric acid in methanol (by volume) was added to 10 mg of each lipid mixture. The reaction mixtures were then heated for 30 minutes at 80° C. and then cooled to room temperature. 0.5 mL of DI water and 4 mL of hexane were then added. The reaction mixture was shaken vigorously and left to stand until two phases became visible. The hexane layer is collected. This hexane extraction is performed two additional times and pooled. A small amount of sodium sulfate:sodium bicarbonate (4:1 ratio by weight) is added to the pooled hexane extract, shaken vigorously, and concentrated with a nitrogen stream to 0.5 mL to produce the mixtures of methyl esters.

The mixtures of methyl esters were then analyzed using gas chromatography-flame ionization detection (GC-FID) which allows for the identification of molar response factor of specific hydrocarbons. The GC-FID device had an injection and detection temperatures of 250° C. The GC-FID was run with a column comprising a non-bonded poly(80% biscyanopropyl/20% cyanopropylphenyl siloxane phase (SP-2330 Column available from Supelco) dimensioned 30 m×0.25 mm×0.2 m. The column was initially set to 170° C., the temperature was held for 17 minutes, then changed 10° C./min to 190° C. where the temperature was then held again for 31 minutes. The GC-FID carrier gas had a linear velocity of 20 cm/sec.

Figure 5:
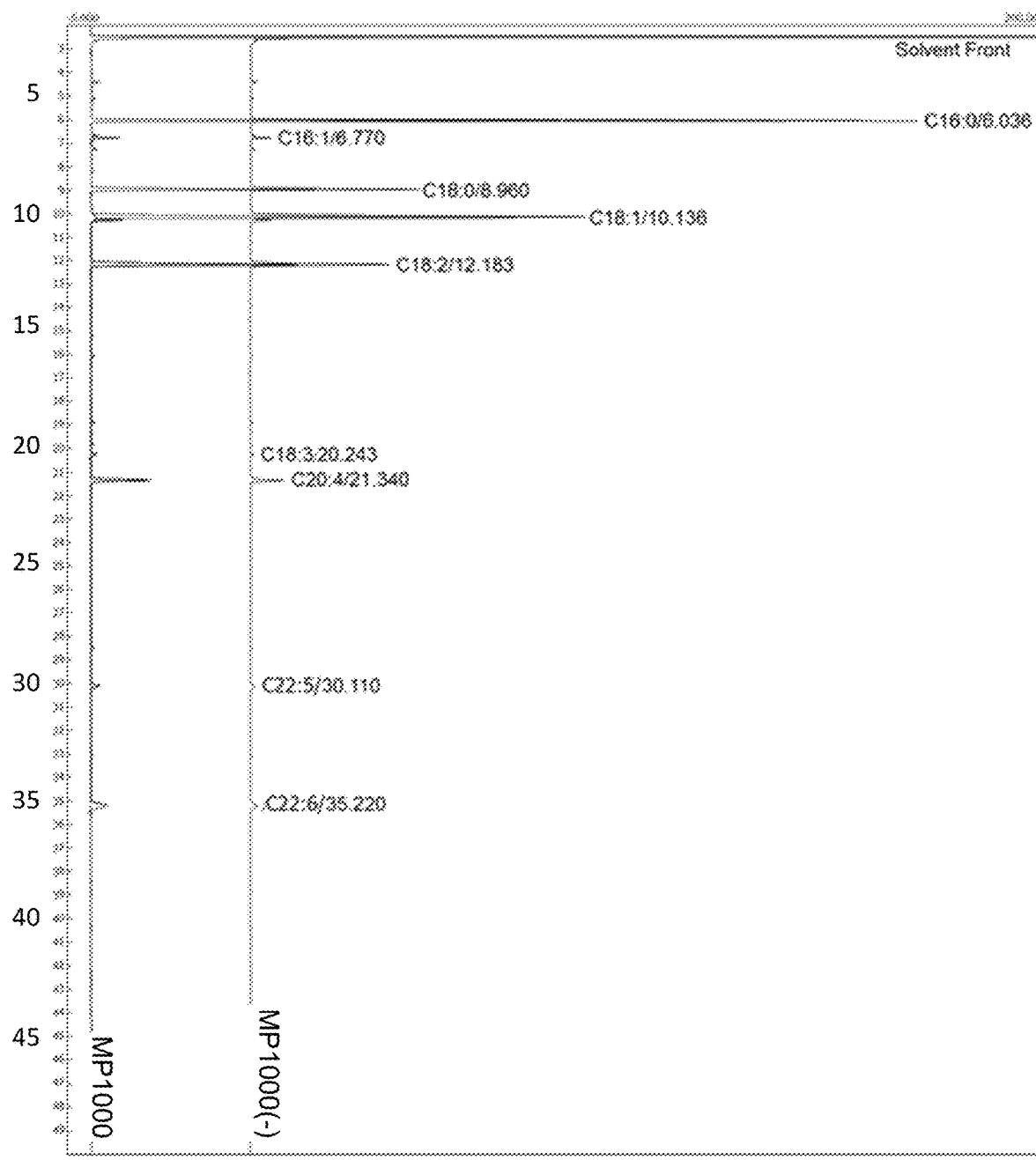
FIG. 5 illustrates a gas chromatogram of fatty acid methyl ester analysis of MP1000 and MP1000(−). The RT for several prominent methyl esters are given. The MP1000(−) is offset from the zero line for comparison of the two traces.

By comparing the retention times of authentic samples of fatty acid methyl esters with the retention time of the FAME obtained from MP1000 and MP1000(-) methyl ester mixtures allowed for identification of the fatty acid content in each fraction. FIG. 5 illustrates the chromatograms from the FAME analysis. The identified species are illustrated in Table 9. The hydrocarbon radical other than the methyl group in each case is indicative of the fatty acid acyl fragment present in the SPH's and PC's found in fraction F5. As can be seen, MP1000 and MP1000(-) appear to have similar fatty acid acyl content in the biophospholipid mixture.

TABLE 9

| Fatty acid species | % Abundance in MP1000 | % Abundance in MP1000(-) |
|---|---|---|
| Methyl hexadecanoate, (C16:0) | 33 | 33 |
| Methyl hexadecenoate, (C16:1, cis-9) | 1 | 1 |
| Methyl octadecanoate, (C18:0) | 13 | 13 |
| Methyl octadecenoate, (C18:1, cis-9) | 30 | 31 |
| Methyl octadecadienoate, (C18:2, all cis-9,12) | 15 | 14 |

TABLE 9-continued

| Fatty acid species | % Abundance in MP1000 | % Abundance in MP1000(−) |
|---|---|---|
| Methyl eicosatetraenoate, (C20:4, all cis-5,8,11,14) | 4 | 3 |
| Methyl docosahexaenoate, (C22:6, all cis-4,7,10,13,16,19) | 2 | 1 |
| Methyl octadecatrienoate, (C18:3, all cis-9,12,15) | >1 | >1 |
| Methyl docosapentaenoate, (C22:5, all cis-7,10,13,16,19) | >1 | >1 |

Example 6: In Vitro Cytotoxicity Analysis of BAP(+) and Fractions F1-F5

The cytotoxic potential of various BAP mixtures was measured using an XTT cell viability assay as follows. Stock solutions of samples BAP+, Fraction F5, sub-fractions of Fraction F5 (e.g., sub-fraction P1, etc.), and a fraction from untreated egg yolk (BAP(−)) which was isolated using a method identical to that used for the Fraction F5 isolation ("F5(−)") were prepared by dissolving or suspending the same amount of each material in phosphate buffer saline (PBS) of physiological concentration and pH of 7.2. Egg phospholipid (BAP(−)) (previously shown not to possess significant cytotoxic activity) was added as an emulsifier in an amount of 0.5% (w/w) for samples that did not form stable suspensions. Solutions/suspensions were prepared by vigorously shaking the components in vials under nitrogen atmosphere for 1-2 hours at ambient temperature. Immediately before testing, the solutions were again homogenized by shaking and then diluted to the appropriate concentration in the cell growth medium to form the test solutions.

A standard XTT assay was used to measure the half minimal inhibitory concentrations ($IC_{50}$) of each of the test materials on the human pancreatic ductal adenocarcinoma cell line (Capan-2).

Flat-bottomed microplates with 96 wells each (available from NUNC, Denmark) were seeded with Capan-2 cells ($6 \times 10^3$ cells/well) in 200 μL of cell growth media. Cells were incubated for 24 hours at 37° C. in a humidified 5% $CO_2$/95% air atmosphere. After 24 hours, 50 μL of the test solutions were added to the wells (in triplicate) to achieve concentrations ranging from 0.0125-0.4% (w/w). Plates were then incubated for an additional 72 hours. Following incubation, 150 μL of supernatant was discarded and a mixture of 25 μL of a 1 mg/mL dye solution of 2,3-bis-(2-methoxy-4-nitro-5-sulfophenyl)-2H-tetrazolium-5-carboxanilide (XTT) and 7.5 μg/mL N-methyl dibenzopyrazine methyl sulfate (PMS) was added to each well. Microplates were incubated for another 4 hours in the absence of light.

The number of adenocarcinoma cells in each well was determined by measuring absorbance at 450 nm with an INFINITE F50 absorbance reader equipped with Magellen for INFINITE F50 software (Tecan Austria GmbH, Austria). Cells cultivated in fresh medium were used as controls. All reported $IC_{50}$ values are the mean of four independent experiments. Table 10 gives the inhibitory activity of various BAP mixtures tested.

TABLE 10

| BAP Mixture | $IC_{50}$ (mg/mL) |
|---|---|
| BAP(+) | 0.74 |
| F5(−) | no activity |

TABLE 10-continued

| BAP Mixture | $IC_{50}$ (mg/mL) |
|---|---|
| F5 | 1.17 |
| P1 | 0.20 |
| P2 | 0.23 |
| P3 | 0.55 |
| P4 | 0.29 |
| P5 | 0.30 |
| P6 | no activity |
| P7 | no activity |

As can be seen in Table 10, BAP(+) and fraction F5 are active against cancer cells, however, F5(−) and some sub-fractions of F5 are not. The most active fractions of F5 (in decreasing order) are P1, P2, and P4. Similar results may also be expected on H358 (lung), M14 (melanoma), 231 (breast), Panc1 (pancreas), HeLa (cervical), SK-OV-3 (ovarian), HepG2 (liver), HCT116 (colon), T98G (glioblastoma multiforme), Jurkat (T cell lymphoma), DU-145 (prostate), or A549 (lung) cell cultures.

Example 7: In Vivo Measurement of Cytotoxicity of BAP Mixtures

In vivo measurements of tumor growth inhibition in mice were conducted to determine efficacy of BAP(+), BAP(−), and fractions thereof. A human pancreatic carcinoma cell line (Capan-2 available from European Collection of Cell Cultures, Salisbury UK) was cultivated at 37° C. in a humidified 5% $CO_2$/95% air atmosphere using high glucose D-MEM medium supplemented with 20% fetal bovine serum, 2% penicillin/streptomycin and 1.25% L-glutamine. Before application, cells were harvested by trypsinisation for 30 minutes. Harvested Capan-2 cells were administered subcutaneously to each mouse as $1 \times 10^7$ cells in a mixture with a basement membrane preparation (BD MATRIGEL, available from I.T.A.-Interact, Prague CZ). Administration was in the rear right flank of Hsd:athymic nude-Fox n1nu mice (available from Anlab, Prague CZ). When the tumor in each mouse reached a volume of about 0.103-0.122 $cm^3$, the testing of the tumor growth inhibition on each mouse began by oral administration of 0.1 mL of a 30% (w/w) solution of each listed component in a sunflower oil carrier once a day for 42 days.

Table 12 gives the percentage of tumor weight growth inhibition (% WGI) as compared to the control for various BAP mixtures including BAP(−), BAP(+), pooled fractions F1-F4, F5, a fraction comprising a pooled collection of the F5 sub-fractions enriched in more PCs comprising saturated fatty acids acyl residues ("F5A"), a fraction which comprising a pooled collection of F5 sub-fractions enriched in more PCs comprising unsaturated fatty acid acyl residues ("F5B"), and a fraction of BAP(+) possibly enriched in LPC's ("F5C"). Glycerophosphocholine (GPC) was also evaluated. The only BAP(+) fractions which comprised a sphingomyelin component were fractions F5 and F5B.

TABLE 11

| Sample | % WGI |
|---|---|
| F5 | 85.7% |
| BAP(+) | 80.7% |
| F1 + F2 + F3 + F4 | 78.3% |
| F5A | 27.8% |
| F5B | 24.9% |
| BAP(−) | −8.8% |

TABLE 11-continued

| Sample | % WGI |
|---|---|
| GPC | −41.9% |
| F5C | −109.2% |

As can be seen in Table 11, the in vivo experiments demonstrate the inhibitory effect specific mixtures of BAP (+) have on tumor growth. Fraction F5 and BAP(+) are each highly active at inhibiting tumor growth. Moreover, fractions F5A and F5B alone have significantly less inhibitory behavior on tumor growth than fraction F5 (which contains both F5A and F5B). It is also observed that fraction F5A, a fraction enriched in unsaturated PCs, has comparable activity to fraction F5B, a fraction enriched in saturated PCs and SPHs, but the combination of F5A and F5B is evidently required for maximum efficacy. Fraction F5C (which is believed to contain LPC's) more than doubled tumor size. It is also notable that BAP(−) did not inhibit tumor growth.

Figure 6:
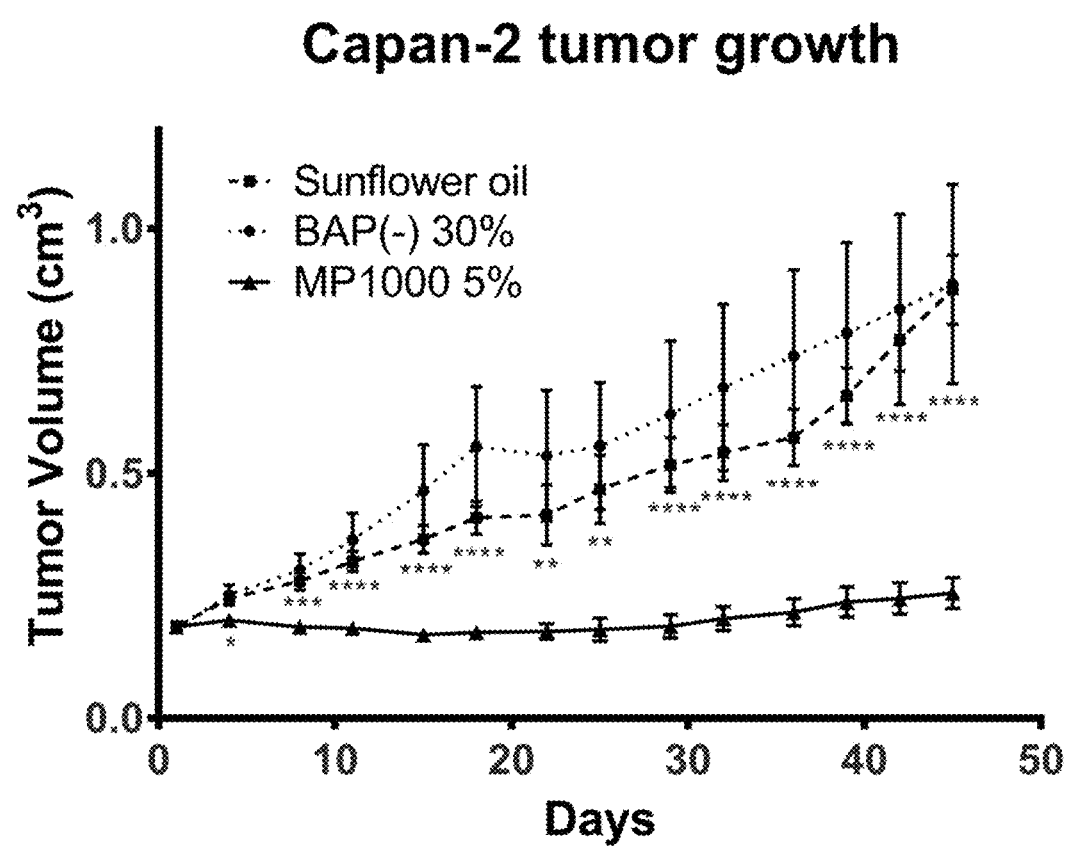
FIGS. 6, 7 and 8 illustrate in vivo mouse model tumor growth measurements of various cancer cell lines as a result of administration of various BAP mixtures.

Additionally, in vivo experiments were performed on F5 fractions isolated from the semi-preparative medium pressure chromatography methodology of Example 2 ("MP1000"). Dosing solutions comprising 5% and 30% by weight concentration were prepared in sunflower oil. Mice with tumors were orally administered 0.1 mL of the MP1000 solutions once per day for 42 days. FIG. 6 illustrates the results of these experiments. As can be seen, the MP1000 fraction reduced the tumor weight significantly more than BAP(−) and control at each time point. A t-test was performed on data at each time point, analyzing statistical significance between the treatments from the sunflower oil control and 5% by weight MP1000 ("*" indicates $p<0.05$, "" indicates $p<0.01$, "*" indicates $p<0.001$, and "****" indicates $p<0.0001$). It is noteable, even though MP1000 and MP1000(−) have similar fatty acid content as demonstrated by FAAME analysis, BAP(−), which comprises MP1000(−), does not reduce the tumor size relative to control.

Figure 7:
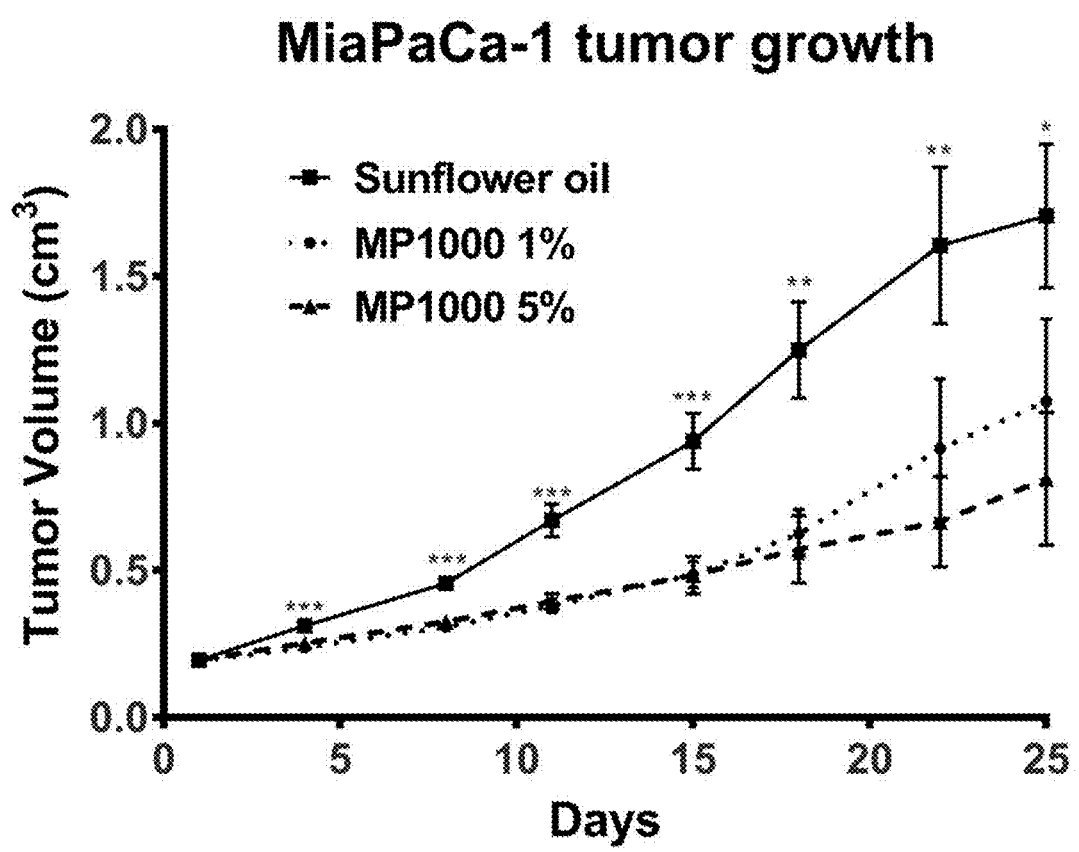
Figure 8:
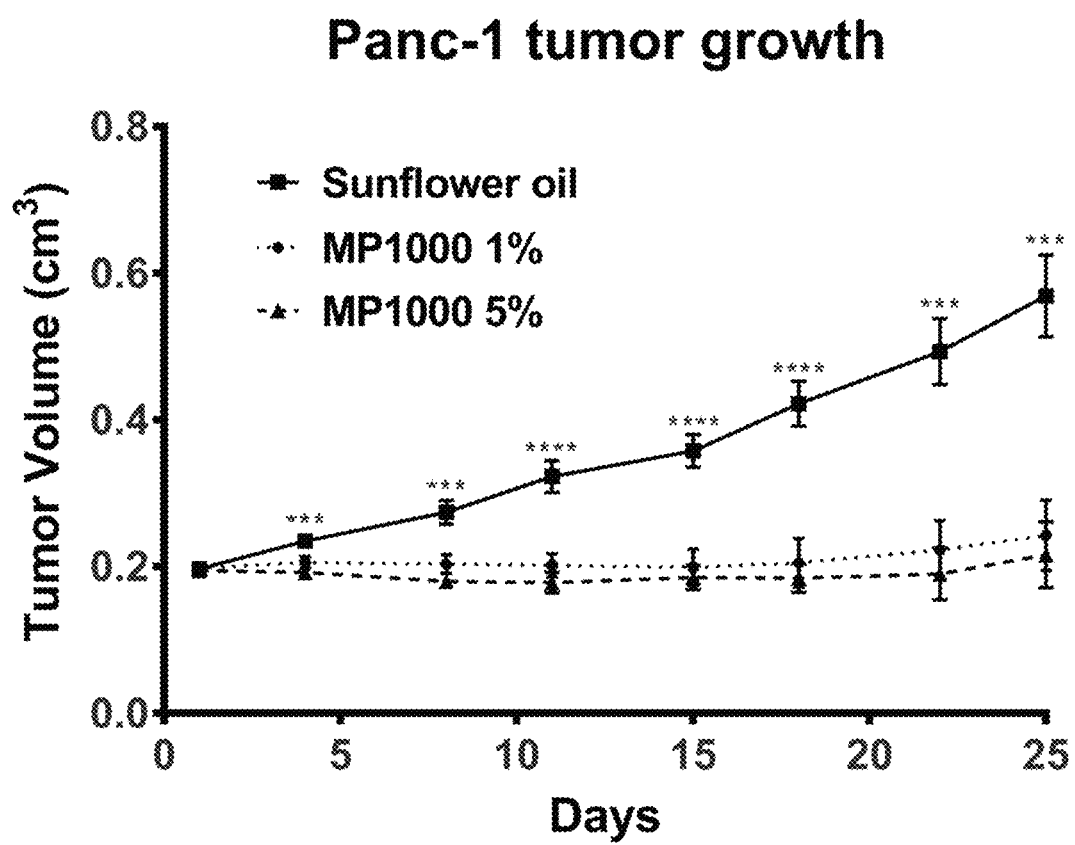

The inhibitory activity of MP1000 was investigated at 1% by weight concentration and 5% by weight concentration in mouse xenografts of cancer cell lines MiaPaca (pancreatic) and Panc-1 (pancreatic). As shown in FIGS. 7 and 8, both doses were significantly superior in retarding tumor growth as compared to control (sunflower oil). The dose response for the amount of MP1000 showed a trend towards significance after 20 days in the case of MiaPaca tumors. Each of the MP1000 samples showed statistical significance over the sunflower oil control as indicated ("*" indicates $p<0.05$, "" indicates $p<0.01$, "*" indicates $p<0.001$, and "****" indicates $p<0.0001$).

Example 8: Kinase Inhibition

Inhibition of various kinases was measured using fluorescence resonance energy transfer (FRET) analysis. Briefly, a kinase is used to transfer the γ-phosphate of ATP to a single tyrosine, serine, or threonine residue in a synthetic FRET-peptide in the presence of each tested fraction. A kinase inhibitor will prevent phosphorylation. FRET-peptides comprise a donor fluorophore and an acceptor fluorophore, where the acceptor fluorophore will only undergo fluorescence from the excitation wavelength of the donor fluorophore due to resonant energy transfer through the peptide. A development reagent is used to cleave the un-phosphorylated FRET-peptides. An uncleaved FRET-peptide (i.e., phosphorylated peptide) will therefore undergo measureable FRET of both acceptor and donor and be indicative of kinase inhibition. Cleavage of the FRET-peptide (i.e., un-phosphorylated peptides), however, disrupts FRET between donor and acceptor fluorophores on the FRET-peptide thus resulting in significantly less acceptor fluorescence and is indicative of little kinase inhibition. Because phosphorylation of FRET-peptides suppresses cleavage by the development reagent, calculation of the ratio of donor emission to acceptor emission after excitation of the donor fluorophore at approximately 400 nm is used to quantitate reaction progress. Low ratios indicate the FRET-peptide is phosphorylated (i.e., little kinase inhibition) and high ratios indicate the FRET-peptide is phosphorylated (i.e., kinase inhibition). The percent phosphorylation can therefore be calculated from the emission ratio based on controls for the maximum and minimum phosphorylation. The percent inhibition can be calculated based on the percent phosphorylation of a sample with each fraction as compared to the percent phosphorylation without each fraction.

The kinase inhibitory activity of various 10 µM solutions of various fractions was measured using the SELECTSCREEN Kinase Profiling Service available from Life Technologies. Unless otherwise indicated, the concentration of ATP in each well is the Michaelis-Menten constant ($K_m$ value-the concentration of ATP when the phosphorylation reaction velocity is equal half of the maximal velocity for the reaction). Table 13 shows the kinase inhibitory activity of the various fractions and the corresponding Z' values. Z' is a measure of statistical effect size to assess the quality of the assay. $Z'>0.5$ is indicative measurement separated from the background and a reliable assay result. The average % inhibition is representative of two independent measurements.

TABLE 12

| Fraction Name | Kinase Tested | Average % Inhibition | Z' |
|---|---|---|---|
| BAP(−) | ABL1 | −2 | 0.84 |
| BAP(−) | ABL2 (Arg) | 2 | 0.80 |
| BAP(−) | AKT1 (PKB alpha) | 6 | 0.90 |
| BAP(−) | ALK | 3 | 0.83 |
| BAP(−) | AURKB (Aurora B) | 6 | 0.71 |
| BAP(−) | AURKC (Aurora C) | 5 | 0.75 |
| BAP(−) | AXL | 4 | 0.81 |
| BAP(−)* | BRAF V599E | −1 | 0.64 |
| BAP(−)* | BRAF | −4 | 0.72 |
| BAP(−) | BTK | 9 | 0.83 |
| BAP(−) | CDC42 BPA (MRCKA) | 1 | 0.70 |
| BAP(−) | CDC42 BPB (MRCKB) | 8 | 0.57 |
| BAP(−) | CDK1/cyclin B | 3 | 0.92 |
| BAP(−) | CDK2/cyclin A | −1 | 0.84 |
| BAP(−) | CDK5/p25 | 1 | 0.66 |
| BAP(−) | CHEK1 (CHK1) | 4 | 0.80 |
| BAP(−) | CHEK2 (CHK2) | 10 | 0.84 |
| BAP(−) | CSF1R (FMS) | 3 | 0.79 |
| BAP(−) | CSNK1E (CK1 epsilon) | 4 | 0.81 |
| BAP(−) | CSNK2A1 (CK2 alpha 1) | 0 | 0.91 |
| BAP(−) | EGFR (ErbB1) | 3 | 0.89 |
| BAP(−) | EPHA1 | 5 | 0.83 |
| BAP(−) | EPHA2 | −3 | 0.82 |
| BAP(−) | EPHB2 | 4 | 0.91 |
| BAP(−) | EPHB4 | −1 | 0.73 |
| BAP(−) | ERBB2 (HER2) | −1 | 0.83 |
| BAP(−) | ERBB4 (HER4) | 0 | 0.79 |
| BAP(−) | FER | 6 | 0.88 |
| BAP(−) | FES (FPS) | 1 | 0.77 |
| BAP(−) | FGFR1 | −5 | 0.80 |
| BAP(−) | FGFR4 | −1 | 0.90 |
| BAP(−) | FGR | 12 | 0.80 |
| BAP(−) | FLT1 (VEGFR1) | 2 | 0.90 |
| BAP(−) | FLT3 | 3 | 0.78 |

TABLE 12-continued

| Fraction Name | Kinase Tested | Average % Inhibition | Z' |
|---|---|---|---|
| BAP(−) | FLT4 (VEGFR3) | −3 | 0.85 |
| BAP(−) | FYN | 16 | 0.81 |
| BAP(−) | HCK | 6 | 0.91 |
| BAP(−) | IGF1R | −9 | 0.91 |
| BAP(−) | IKBKB (IKK beta) | 3 | 0.82 |
| BAP(−) | JAK1 | −1 | 0.75 |
| BAP(−) | JAK2 JH1 JH2 V617F | 13 | 0.62 |
| BAP(−) | JAK2 JH1 JH2 | 5 | 0.85 |
| BAP(−) | JAK3 | 8 | 0.81 |
| BAP(−) | KDR (VEGFR2) | 5 | 0.77 |
| BAP(−) | KIT | 6 | 0.72 |
| BAP(−) | LCK | 7 | 0.76 |
| BAP(−) | LYN A | 2 | 0.87 |
| BAP(−)* | MAP2K1 (MEK1) | −6 | 0.79 |
| BAP(−)* | MAP3K8 (COT) | 14 | 0.87 |
| BAP(−) | MAP4K4 (HGK) | 9 | 0.72 |
| BAP(−) | MAPK14 (p38 alpha) Direct | −8 | 0.84 |
| BAP(−) | MATK (HYL) | −6 | 0.83 |
| BAP(−) | MST1R (RON) | 3 | 0.78 |
| BAP(−) | MST4 | 2 | 0.73 |
| BAP(−) | NEK2 | 3 | 0.73 |
| BAP(−) | NTRK1 (TRKA) | 4 | 0.76 |
| BAP(−) | PAK4 | 4 | 0.80 |
| BAP(−) | PDGFRA (PDGFR alpha) | 10 | 0.81 |
| BAP(−) | PDGFRB (PDGFR beta) | 5 | 0.88 |
| BAP(−) | PDK1 Direct | 9 | 0.75 |
| BAP(−) | PIM1 | 3 | 0.79 |
| BAP(−) | PLK1 | 4 | 0.85 |
| BAP(−) | PLK3 | −14 | 0.84 |
| BAP(−) | PTK2 (FAK) | 3 | 0.90 |
| BAP(−) | PTK2B (FAK2) | 0 | 0.84 |
| BAP(−) | PTK6 (Brk) | −3 | 0.82 |
| BAP(−)* | RAF1 (cRAF) Y340D Y341D | 15 | 0.81 |
| BAP(−) | RET | 6 | 0.77 |
| BAP(−) | ROCK1 | 11 | 0.86 |
| BAP(−) | ROS1 | 2 | 0.83 |
| BAP(−) | RPS6KB1 (p70S6K) | 6 | 0.78 |
| BAP(−) | SGK (SGK1) | 12 | 0.90 |
| BAP(−) | SYK | −5 | 0.84 |
| BAP(−) | TBK1 | 3 | 0.78 |
| BAP(−) | TEK (Tie2) | 3 | 0.80 |
| BAP(−) | TYRO3 (RSE) | 2 | 0.92 |
| BAP(−) | YES1 | −1 | 0.78 |
| BAP(−) | CDK7/cyclin H/MNAT1 | −4 | 0.82 |
| BAP(−) | CDK9/cyclin T1 | −3 | 0.92 |
| BAP(−) | GSG2 (Haspin) | 2 | 0.83 |
| BAP(−) | PIK3CG (p110 gamma) | 12 | 0.87 |
| BAP(−) | SPHK1 | 6 | 0.62 |
| BAP(+) | ABL1 | 15 | 0.84 |
| BAP(+) | ABL2 (Arg) | 26 | 0.80 |
| BAP(+) | AKT1 (PKB alpha) | 9 | 0.90 |
| BAP(+) | ALK | −1 | 0.83 |
| BAP(+) | AURKB (Aurora B) | 37 | 0.71 |
| BAP(+) | AURKC (Aurora C) | 16 | 0.75 |
| BAP(+) | AXL | 22 | 0.81 |
| BAP(+)* | BRAF V599E | 4 | 0.64 |
| BAP(+)* | BRAF | −6 | 0.72 |
| BAP(+) | BTK | 13 | 0.83 |
| BAP(+) | CDC42 BPA (MRCKA) | −4 | 0.70 |
| BAP(+) | CDC42 BPB (MRCKB) | 2 | 0.57 |
| BAP(+) | CDK1/cyclin B | 1 | 0.92 |
| BAP(+) | CDK2/cyclin A | 3 | 0.84 |
| BAP(+) | CDK5/p25 | 18 | 0.66 |
| BAP(+) | CHEK1 (CHK1) | −23 | 0.81 |
| BAP(+) | CHEK2 (CHK2) | 5 | 0.84 |
| BAP(+) | CSF1R (FMS) | 0 | 0.79 |
| BAP(+) | CSNK1E (CK1 epsilon) | 10 | 0.81 |
| BAP(+) | CSNK2A1 (CK2 alpha 1) | 3 | 0.91 |
| BAP(+) | EGFR (ErbB1) | 1 | 0.89 |
| BAP(+) | EPHA1 | 8 | 0.83 |
| BAP(+) | EPHA2 | −1 | 0.82 |
| BAP(+) | EPHB2 | 5 | 0.91 |
| BAP(+) | EPHB4 | 2 | 0.73 |
| BAP(+) | ERBB2 (HER2) | −12 | 0.86 |
| BAP(+) | ERBB4 (HER4) | 5 | 0.79 |
| BAP(+) | FER | 21 | 0.88 |
| BAP(+) | FES (FPS) | 3 | 0.77 |
| BAP(+) | FGFR1 | 2 | 0.80 |
| BAP(+) | FGFR4 | 15 | 0.90 |
| BAP(+) | FGR | 29 | 0.80 |
| BAP(+) | FLT1 (VEGFR1) | 7 | 0.90 |
| BAP(+) | FLT3 | 6 | 0.78 |
| BAP(+) | FLT4 (VEGFR3) | 5 | 0.85 |
| BAP(+) | FYN | 30 | 0.81 |
| BAP(+) | HCK | 7 | 0.91 |
| BAP(+) | IGF1R | −4 | 0.91 |
| BAP(+) | IKBKB (IKK beta) | 12 | 0.82 |
| BAP(+) | JAK1 | −6 | 0.75 |
| BAP(+) | JAK2 JH1 JH2 V617F | −5 | 0.62 |
| BAP(+) | JAK2 JH1 JH2 | −6 | 0.85 |
| BAP(+) | JAK3 | 13 | 0.81 |
| BAP(+) | KDR (VEGFR2) | 5 | 0.77 |
| BAP(+) | KIT | −1 | 0.72 |
| BAP(+) | LCK | 20 | 0.76 |
| BAP(+) | LYN A | 7 | 0.87 |
| BAP(+)* | MAP2K1 (MEK1) | −4 | 0.79 |
| BAP(+)* | MAP3K8 (COT) | 43 | 0.87 |
| BAP(+) | MAP4K4 (HGK) | 11 | 0.72 |
| BAP(+) | MAPK14 (p38 alpha) Direct | −4 | 0.84 |
| BAP(+) | MATK (HYL) | −6 | 0.83 |
| BAP(+) | MST1R (RON) | 2 | 0.78 |
| BAP(+) | MST4 | 3 | 0.73 |
| BAP(+) | NEK2 | −10 | 0.71 |
| BAP(+) | NTRK1 (TRKA) | −3 | 0.76 |
| BAP(+) | PAK4 | 7 | 0.80 |
| BAP(+) | PDGFRA (PDGFR alpha) | −4 | 0.81 |
| BAP(+) | PDGFRB (PDGFR beta) | 3 | 0.88 |
| BAP(+) | PDK1 Direct | 2 | 0.75 |
| BAP(+) | PIM1 | −4 | 0.79 |
| BAP(+) | PLK1 | 4 | 0.85 |
| BAP(+) | PLK3 | 18 | 0.82 |
| BAP(+) | PTK2 (FAK) | 4 | 0.90 |
| BAP(+) | PTK2B (FAK2) | 2 | 0.84 |
| BAP(+) | PTK6 (Brk) | −3 | 0.82 |
| BAP(+)* | RAF1 (cRAF) Y340D Y341D | −3 | 0.81 |
| BAP(+) | RET | 12 | 0.77 |
| BAP(+) | ROCK1 | 2 | 0.86 |
| BAP(+) | ROS1 | 5 | 0.83 |
| BAP(+) | RPS6KB1 (p70S6K) | 0 | 0.78 |
| BAP(+) | SGK (SGK1) | 21 | 0.90 |
| BAP(+) | SYK | 14 | 0.84 |
| BAP(+) | TBK1 | −5 | 0.78 |
| BAP(+) | TEK (Tie2) | 26 | 0.80 |
| BAP(+) | TYRO3 (RSE) | 3 | 0.92 |
| BAP(+) | YES1 | 18 | 0.78 |
| BAP(+) | CDK7/cyclin H/MNAT1 | −17 | 0.82 |
| BAP(+) | CDK9/cyclin T1 | 26 | 0.92 |
| BAP(+) | GSG2 (Haspin) | 36 | 0.83 |
| BAP(+) | PIK3CG (p110 gamma) | 38 | 0.87 |
| BAP(+) | SPHK1 | 83 | 0.62 |
| F1 + F2 + F3 + F4 | AURKA (Aurora A) | 62 | 0.86 |
| F1 + F2 + F3 + F4 | AURKB (Aurora B) | 66 | 0.70 |
| F1 + F2 + F3 + F4 | FRAP1 (mTOR) | 91 | 0.85 |
| F1 + F2 + F3 + F4* | MAP3K8 (COT) | 64 | 0.73 |
| F1 + F2 + F3 + F4 | GSG2 (Haspin) | 32 | 0.85 |
| F1 + F2 + F3 + F4 | PIK3CG (p110 gamma) | 48 | 0.58 |
| F1 + F2 + F3 + F4** | SPHK1 | 100 | 0.75 |
| F5 | AURKA (Aurora A) | 26 | 0.69 |
| F5 | AURKB (Aurora B) | 20 | 0.70 |
| F5 | FRAP1 (mTOR) | 7 | 0.85 |
| F5* | MAP3K8 (COT) | 38 | 0.73 |
| F5 | GSG2 (Haspin) | −2 | 0.85 |
| F5 | PIK3CG (p110 gamma) | 1 | 0.80 |
| F5 | SPHK1 | 33 | 0.75 |
| F5-2 | AURKA (Aurora A) | 12 | 0.69 |
| F5-2 | AURKB (Aurora B) | 12 | 0.70 |
| F5-2 | FRAP1 (mTOR) | −3 | 0.85 |
| F5-2* | MAP3K8 (COT) | 23 | 0.73 |
| F5-2 | GSG2 (Haspin) | 3 | 0.85 |
| F5-2 | PIK3CG (p110 gamma) | −16 | 0.80 |

TABLE 12-continued

| Fraction Name | Kinase Tested | Average % Inhibition | Z' |
|---|---|---|---|
| F5-2 | SPHK1 | 15 | 0.82 |
| F5C | AURKA (Aurora A) | 10 | 0.69 |
| F5C | AURKB (Aurora B) | 7 | 0.70 |
| F5C | FRAP1 (mTOR) | −7 | 0.85 |
| F5C* | MAP3K8 (COT) | 3 | 0.73 |
| F5C | GSG2 (Haspin) | 4 | 0.85 |
| F5C | PIK3CG (p110 gamma) | 21 | 0.58 |
| F5C | SPHK1 | −5 | 0.70 |
| F53 | AURKA (Aurora A) | 16 | 0.69 |
| F53 | AURKB (Aurora B) | 14 | 0.70 |
| F53 | FRAP1 (mTOR) | −2 | 0.85 |
| F53* | MAP3K8 (COT) | 35 | 0.73 |
| F53 | ABL1 M351T | 12 | 0.68 |
| F53 | ALK C1156Y | −5 | 0.81 |
| F53 | EGFR (ErbB1) d746-750 | 8 | 0.83 |
| F53 | KIT D816H | 18 | 0.82 |
| F53 | KIT N822K | 14 | 0.89 |
| F53 | KIT Y823D | 27 | 0.82 |
| F53 | TTK | 65 | 0.93 |
| F53 | WEE1 | 6 | 0.71 |
| F53 | GSG2 (Haspin) | −9 | 0.85 |
| F53 | PIK3CG (p110 gamma) | 43 | 0.58 |
| F53 | SPHK1 | −11 | 0.82 |
| GPC | AURKA (Aurora A) | 22 | 0.86 |
| GPC | AURKB (Aurora B) | 13 | 0.70 |
| GPC | FRAP1 (mTOR) | −1 | 0.85 |
| GPC* | MAP3K8 (COT) | 7 | 0.73 |
| GPC | GSG2 (Haspin) | 14 | 0.85 |
| GPC | PIK3CG (p110 gamma) | 2 | 0.58 |
| GPC | SPHK1 | −5 | 0.70 |
| F5-2-1 | AURKA (Aurora A) | 41 | 0.69 |
| F5-2-1 | AURKB (Aurora B) | 34 | 0.70 |
| F5-2-1 | FRAP1 (mTOR) | 5 | 0.85 |
| F5-2-1* | MAP3K8 (COT) | 64 | 0.73 |
| F5-2-1 | GSG2 (Haspin) | −1 | 0.85 |
| F5-2-1 | PIK3CG (p110 gamma) | 0 | 0.80 |
| F5-2-1 | SPHK1 | 7 | 0.70 |
| F5-2-2 | AURKA (Aurora A) | 25 | 0.69 |
| F5-2-2 | AURKB (Aurora B) | 22 | 0.70 |
| F5-2-2 | FRAP1 (mTOR) | −2 | 0.85 |
| F5-2-2* | MAP3K8 (COT) | 40 | 0.73 |
| F5-2-2 | GSG2 (Haspin) | −8 | 0.85 |
| F5-2-2 | PIK3CG (p110 gamma) | 11 | 0.58 |
| F5-2-2 | SPHK1 | 20 | 0.70 |
| F5-2-3 | AURKA (Aurora A) | 6 | 0.71 |
| F5-2-3 | AURKB (Aurora B) | 15 | 0.70 |
| F5-2-3 | FRAP1 (mTOR) | 16 | 0.85 |
| F5-2-3* | MAP3K8 (COT) | 44 | 0.73 |
| F5-2-3 | GSG2 (Haspin) | 8 | 0.85 |
| F5-2-3 | PIK3CG (p110 gamma) | 12 | 0.58 |
| F5-2-3 | SPHK1 | −16 | 0.70 |
| F5-2-5 | AURKA (Aurora A) | 10 | 0.71 |
| F5-2-5 | AURKB (Aurora B) | 15 | 0.70 |
| F5-2-5 | FRAP1 (mTOR) | 2 | 0.85 |
| F5-2-5* | MAP3K8 (COT) | 11 | 0.73 |
| F5-2-5 | GSG2 (Haspin) | 5 | 0.86 |
| F5-2-5 | PIK3CG (p110 gamma) | 12 | 0.58 |
| F5-2-5 | SPHK1 | 29 | 0.75 |

*ATP concentration of 100 μM
**Test compound showed possible interference with the acceptor As can be seen, certain fractions of BAP may more effectively inhibit of various kinases than compared to BAP(+) and BAP(−). For example, using the combination of fractions F1-F4 produced significantly greater inhibition of the mTOR kinase than fraction F5 itself, or any substituents of F5. Moreover, BAP(+) shows significant inhibitory activity on various kinases over BAP(−). For example, BAP(+) shows significant inhibitory behavior on SPHK1 kinase when BAP(−) or any other fraction studied do not (the fraction F1+F2+F3+F4 interacted with the acceptor fluorophore in the experiment and prevented any emission yielding a % inhibition of 100%).

Measurement of inhibition of various kinases was also performed by binding a tracer to a kinase and the addition of Europium labeled anti-tag antibodies. When bound to the same kinase, the tracer and Europium interact through FRET and fluoresce. Binding of the tracer and antibody to a kinase results in a high degree of FRET, whereas displacement of the tracer with a kinase inhibitor results in a loss of FRET. This method of measurement removes the cleavage step necessary in the above FRET measurement.

The kinase inhibitory activity of various 10 μM solutions of various fractions was measured (LANTHASCREEN Eu Kinase Binding Assay Profiling Service available from Life Technologies). In these measurements, greater percent displacement indicates greater kinase inhibition. Table 14 shows the percent displacement values and corresponding Z prime values of several fractions, and of BAP(+) and BAP (−). The average % displacement is representative of two independent measurements.

TABLE 13

| Fraction Name | Kinase Tested | Average % Displacement | Z' |
|---|---|---|---|
| BAP(−) | ABL1 H396P | 11 | 0.70 |
| BAP(−) | ABL1 M351T | 23 | 0.79 |
| BAP(−) | ABL1 Q252H | 32 | 0.69 |
| BAP(−) | ALK C1156Y | 11 | 0.90 |
| BAP(−) | ALK F1174L | 9 | 0.86 |
| BAP(−) | ALK L1196M | 10 | 0.75 |
| BAP(−) | ALK R1275Q | 9 | 0.91 |
| BAP(−) | EGFR (ErbB1) d746-750 | 3 | 0.60 |
| BAP(−) | EPHA3 | 4 | 0.91 |
| BAP(−) | FGFR1 V561M | 7 | 0.91 |
| BAP(−) | FGFR3 G697C | 15 | 0.84 |
| BAP(−) | FLT3 ITD | 5 | 0.64 |
| BAP(−) | KIT A829P | 5 | 0.74 |
| BAP(−) | KIT D816H | 28 | 0.72 |
| BAP(−) | KIT D816V | 16 | 0.86 |
| BAP(−) | KIT D820E | 9 | 0.96 |
| BAP(−) | KIT N822K | 15 | 0.87 |
| BAP(−) | KIT Y823D | 12 | 0.74 |
| BAP(−) | MAP3K14 (NIK) | 8 | 0.85 |
| BAP(−) | MET D1228H | 2 | 0.84 |
| BAP(−) | RET G691S | 0 | 0.59 |
| BAP(−) | RET M918T | 2 | 0.54 |
| BAP(−) | RET V804M | 8 | 0.66 |
| BAP(−) | STK33 | −2 | 0.90 |
| BAP(−) | TNK2 (ACK) | 15 | 0.96 |
| BAP(−) | TTK | 39 | 0.82 |
| BAP(−) | WEE1 | 11 | 0.73 |
| BAP(+) | ABL1 H396P | 19 | 0.70 |
| BAP(+) | ABL1 M351T | 37 | 0.61 |
| BAP(+) | ABL1 Q252H | 30 | 0.69 |
| BAP(+) | ALK C1156Y | 36 | 0.90 |
| BAP(+) | ALK F1174L | 23 | 0.86 |
| BAP(+) | ALK L1196M | 18 | 0.75 |
| BAP(+) | ALK R1275Q | 15 | 0.91 |
| BAP(+) | EGFR (ErbB1) d746-750 | 56 | 0.60 |
| BAP(+) | EPHA3 | 1 | 0.91 |
| BAP(+) | FGFR1 V561M | 13 | 0.91 |
| BAP(+) | FGFR3 G697C | 31 | 0.77 |
| BAP(+) | FLT3 ITD | 13 | 0.79 |
| BAP(+) | KIT A829P | 10 | 0.74 |
| BAP(+) | KIT D816H | 44 | 0.59 |
| BAP(+) | KIT D816V | 21 | 0.86 |
| BAP(+) | KIT D820E | 19 | 0.96 |
| BAP(+) | KIT N822K | 33 | 0.89 |
| BAP(+) | KIT Y823D | 45 | 0.74 |
| BAP(+) | MAP3K14 (NIK) | 26 | 0.85 |
| BAP(+) | MET D1228H | 2 | 0.84 |
| BAP(+) | RET G691S | 8 | 0.59 |
| BAP(+) | RET M918T | 73 | 0.54 |
| BAP(+) | RET V804M | −13 | 0.66 |
| BAP(+) | STK33 | 7 | 0.90 |
| BAP(+) | TNK2 (ACK) | 8 | 0.96 |
| BAP(+) | TTK | 97 | 0.82 |
| BAP(+) | WEE1 | 34 | 0.73 |
| F1 + F2 + F3 + F4 | ABL1 M351T | 31 | 0.68 |
| F1 + F2 + F3 + F4 | ALK C1156Y | 42 | 0.81 |

TABLE 13-continued

| Fraction Name | Kinase Tested | Average % Displacement | Z' |
|---|---|---|---|
| F1 + F2 + F3 + F4 | EGFR (ErbB1) d746-750 | 97 | 0.86 |
| F1 + F2 + F3 + F4 | KIT D816H | 37 | 0.82 |
| F1 + F2 + F3 + F4 | KIT N822K | 57 | 0.89 |
| F1 + F2 + F3 + F4 | KIT Y823D | 108 | 0.82 |
| F1 + F2 + F3 + F4 | TTK | 105 | 0.93 |
| F1 + F2 + F3 + F4 | WEE1 | 64 | 0.71 |
| F5 | ABL1 M351T | 31 | 0.60 |
| F5 | ALK C1156Y | 11 | 0.81 |
| F5 | EGFR (ErbB1) d746-750 | 11 | 0.83 |
| F5 | KIT D816H | 22 | 0.82 |
| F5 | KIT N822K | 9 | 0.89 |
| F5 | KIT Y823D | 26 | 0.82 |
| F5 | TTK | 74 | 0.93 |
| F5 | WEE1 | 8 | 0.71 |
| F5-2 | ABL1 M351T | −2 | 0.68 |
| F5-2 | ALK C1156Y | 6 | 0.81 |
| F5-2 | EGFR (ErbB1) d746-750 | 2 | 0.83 |
| F5-2 | KIT D816H | 8 | 0.82 |
| F5-2 | KIT N822K | 2 | 0.89 |
| F5-2 | KIT Y823D | 6 | 0.82 |
| F5-2 | TTK | 36 | 0.93 |
| F5-2 | WEE1 | 16 | 0.71 |
| F5C | ABL1 M351T | 3 | 0.68 |
| F5C | ALK C1156Y | −3 | 0.81 |
| F5C | EGFR (ErbB1) d746-750 | 2 | 0.83 |
| F5C | KIT D816H | 8 | 0.82 |
| F5C | KIT N822K | 0 | 0.89 |
| F5C | KIT Y823D | 4 | 0.82 |
| F5C | TTK | 30 | 0.93 |
| F5C | WEE1 | 1 | 0.71 |
| F5-3 | ABL1 M351T | 12 | 0.68 |
| F5-3 | ALK C1156Y | −5 | 0.81 |
| F5-3 | EGFR (ErbB1) d746-750 | 8 | 0.83 |
| F5-3 | KIT D816H | 18 | 0.82 |
| F5-3 | KIT N822K | 14 | 0.89 |
| F5-3 | KIT Y823D | 27 | 0.82 |
| F5-3 | TTK | 65 | 0.93 |
| F5-3 | WEE1 | 6 | 0.71 |
| GPC | ABL1 M351T | 4 | 0.68 |
| GPC | ALK C1156Y | 4 | 0.81 |
| GPC | EGFR (ErbB1) d746-750 | −1 | 0.83 |
| GPC | KIT D816H | 1 | 0.82 |
| GPC | KIT N822K | −1 | 0.89 |
| GPC | KIT Y823D | 2 | 0.82 |
| GPC | TTK | 24 | 0.93 |
| GPC | WEE1 | 5 | 0.71 |
| F5-2-1 | ABL1 M351T | 32 | 0.68 |
| F5-2-1 | ALK C1156Y | 32 | 0.81 |
| F5-2-1 | EGFR (ErbB1) d746-750 | 17 | 0.83 |
| F5-2-1 | KIT D816H | 52 | 0.82 |
| F5-2-1 | KIT N822K | 22 | 0.89 |
| F5-2-1 | KIT Y823D | 50 | 0.82 |
| F5-2-1 | TTK | 70 | 0.93 |
| F5-2-1 | WEE1 | 29 | 0.70 |
| F5-2-2 | ABL1 M351T | 9 | 0.68 |
| F5-2-2 | ALK C1156Y | 14 | 0.81 |
| F5-2-2 | EGFR (ErbB1) d746-750 | 7 | 0.83 |
| F5-2-2 | KIT D816H | 22 | 0.82 |
| F5-2-2 | KIT N822K | 9 | 0.89 |
| F5-2-2 | KIT Y823D | 25 | 0.82 |
| F5-2-2 | TTK | 47 | 0.93 |
| F5-2-2 | WEE1 | 11 | 0.71 |
| F5-2-3 | ABL1 M351T | −9 | 0.60 |
| F5-2-3 | ALK C1156Y | 16 | 0.81 |
| F5-2-3 | EGFR (ErbB1) d746-750 | −7 | 0.93 |
| F5-2-3 | KIT D816H | 13 | 0.82 |
| F5-2-3 | KIT N822K | −9 | 0.89 |
| F5-2-3 | KIT Y823D | 22 | 0.82 |
| F5-2-3 | TTK | 76 | 0.93 |
| F5-2-3 | WEE1 | 5 | 0.70 |
| F5-2-5 | ABL1 M351T | 9 | 0.68 |
| F5-2-5 | ALK C1156Y | 8 | 0.81 |
| F5-2-5 | EGFR (ErbB1) d746-750 | 4 | 0.93 |
| F5-2-5 | KIT D816H | 7 | 0.82 |
| F5-2-5 | KIT N822K | −2 | 0.89 |
| F5-2-5 | KIT Y823D | 5 | 0.82 |
| F5-2-5 | TTK | 21 | 0.93 |
| F5-2-5 | WEE1 | −1 | 0.71 |

As can be seen, certain fractions of BAP(+) provide inhibition of various kinases including important targets for cancer therapeutics such as TTK.

SPECIFIC EMBODIMENTS

Non-limiting specific embodiments are described below each of which is considered to be within the present disclosure.

Specific Embodiment 1. A pharmaceutical composition comprising a plurality of bioactive phospholipids derived from hen egg yolk and one or more pharmaceutically acceptable diluents, excipients and/or carriers, wherein said plurality of bioactive phospholipids is substantially free of N-acyl ether phosphatidylethanolamines (NAEPE).

Specific Embodiment 2. The pharmaceutical composition according to specific embodiment 1, wherein said plurality of bioactive phospholipids is substantially free of glycerophosphocholine.

Specific Embodiment 3. The pharmaceutical composition according to specific embodiment 1 or 2, wherein said plurality of bioactive phospholipids is substantially free of phosphatidylethanolamines (PE).

Specific Embodiment 4. The pharmaceutical composition of any one of specific embodiments 1-3, wherein said plurality of bioactive phospholipids is substantially free of N-palmitoyl PEs.

Specific Embodiment 5. The pharmaceutical composition of any one of specific embodiments 1-4, wherein said plurality of bioactive phospholipids is substantially free of compounds having the structure of formula (IIIa) and/or formula (IIIb):

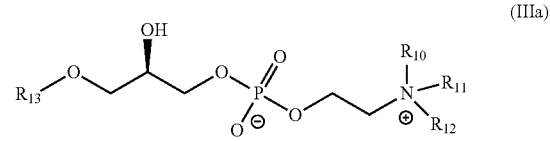

(IIIa)

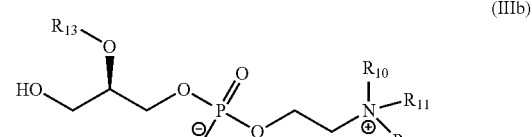

(IIIb)

wherein $R_{10}$ is selected from hydrogen, methyl, or a $C_2$-$C_{18}$ acyl group;

$R_{11}$ and $R_{12}$ are independently selected from the group consisting of hydrogen or methyl, wherein if $R_{10}$ is an acyl group, $R_{11}$ or $R_{12}$ is absent and the nitrogen bonded to $R_{10}$ is uncharged;

$R_{13}$ is independently hydrogen or a $C_2$-$C_{20}$ acyl group; and pharmaceutically acceptable salts thereof.

Specific Embodiment 6. The pharmaceutical composition of any one of specific embodiments 1-4, wherein said plurality of bioactive phospholipids further comprises compounds having the structure of formula (IIIa) and/or formula (IIIb):

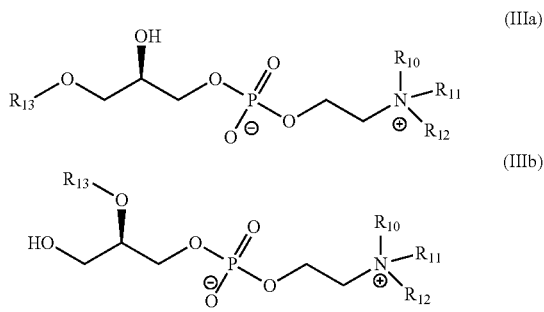

(IIIa)

(IIIb)

wherein $R_{10}$ is selected from hydrogen, methyl, or a $C_2$-$C_{18}$ acyl group;

$R_{11}$ and $R_{12}$ are independently selected from the group consisting of hydrogen or methyl, wherein if $R_{10}$ is an acyl group, $R_{11}$ or $R_{12}$ is absent and the nitrogen bonded to $R_{10}$ is uncharged;

$R_{13}$ is independently hydrogen or a $C_2$-$C_{20}$ acyl group; and pharmaceutically acceptable salts thereof.

Specific Embodiment 7. The pharmaceutical composition according to specific embodiment 5 or 6, wherein $R_{13}$ is hydrogen, palmitoyl (C16:0), stearoyl (C18:0), oleoyl (C18:1), linoleoyl (C18:2), or arachidonoyl (C20:4).

Specific Embodiment 8. The pharmaceutical composition according to specific embodiment 5 or 6, wherein $R_{13}$ is hydrogen.

Specific Embodiment 9. The pharmaceutical composition according to any one of specific embodiments 5-8, wherein $R_{10}$-12 are each methyl.

Specific Embodiment 10. A pharmaceutical composition comprising a plurality of bioactive phospholipids derived from egg yolk and one or more pharmaceutically acceptable diluents, excipients, and/or carriers, wherein said plurality of phospholipids is enriched in one or more lipids selected from the group consisting of:

one or more phosphatidylethanolamine (PE) and/or phosphatidylcholine (PC) derivatives having the structure:

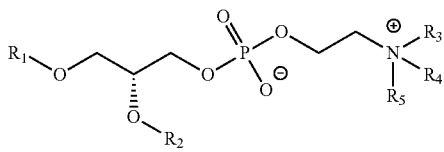

where $R_1$ or $R_2$ are independently selected from the group consisting of hydrogen, palmitoyl (C16:0), hexadecenoyl (C16:1), palmitoleoyl (C16:1), stearoyl (C18:0), octadecenoyl (C18:1), oleoyl (C18:1), octadecadienoyl (C18:2), linoleoyl (C18:2), α-linolenoyl (C18:3), octadecatrienoyl (C18:3), arachidonoyl (C20:4), eicosatetraenoyl (C20:4), docosapentaenoyl (C22:5), and docosahexaenoyl (C22:6) radicals;

$R_3$ is selected from hydrogen, methyl, or a $C_2$-$C_{18}$ acyl group; wherein if $R_3$ is an acyl group then the $R_4$ or $R_5$ is absent and the nitrogen bonded to $R_3$ is uncharged;

$R_4$ and $R_5$ are independently selected from the group consisting of hydrogen or methyl, or pharmaceutically acceptable salts thereof; and/or one or more sphingomyelin (SPH) derivatives having the structure

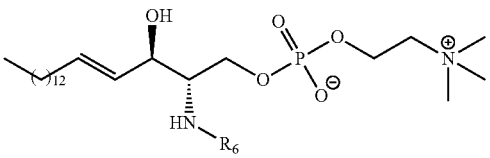

wherein $R_6$ is palmitoyl (C16:0), stearoyl (C18:0), oleoyl (C18:1), tetradecanoyl (C14:0), heptadecanoyl (C17:0), nonadecanoyl (C19:0), eicosanoyl (C20:0), docosanoyl (C22:0), docosenoyl (C22:1), henicosanoyl (C23:0), tetracosadienoic (C24:2), or tetracosanoyl (C14:0); and pharmaceutically acceptable salts thereof.

Specific Embodiment 11. The pharmaceutical composition according to specific embodiment 10, wherein $R_1$ and $R_2$ are not hydrogen.

Specific Embodiment 12. The pharmaceutical composition according to specific embodiment 10, wherein $R_1$ is selected from hydrogen, C16 or C18 fatty acid acyl radicals.

Specific Embodiment 13. The pharmaceutical composition according to specific embodiment 10, wherein $R_1$ is selected from hydrogen, palmitoyl (C16:0), palmitoleoyl (C16:1), stearoyl (C18:0), and oleoyl (C18:1).

Specific Embodiment 14. The pharmaceutical composition according to any one of specific embodiments 10-13, wherein $R_2$ is selected from C18 fatty acid acyl radicals.

Specific Embodiment 15. The pharmaceutical composition according to any one of specific embodiments 10-13, wherein $R_2$ is selected from linoleoyl (C18:2) and oleoyl (C18:1).

Specific Embodiment 16. The pharmaceutical composition according to any one of specific embodiments 10-15, wherein $R_3$, $R_4$, $R_5$ are each methyl.

Specific Embodiment 17. The pharmaceutical composition according to any one of specific embodiments 10-16, wherein said one or more phosphatidylcholine (PC) derivatives collectively comprise at least about 30% (w/w) of said plurality of phospholipids.

Specific Embodiment 18. The pharmaceutical composition according to any one of specific embodiments 10-16, wherein said one or more one or more phosphatidylcholine (PC) derivatives collectively comprise at least about 50% (w/w) of said plurality of phospholipids.

Specific Embodiment 19. The pharmaceutical composition according to any one of specific embodiments 10-16, wherein said one or more phosphatidylcholine (PC) derivatives collectively comprise at least about 70% (w/w) of said plurality of phospholipids.

Specific Embodiment 20. The pharmaceutical composition according to any one of specific embodiments 10-16, wherein said one or more phosphatidylcholine (PC) derivatives collectively comprise at least about 90% (w/w) of said plurality of phospholipids.

Specific Embodiment 21. The pharmaceutical composition according to any one of specific embodiments 10-20, wherein said one or more sphingomyelin (SPH) derivatives collectively comprise between about 0.1% and 50% (w/w) of said plurality of phospholipids.

Specific Embodiment 22. The pharmaceutical composition according to any one of specific embodiments 10-21, wherein $R_6$ is palmitoyl (C16:0).

Specific Embodiment 23. The pharmaceutical composition according to any one of specific embodiments 10-22, wherein said plurality of phospholipids is enriched in one or more phosphatidylcholine (PC) compounds and one or more sphingomyelin (SPH) compounds.

Specific Embodiment 24. The pharmaceutical composition according to any one of specific embodiments 10-23, wherein said plurality of bioactive phospholipids is substantially free of N-acyl ether phosphatidylethanolamines (NAEPE).

Specific Embodiment 25. The pharmaceutical composition according to any one of specific embodiments 10-24, wherein said plurality of bioactive phospholipids is substantially free of phosphatidylethanolamines (PE).

Specific Embodiment 26. The pharmaceutical composition of any one of specific embodiments 10-25, wherein said plurality of bioactive phospholipids is substantially free of N-palmitoyl PE's.

Specific Embodiment 27. The pharmaceutical composition according to any one of specific embodiments 10-26, wherein said plurality of bioactive phospholipids is substantially free of compounds having the structure:

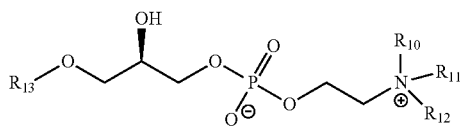

wherein $R_{10}$ is selected from hydrogen, methyl, or a $C_2$-$C_{18}$ acyl group;
$R_{11}$ and $R_{12}$ are independently selected from the group consisting of hydrogen or methyl and if $R_{10}$ is an acyl group, $R_{11}$ or $R_{12}$ is absent and the nitrogen bonded to $R_{10}$ is uncharged; and
$R_{13}$ is hydrogen or a $C_2$-$C_{20}$ acyl group;
and pharmaceutically acceptable salts thereof.

Specific Embodiment 28. The pharmaceutical composition according to specific embodiment 27, wherein $R_{13}$ is hydrogen, palmitoyl (C16:0), stearoyl (C18:0), oleoyl (C18:1), linoleoyl (C18:2), or arachidonoyl (C20:4).

Specific Embodiment 29. The pharmaceutical composition according to specific embodiment 27 or 28, wherein $R_{13}$ is hydrogen.

Specific Embodiment 30. The pharmaceutical composition according to any one of specific embodiments 27-29, wherein $R_{10-12}$ are each methyl.

Specific Embodiment 31. The pharmaceutical composition according to specific embodiment 10, wherein said plurality of bioactive phospholipids is substantially free of glycerophosphocholine.

Specific Embodiment 32. The pharmaceutical composition according to any one of specific embodiments 10-26, wherein said plurality of bioactive phospholipids further comprises one or more compounds having the structure of formula (IIIa) and/or formula (IIIb):

(IIIa)

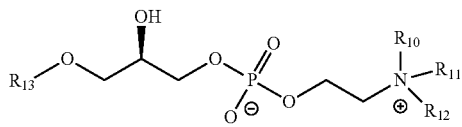

(IIIb)

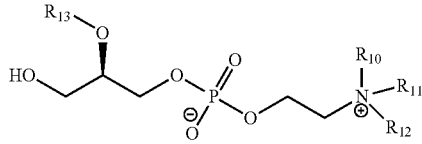

wherein $R_{10}$ is selected from hydrogen, methyl, or a $C_2$-$C_{18}$ acyl group;
$R_{11}$ and $R_{12}$ are independently selected from the group consisting of hydrogen or methyl, wherein if $R_{10}$ is an acyl group, $R_1$ or $R_{12}$ is absent and the nitrogen bonded to $R_{10}$ is uncharged;
$R_{13}$ is independently hydrogen or a $C_2$-$C_{20}$ acyl group; and
pharmaceutically acceptable salts thereof.

Specific Embodiment 33. The pharmaceutical composition according to specific embodiment 32, wherein $R_{13}$ is hydrogen, palmitoyl (C16:0), stearoyl (C18:0), oleoyl (C18:1), linoleoyl (C18:2), or arachidonoyl (C20:4).

Specific Embodiment 34. The pharmaceutical composition according to specific embodiment 32, wherein $R_{13}$ is hydrogen.

Specific Embodiment 35. The pharmaceutical composition according to any one of specific embodiments 32-34, wherein $R_{10-12}$ are each methyl.

Specific Embodiment 36. The pharmaceutical composition according to specific embodiment 32, wherein said plurality of bioactive phospholipids further comprises glycerophosphocholine.

Specific Embodiment 37. The pharmaceutical composition according to any one of specific embodiments 10-36, wherein $R_1$ and $R_2$ are each independently selected from palmitoyl (C16:0), hexadecenoyl (C16:1; cis-9), octadecenoyl (C18:0), octadecenoyl (C18:1, cis-9), octadecadienoyl (C18:2, all cis-9,12), eicosatetraenoyl (C20:4, all cis-5,8,11,14), docosahexaenoyl (C22:6, all cis-4,7,10,13, 16,19), octadecatrienoyl (C18:3, all cis-9,12,15), and docosapentaenoyl (C22:5, all cis-7,10,13,16,19).

Specific Embodiment 38. The pharmaceutical composition according to specific embodiment 10, wherein $R_3$-$R_5$ are methyl, such that said plurality of bioactive phospholipids comprises a phosphatidylcholine (PC) component; wherein at least 50% (w/w) of said phosphatidylcholine (PC) component comprises one or more compounds selected from the group consisting of:
1-palmitoyl-2-linoleoyl-sn-glycero-3-phosphocholine,
1-palmitoyl-2-α-linolenoyl-sn-glycero-3-phosphocholine,
1-palmitoyl-2-arachidonoyl-sn-glycero-3-phosphocholine,
1-linoleoyl-2-linoleoyl-sn-glycero-3-phosphocholine,
1-palmitoyl-2-docosahexaenoyl-sn-glycero-3-phosphocholine,
1-α-linolenoyl-2-docosahexaenoyl-sn-glycero-3-phosphocholine,
1-palmitoleoyl-2-oleoyl-sn-glycero-3-phosphocholine,
1-palmitoyl-2-linoleoyl-sn-glycero-3-phosphocholine,
1-palmitoyl-2-clupanodonoyl-sn-glycero-3-phosphocholine,
1-palmitoleoyl-2-docosahexaenoyl-sn-glycero-3-phosphocholine,
1-palmitoyl-2-osbondoyl-sn-glycero-3-phosphocholine,
1-oleoyl-2-arachidonoyl-sn-glycero-3-phosphocholine,
1-oleoyl-2-linoleoyl-sn-glycero-3-phosphocholine,
1,2-dioleoyl-sn-glycero-3-phosphocholine,
1-stearoyl-2-arachidonoyl-sn-glycero-3-phosphocholine, 1-stearoyl-2-linoleoyl-sn-glycero-3-phosphocholine,
1-hydroxy-oleoyl-sn-glycero-3-phosphocholine
1-palmitoyl-2-oleoyl-sn-glycero-3-phosphocholine, and
1-oleoyl-2-docosahexaenoyl-sn-glycero-3-phosphocholine;
and pharmaceutically acceptable salts thereof.

Specific Embodiment 39. The pharmaceutical composition according to specific embodiment 38, wherein said docosahexaenoyl group in 1-palmitoyl-2-docosahexaenoyl-sn-glycero-3-phosphocholine, 1-α-linolenoyl-2-docosahexaenoyl-sn-glycero-3-phosphocholine, 1-palmitoleoyl-2-docosahexaenoyl-sn-glycero-3-phosphocholine, and 1-oleoyl-2-docosahexaenoyl-sn-glycero-3-phosphocholine is (4Z,7Z,10Z,13Z,16Z,19Z)-docosa-4,7,10,13,16,19-hexaenoyl.

Specific Embodiment 40. The pharmaceutical composition according to specific embodiment 10, wherein said plurality of bioactive phospholipids comprises a phosphatidylcholine (PC) component; wherein at least 50% (w/w) of said phosphatidylcholine (PC) component comprises one or more compounds selected from the group consisting of:
1-palmitoyl-2-linoleoyl-sn-glycero-3-phosphocholine,
1-palmitoleoyl-2-oleoyl-sn-glycero-3-phosphocholine,
1-palmitoyl-2-linoleoyl-sn-glycero-3-phosphocholine,
1-stearoyl-2-linoleoyl-sn-glycero-3-phosphocholine, and
1-hydroxy-2-palmitoyl-sn-glycero-3-phosphocholine; and pharmaceutically acceptable salts thereof.

Specific Embodiment 41. The pharmaceutical composition according to any one of specific embodiments 10-40, wherein said plurality of bioactive phospholipids comprises a sphingomyelin (SPH) component, wherein at least 50% (w/w) of said sphingomyelin (SPH) component comprises one or more compounds selected from the group consisting of:
N-palmitoyl-D-erythro-sphingosylphosphorylcholine,
N-stearoyl-D-erythro-sphingosylphosphorylcholine, and
N-oleoyl-D-erythro-sphingosylphosphorylcholine.

Specific Embodiment 42. The pharmaceutical composition according to specific embodiment 41, wherein said sphingomyelin (SPH) component comprises N-palmitoyl-D-erythro-sphingosylphosphorylcholine.

Specific Embodiment 43. A pharmaceutical composition comprising a plurality of phosphatidylcholine (PC) compounds and one or more pharmaceutically acceptable diluents, excipients and/or carriers; wherein at least 50% (w/w) of said phosphatidylcholine (PC) compounds are selected from the group consisting of:
1-palmitoyl-2-linoleoyl-sn-glycero-3-phosphocholine,
1-palmitoyl-2-α-linolenoyl-sn-glycero-3-phosphocholine,
1-palmitoyl-2-arachidonoyl-sn-glycero-3-phosphocholine,
1-linoleoyl-2-linoleoyl-sn-glycero-3-phosphocholine,
1-palmitoyl-2-docosahexaenoyl-sn-glycero-3-phosphocholine,
1-α-linolenoyl-2-docosahexaenoyl-sn-glycero-3-phosphocholine,
1-palmitoleoyl-2-oleoyl-sn-glycero-3-phosphocholine,
1-palmitoyl-2-linoleoyl-sn-glycero-3-phosphocholine,
1-palmitoyl-2-clupanodonoyl-sn-glycero-3-phosphocholine,
1-palmitoleoyl-2-docosahexaenoyl-sn-glycero-3-phosphocholine,
1-palmitoyl-2-osbondoyl-sn-glycero-3-phosphocholine,
1-oleoyl-2-arachidonoyl-sn-glycero-3-phosphocholine,
1-oleoyl-2-linoleoyl-sn-glycero-3-phosphocholine,
1-stearoyl-2-arachidonoyl-sn-glycero-3-phosphocholine,
1-hydroxy-2-palmitoyl-sn-glycero-3-phosphocholine,
1-palmitoyl-2-oleoyl-sn-glycero-3-phosphocholine, and
1-oleoyl-2-docosahexaenoyl-sn-glycero-3-phosphocholine;
and pharmaceutically acceptable salts thereof.

Specific Embodiment 44. The pharmaceutical composition according to specific embodiment 43, wherein said docosahexaenoyl group in 1-palmitoyl-2-docosahexaenoyl-sn-glycero-3-phosphocholine, 1-α-linolenoyl-2-docosahexaenoyl-sn-glycero-3-phosphocholine, 1-palmitoleoyl-2-docosahexaenoyl-sn-glycero-3-phosphocholine, and 1-oleoyl-2-docosahexaenoyl-sn-glycero-3-phosphocholine is (4Z,7Z,10Z,13Z,16Z,19Z)-docosa-4,7,10,13,16,19-hexaenoyl.

Specific Embodiment 45. The pharmaceutical composition according to specific embodiment 43 or 44 further comprising a sphingomyelin (SPH) component, wherein said sphingomyelin (SPH) component comprises one or more compounds selected from the group consisting of:
N-palmitoyl-D-erythro-sphingosylphosphorylcholine,
N-stearoyl-D-erythro-sphingosylphosphorylcholine, and
N-oleoyl-D-erythro-sphingosylphosphorylcholine.

Specific Embodiment 46. The pharmaceutical composition according to specific embodiment 45, wherein at least 50% (w/w) of said sphingomyelin (SPH) component comprises N-palmitoyl-D-erythro-sphingosylphosphorylcholine.

Specific Embodiment 47. The pharmaceutical composition according to specific embodiment 45, wherein at least 80% (w/w) of said sphingomyelin (SPH) component comprises N-palmitoyl-D-erythro-sphingosylphosphorylcholine.

Specific Embodiment 48. The pharmaceutical composition according to specific embodiment 45, wherein at least 90% (w/w) of said sphingomyelin (SPH) component comprises N-palmitoyl-D-erythro-sphingosylphosphorylcholine.

Specific Embodiment 49. A pharmaceutical composition comprising a plurality of sphingomyelin (SPH) compounds and one or more pharmaceutically acceptable diluents, excipients and/or carriers; wherein at least 50% (w/w) of said sphingomyelin (SPH) compounds are selected from the group consisting of:
N-palmitoyl-D-erythro-sphingosylphosphorylcholine,
N-stearoyl-D-erythro-sphingosylphosphorylcholine, and
N-oleoyl-D-erythro-sphingosylphosphorylcholine.

Specific Embodiment 50. The pharmaceutical composition according to specific embodiment 49, wherein said sphingomyelin (SPH) component comprises N-palmitoyl-D-erythro-sphingosylphosphorylcholine.

Specific Embodiment 51. The pharmaceutical composition according to specific embodiment 49, wherein said sphingomyelin (SPH) component consists or consists essentially of N-palmitoyl-D-erythro-sphingosylphosphorylcholine.

Specific Embodiment 52. The pharmaceutical composition according to any one of specific embodiments 1-51, wherein said plurality of bioactive phospholipids is derived from hen egg yolk by alcohol extraction.

Specific Embodiment 53. The pharmaceutical composition according to any one of specific embodiments 1-52, wherein said plurality of bioactive phospholipids is derived from hen egg yolk that has been reacted with an activated carboxylic acid species.

Specific Embodiment 54. The pharmaceutical composition according to specific embodiment 53, wherein said carboxylic acid is a fatty acid.

Specific Embodiment 55. The pharmaceutical composition according to specific embodiment 53, wherein said derivation of bioactive phospholipids comprises one or more chromatographic separations of chemically reacted hen egg yolk.

Specific Embodiment 56. The pharmaceutical composition according to specific embodiment 55, wherein said chromatographic separation comprises medium pressure silica gel chromatography.

Specific Embodiment 57. The pharmaceutical composition according to specific embodiment 55, wherein said chromatographic separation is performed with at least one silica column and a suboptimal flow rate for said column.

Specific Embodiment 58. The pharmaceutical composition according to specific embodiment 57, wherein said flow rate is less than about 80% of the optimal flow rate.

Specific Embodiment 59. The pharmaceutical composition according to specific embodiment 57, wherein said flow rate is less than about 50% of the optimal flow rate.

Specific Embodiment 60. The pharmaceutical composition according to any one of specific embodiments 55-59, wherein said chromatographic separation is performed with one or more eluents comprising chloroform.

Specific Embodiment 61. The pharmaceutical composition according to specific embodiment 60, wherein said chromatographic separation is performed with at least two different eluents.

Specific Embodiment 62. The pharmaceutical composition according to specific embodiment 61, wherein one of said at least two eluents is basic and the other of said at least two eluents is alcoholic.

Specific Embodiment 63. The pharmaceutical composition according to specific embodiment 62, wherein said basic eluent comprises ammonium hydroxide.

Specific Embodiment 64. The pharmaceutical composition according to specific embodiment 62 or 63, wherein said alcoholic eluent comprises methanol, ethanol, propanol, isopropanol, butanol, or combinations thereof.

Specific Embodiment 65. A pharmaceutical composition comprising an effective amount of (R)-2-(((4Z,7Z,10Z,13Z,16Z,19Z)-docosa-4,7,10,13,16,19-hexaenoyl)oxy)-3-(palmitoyloxy)propyl (2-(trimethylammonio)ethyl) phosphate ("MPC1") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 66. A pharmaceutical composition comprising an effective amount of (R)-2(R)-2-(((9Z,12Z)-octadeca-9,12-dienoyl)oxy)-3-((Z)-hexadec-9-enoyl)oxy)propyl (2-(trimethylammonio)ethyl) phosphate ("MPC2") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 67. A pharmaceutical composition comprising an effective amount of (R)-2((9Z,12Z,15Z)-octadeca-9,12,15-trienoyl)oxy)-3-((Z)-hexadec-9-enoyl)oxy)propyl (2-(trimethylammonio)ethyl) phosphate ("MPC3") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 68. A pharmaceutical composition comprising an effective amount of (R)-2,3-bis(((9Z,12Z)-octadeca-9,12-dienoyl)oxy)propyl (2-(trimethylammonio)ethyl) phosphate ("MPC4") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 69. A pharmaceutical composition comprising an effective amount of (R)-2-(((9Z,12Z,15Z)-octadeca-9,12,15-trienoyl)oxy)-3-(oleoyloxy)propyl (2-(trimethylammonio)ethyl) phosphate ("MPC5") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 70. A pharmaceutical composition comprising an effective amount of (R)-2((5Z,8Z,11Z,14Z)-icosa-5,8,11,14-tetraenoyl)oxy)-3-(palmitoyloxy)propyl (2-(trimethylammonio)ethyl) phosphate ("MPC6") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 71. A pharmaceutical composition comprising an effective amount of (R)-2((7Z,10Z,13Z,16Z,19Z)-docosa-7,10,13,16,19-pentaenoyl)oxy)-3-(palmitoyloxy)propyl (2-(trimethylammonio)ethyl) phosphate ("MPC7") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 72. A pharmaceutical composition comprising an effective amount of (R)-2((5Z,8Z,11Z,14Z)-icosa-5,8,11,14-tetraenoyl)oxy)oxy)-3-(oleoyloxy)propyl (2-(trimethylammonio)ethyl) phosphate ("MPC8") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 73. A pharmaceutical composition comprising an effective amount of (R)-2-(((9Z,12Z)-octadeca-9,12-dienoyl)oxy)-3-(palmitoyloxy)propyl (2-(trimethylammonio)ethyl) phosphate ("MPC9") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 74. A pharmaceutical composition comprising an effective amount of (R)-2-((Z)-octadeca-9-enoyl)oxy)-3-((Z)-hexadec-9-enoyl)oxy)propyl (2-(trimethylammonio)ethyl) phosphate ("MPC10") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 75. A pharmaceutical composition comprising an effective amount of (R)-2-(((9Z,12Z)-octadeca-9,12-dienoyl)oxy)-3-(oleoyloxy)propyl (2-(trimethylammonio)ethyl) phosphate ("MPC11") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 76. A pharmaceutical composition comprising an effective amount of (R)-2-(((4Z,7Z,10Z,13Z,16Z,19Z)-docosa-4,7,10,13,16,19-hexaenoyl)oxy)-3-(stearoyloxy)propyl (2-(trimethylammonio)ethyl) phosphate ("MPC12") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 77. A pharmaceutical composition comprising an effective amount of (R)-2-(((5Z,8Z,11Z,14Z)-icosa-5,8,11,14-tetraenoyl)oxy)-3-(stearoyloxy)propyl (2-(trimethylammonio)ethyl) phosphate ("MPC13") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 78. A pharmaceutical composition comprising an effective amount of (R)-2-(oleoyloxy)-3-(palmitoyloxy)propyl (2-(trimethylammonio)ethyl) phosphate ("MPC14") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 79. A pharmaceutical composition comprising an effective amount of (R)-2-(((9Z,12Z)-octadeca-9,12-dienoyl)oxy)-3-(stearoyloxy)propyl (2-(trimethylammonio)ethyl) phosphate ("MPC15") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 80. A pharmaceutical composition comprising an effective amount of (R)-2,3-bis(oleoyloxy)propyl (2-(trimethylammonio)ethyl) phosphate ("MPC16") and an effective amount of (2S,3R,E)-2-palmitamido-3-hydroxyoctadec-4-en-1-yl (2-(trimethylammonio)ethyl) phosphate ("SPH1") together with one or more pharmaceutically acceptable excipients, diluents, and/or carriers.

Specific Embodiment 81. A pharmaceutical composition comprising an effective amount of (R)-2-(oleoyloxy)-3-(stearoyloxy)propyl (2-(trimethylammonio)ethyl) phosphate ("MPC17") and an effective amount of (2S,3R,E)-2-palmitamido-3-hydroxyoctadec-4-en-1-yl (2-(trimethylammonio) ethyl) phosphate ("SPH1") together with one or more pharmaceutically acceptable excipients, diluents, and/or carriers.

Specific Embodiment 82. The pharmaceutical composition according to any one of specific embodiments 65-81, wherein said effective amounts comprise from about 1 mg to about 2000 mg.

Specific Embodiment 83. The pharmaceutical composition according to any one of specific embodiments 65-81, wherein said effective amounts comprise from about 10 mg to about 1200 mg.

Specific Embodiment 84. The pharmaceutical composition according to any one of specific embodiments 65-81, wherein said effective amounts comprise from about 100 mg to about 1000 mg.

Specific Embodiment 85. The pharmaceutical composition according to any one of specific embodiments 65-84, wherein said pharmaceutical composition is in the form of an oral dosage form.

Specific Embodiment 86. The pharmaceutical composition according to specific embodiment 85, wherein said oral dosage form is in the form of a capsule.

Specific Embodiment 87. A method of treating a proliferative disease in a human patient in need thereof comprising administering to said patient a therapeutically effective amount of the pharmaceutical composition of any of specific embodiments 1-82.

Specific Embodiment 88. The method according to specific embodiment 87, wherein said proliferative disease is cancer.

Specific Embodiment 89. The method according to specific embodiment 87, wherein said proliferative disease is bladder, brain breast, cervical, colorectal, esophageal, kidney, liver, lung, ovarian, pancreatic, thyroid or uterine cancer.

Specific Embodiment 90. The method according to specific embodiment 87, wherein said therapeutically effective amount comprises from about 100 mg to about 10 g daily.

Specific Embodiment 91. The method according to specific embodiment 87, wherein said pharmaceutical composition is administered orally.

Specific Embodiment 92. The method according to specific embodiment 91, wherein said pharmaceutical composition is in the form of a capsule.

Specific Embodiment 93. A method of treating inflammation in a human patient in need thereof comprising administering to said patient a therapeutically effective amount of the pharmaceutical composition of any of specific embodiments 1-82.

Specific Embodiment 94. A method for extracting a mixture biologically active phospholipids from egg yolk comprising isolating said mixture from said egg yolk by silica gel chromatography and/or medium pressure chromatography.

Specific Embodiment 95. The method according to specific embodiment 94, wherein said chromatography is performed with a silica column and a flow rate that is suboptimal for said column size.

Specific Embodiment 96. The method according to specific embodiment 95, wherein said flow rate is less than about 80% of the optimal flow rate.

Specific Embodiment 97. The method composition according to specific embodiment 95, wherein said flow rate is less than about 50% of the optimal flow rate.

Specific Embodiment 98. The method composition according to any one of specific embodiments 94-97, wherein said chromatography is performed with one or more eluents comprising chloroform.

Specific Embodiment 99. The method composition according to any one of specific embodiments 94-98, wherein said chromatography is performed with at least two different eluents.

Specific Embodiment 100. The method composition according to specific embodiment 99, wherein one of said at least two eluents is basic and the other of said at least two eluents is alcoholic.

Specific Embodiment 101. The method composition according to specific embodiment 100, wherein said basic eluent comprises ammonium hydroxide.

Specific Embodiment 102. The method composition according to specific embodiment 100 or 101, wherein said alcoholic eluent comprises methanol, ethanol, propanol, isopropanol, butanol, or combinations thereof.

Specific Embodiment 103. The method according to any one of specific embodiments 94-102 further comprising extracting said isolated fractions with a solution comprising chloroform.

As can be seen foregoing, the present invention provides for compositions effective in pharmaceutical compositions used in the treatment of various cancers. The examples described herein are indicative of the beneficial effects possible with the described pharmaceutical compositions. However, it should be understood that such description is solely for convenience and clarity and is not intended to be limiting in scope.

The invention claimed is:

1. A method of treating leukemia in a human patient in need thereof comprising administering to said patient a pharmaceutical composition consisting of a plurality of phosphatidylcholine compounds and one or more pharmaceutically acceptable diluents, excipients, and/or carriers: wherein said plurality of phosphatidylcholine compounds comprise 1-palmitoyl-2-linoleoyl-sn-glycero-3-phosphocholine and one or more phosphatidylcholines selected from the group consisting of:
- 1-palmitoleoyl-2-linoleoyl-sn-glycero-3-phosphocholine,
- 1-palmitoyl-2-α-linolenoyl-sn-glycero-3-phosphocholine,
- 1-palmitoyl-2-arachidonoyl-sn-glycero-3-phosphocholine,
- 1-palmitoyl-2-docosahexaenoyl-sn-glycero-3-phosphocholine,
- 1-α-linolenoyl-2-docosahexaenoyl-sn-glycero-3-phosphocholine,
- 1-palmitoleoyl-2-oleoyl-sn-glycero-3-phosphocholine,
- 1-palmitoleoyl-2-docosahexaenoyl-sn-glycero-3-phosphocholine,
- 1-palmitoyl-2-osbodnoyl-sn-glycero-3-phosphocholine,
- 1-oleoyl-2-arachidonoyl-sn-glycero-3-phosphocholine,
- 1-oleoyl-2-linoleoyl-sn-glycero-3-phosphocholine,
- 1-stearoyl-2-arachidonoyl-sn-glycero-3-phosphocholine,
- 1-palmitoyl-2-oleoyl-sn-glycero-3-phosphocholine,
- 1-oleoyl-2-docosahexenoyl-sn-glycero-3-phosphocholine,
- 1,2-dioleoyl-sn-glycero-3-phosphocholine,
- 1-stearoyl-2-linoleoyl-sn-glycero-3-phosphocholine, and
- 1-stearoyl-2-oleoyl-sn-glycero-3-phosphocholine.

* * * * *